(12) United States Patent
Beasley et al.

(10) Patent No.: US 10,093,920 B2
(45) Date of Patent: Oct. 9, 2018

(54) PROTEIN DISPLAY

(75) Inventors: Matthew Beasley, Fitzroy North (AU);
Ben Kiefel, Mitcham (AU)

(73) Assignee: AFFINITY BIOSCIENCES PTY LTD, Burwood, Victoria (AU)

( * ) Notice: Subject to any disclaimer, the term of this patent is extended or adjusted under 35 U.S.C. 154(b) by 297 days.

(21) Appl. No.: 13/518,705

(22) PCT Filed: Dec. 20, 2010

(86) PCT No.: PCT/AU2010/001702
§ 371 (c)(1),
(2), (4) Date: Oct. 9, 2012

(87) PCT Pub. No.: WO2011/075761
PCT Pub. Date: Jun. 30, 2011

(65) Prior Publication Data
US 2013/0023421 A1    Jan. 24, 2013

(30) Foreign Application Priority Data

Dec. 23, 2009 (AU) .............................. 2009906310

(51) Int. Cl.
| C12N 15/10 | (2006.01) |
| C12N 15/63 | (2006.01) |
| C12N 15/70 | (2006.01) |
| C40B 50/06 | (2006.01) |
| G01N 33/68 | (2006.01) |
| C12Q 1/02  | (2006.01) |
| C40B 30/08 | (2006.01) |
| C40B 30/04 | (2006.01) |

(52) U.S. Cl.
CPC ..... *C12N 15/1034* (2013.01); *C12N 15/1055* (2013.01); *C12N 15/63* (2013.01); *C12N 15/70* (2013.01); *C40B 50/06* (2013.01); *G01N 33/6842* (2013.01); *C12Q 1/02* (2013.01); *C40B 30/04* (2013.01); *C40B 30/08* (2013.01)

(58) Field of Classification Search
None
See application file for complete search history.

(56) References Cited

U.S. PATENT DOCUMENTS

| 4,788,135 | A  | 11/1988 | Davis et al. |
| 4,946,778 | A  | 8/1990  | Ladner et al. |
| 5,223,409 | A  | 6/1993  | Ladner et al. |
| 5,571,698 | A  | 11/1996 | Ladner et al. |
| 5,591,604 | A  | 1/1997  | Fuchs et al. |
| 5,837,500 | A  | 11/1998 | Ladner et al. |
| 6,818,418 | B1 | 11/2004 | Lipovsek et al. |
| 6,916,474 | B2 | 7/2005  | Harvey et al. |
| 7,083,945 | B1 | 8/2006  | Chen et al. |
| 7,094,571 | B2 | 8/2006  | Harvey et al. |
| 7,435,804 | B2 | 10/2008 | Kordyum et al. |
| 7,611,866 | B2 | 11/2009 | Georgiou et al. |
| 2003/0036092 | A1 | 2/2003 | Iverson et al. |
| 2005/0147962 | A1 | 7/2005 | Wagstrom et al. |
| 2005/0267294 | A1 | 12/2005 | Harvey et al. |
| 2006/0134729 | A1* | 6/2006 | Besson-Faure .......... C12Q 1/04 435/34 |
| 2006/0172379 | A1 | 8/2006 | Teter et al. |
| 2007/0099267 | A1 | 5/2007 | Harvey et al. |
| 2009/0005264 | A1 | 1/2009 | Rakestraw et al. |
| 2009/0123921 | A1 | 5/2009 | Georgiou et al. |
| 2009/0136936 | A1 | 5/2009 | Georgiou et al. |
| 2009/0234101 | A1 | 9/2009 | Ladner et al. |

FOREIGN PATENT DOCUMENTS

| AU | 2003304195 B8    | 9/2005 |
| AU | 2008243161 A1    | 12/2008 |
| EP | 1 279 731 A1     | 1/2003 |
| EP | 1 820 858 A1     | 8/2007 |
| JP | 2006-507010 A    | 3/2006 |
| JP | 2007-121282 A    | 5/2007 |
| WO | WO 92/15677      | 9/1992 |
| WO | WO 02/034886 A2  | 5/2002 |
| WO | WO 2005/019409 A2 | 3/2005 |
| WO | WO 2005/074725 A1 | 8/2005 |
| WO | WO 2005/095988 A2 | 10/2005 |
| WO | WO 2005/103074 A2 | 11/2005 |
| WO | WO 2008/067547 A2 | 6/2008 |
| WO | WO 2008/074724 A1 | 6/2008 |
| WO | WO 2008/137475 A2 | 11/2008 |

OTHER PUBLICATIONS

Canovas et al., Enzyme and Microbial Technology, 2005, 37:300-308.*
Fuchs, P. et al., "Separation of *E. coli* Expressing Function Cell-Wall Bound Antibody Fragments by FACS" *Immunotechnology* (Jun. 1, 1996) pp. 97-102, vol. 2.
Georgiou, G. et al., "Display of β-lactamase on the *Escherichia coli* Surface: outer membrane phenotypes conferred by Lpp'-OmpA'-β-lactamase fusions" *Protein Engineering* (Jan. 1, 1996) pp. 239-247, vol. 9, No. 2.
Skerlavaj, B. et al., "Rapid Membrane Permeabilization and Inhibition of Vital Functions of Gram-Negative Bacteria by Bactenecins" *Infection and Immunity* (Nov. 1, 1990) pp. 3724-3730, vol. 58, No. 11.
Supplementary European Search Report dated Nov. 12, 2013 issued in European Application No. EP 10838401.7.

(Continued)

*Primary Examiner* — Jennifer Pitrak McDonald
*Assistant Examiner* — Qing Xu
(74) *Attorney, Agent, or Firm* — Scully Scott Murphy & Presser

(57) ABSTRACT

The present invention relates to methods for screening a polypeptide for desired activity against a target molecule In particular, the present invention relates to methods for screening a polypeptide for desired activity against a target molecule by expressing the polypeptide in a bacterial cell and permeabilizing the cell.

Figure 1:
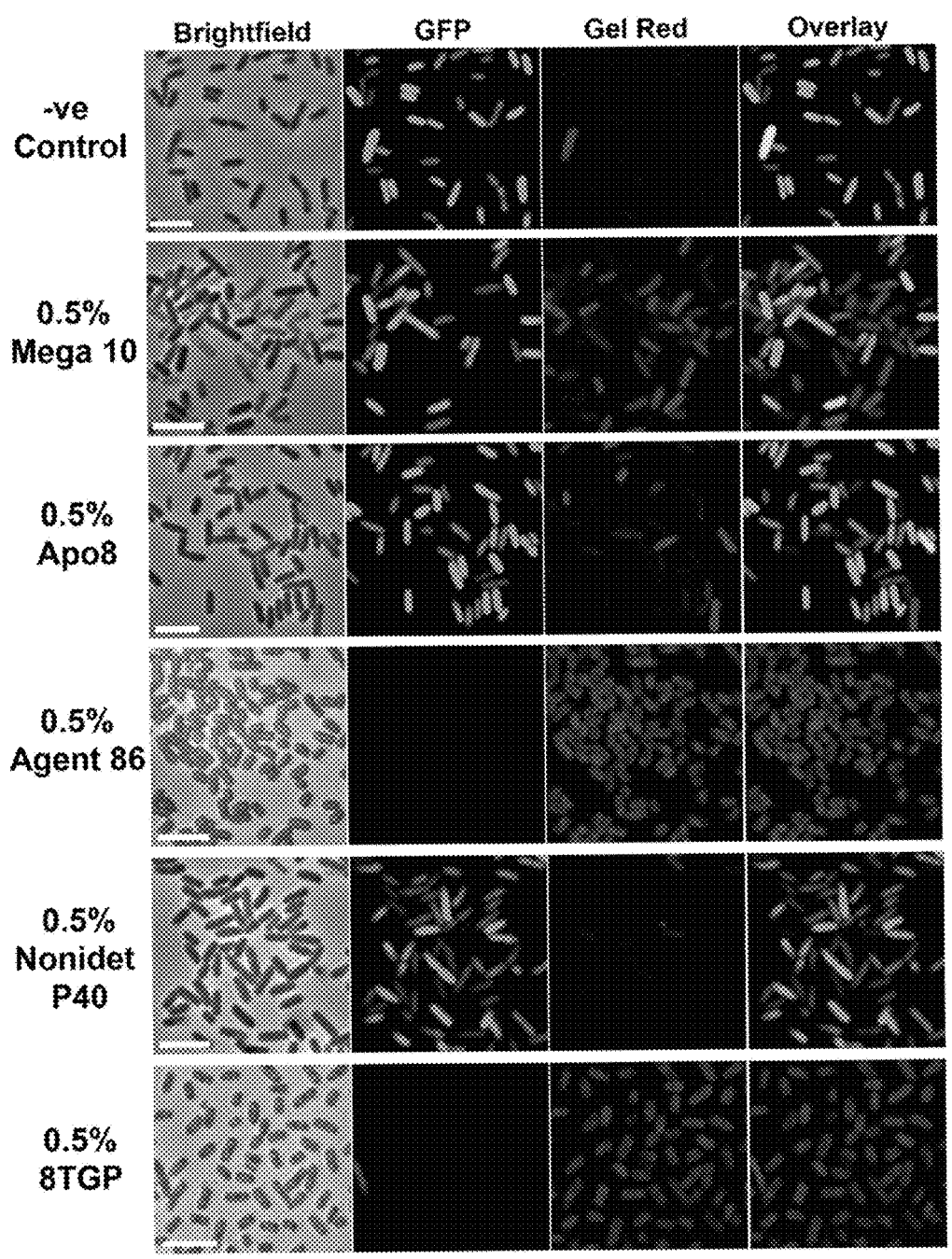

7 Claims, 21 Drawing Sheets
Specification includes a Sequence Listing.

(56) References Cited

OTHER PUBLICATIONS

Aharoni A. et al., "High-Throughput Screening of Enzyme Libraries: Thiolactonases Evolved by Fluorescence-Activated Sorting of Single Cells in Emulsion Compartments", *Chemistry & Biology* 12:1281-1289 (Dec. 2005).
Becker S. et al., "Ultra-High-Throughput Screening Based on Cell-Surface Display and Fluorescence-Activated Cell Sorting for the Identification of Novel Biocatalysts", *Current Opinion in Biotechnology* 15:323-329 (2004).
Bershtein S. et al., "Advances in Laboratory Evolution of Enzymes", *Current Opinion in Chemical Biology* 12:151-158 (2008).
Briers Y. et al., "The High-Affinity Peptidoglycan Binding Domain of *Pseudomonas* Phage Endolysin KZ144", *Biochemical and Biophysical Research Communications* 383:187-191 (2009).
Chen I. et al., "ComE, a Competence Protein from *Neisseria gonorrhoeae* With DNA-Binding Activity", *Journal of Bacteriology* 183(10):3160-3168 (May 2001).
Daugherty P.S. et al., "Flow Cytometric Screening of Cell-Based Libraries", *Journal of Immunological Methods* 243:211-227 (2000).
Farinas E.T., "Fluorescence Activated Cell Sorting for Enzymatic Activity", *Combinatorial Chemistry & High Throughput Screening* 9:321-328 (2006).
George R.A. et al., "An Analysis of Protein Domain Linkers: Their Classification and Role in Protein Folding", *Protein Engineering* 15(11):871-879 (2003).
Kenrick S. et al., "Flow Cytometric Sorting of Bacterial Surface-Displayed Libraries", *Molecular and Cellular Probes* 42(4):4.6.1-4.6.27 (Oct. 2007).
Lutz S. et al., "Novel Methods for Directed Evolution of Enzymes: Quality, Not Quantity", *Current Opinion in Biotechnology* 15:291-297 (2004).
Magnet S. et al., "Identification of the $_{L,D}$-Transpeptidases Responsible for Attachment of the Braun Lipoprotein to *Escherichia coli* Peptidoglycan", *Journal of Bacteriology* 189(10):3927-3931 (May 2007).
Miller O.J. et al., "Directed Evolution by In Vitro Compartmentalization", *Nature Methods* 3(7):561-570 (Jul. 2006).
Parsons L.M. et al., "Peptidoglycan Recognition by Pal, an Outer Membrane Lipoprotein", *Biochemistry* 45:2122-2128 (2006).
Schaefer J.V. et al., "Construction of scFv Fragments from Hybridoma or Spleen Cells by PCR Assembly", *Antibody Engineering* 1:21-44 (2010).
Smith G.P., "Filamentous Fusion Phage: Novel Expression Vectors that Display Cloned Antigens on the Virion Surface", *Science* 228:1315-1317 (Jun. 1985).
Tracewell C.A. et al., "Directed Enzyme Evolution: Climbing Fitness Peaks One Amino Acid at a Time", *Current Opinion in Chemical Biology* 13(1):3-9 (Feb. 2009).
International Search Report dated Feb. 23, 2011 received from the Australian Patent Office from related International Application No. PCT/AU2010/001702.
Jevsevar, Simona, et al., "Production of Nonclassical Inclusion Bodies from Which Correctly Folded Protein Can be Extracted", Biotechnol. Prog. 2005, 21, pp. 632-639.
Peternel, Spela, et al., Engineering Inclusion Bodies for Non-Denaturing Extraction of Functional Proteins, Microbial Cell Factories, 2008, 7:34 pp. 1-9.
Patent Examination Report No. 2 issued in Australian Patent Application No. 2012276282 dated Aug. 25, 2015.
Patent Examination Report No. 1 issued in Australian Patent Application No. 2010336004 dated Dec. 5, 2014.
Patent Examination Report No. 1 issued in Australian Patent Application No. 2012276282 dated Jun. 19, 2014.
Barondess, J. J., et al., "bor Gene of Phage λ, Involved in Serum Resistance, Encodes a Widely Conserved Outer Membrane Lipoprotein" Journal of Bacteriology 177(5):1247-1253 (1995).
Bertani, L. E., "Abortive Induction of Bacteriophage P2" Virology 36:87-103 (1968).

Bradley, C., et al., "Isolation of Phage P2-186 Intervarietal Hybrids and 186 Insertion Mutants" Molec. gen. Genet. 140:123-135 (1975).
Briani, F., et al., "The Plasmid Status of Satellite Bacteriophage P4" Plasmid 45:1-17 (2001).
Chang, J. R., et al., "Incorporation of scaffolding protein gpO in bacteriophages P2 and P4" Virology 370:352-361 ((2008).
Cherepanov, P. P., et al. "Gene disruption in *Escherichia coli*: Tc R and Km R cassettes with the option of Flp-catalyzed excision of the antibiotic-resistance determinant" Gene 158:9-14 (1995).
Notification of First Office Action issued in Chinese Patent Application No. 201280041236.9 dated Nov. 4, 2014 (in English and Chinese).
Dai, M., et al., "Using T7 phage display to select GFP-based binders" Protein Engineering, Design & Selection 21 (7):413-424 (2008).
Communication pursuant to Article 94(3) issued in European Patent Application No. 10 838 104.7-1404 dated Oct. 7, 2015.
Gupta, A., "High-density Functional Display of Proteins on Bacteriophage Lambda" J. Mol. Biol. 334:241-254 (2003).
Hamilton, C. M., et al., "New Method for Generating Deletions and Gene Replacements in *Escherichia coli*" Journal of Bacteriology 171(9):4617-4622 (1989).
Notice of Reasons for Rejection issued in Japanese Patent Application No. 2012-545011 dated Mar. 10, 2015 (English translation only).
Kahn, M. L., et al., "Bacteriophage P2 and P4" Methods in Enzymology 204:264-280 (1991).
Karasawa S., et al., "A Green-emitting Fluorescent Protein from Galaxeidae Coral and Its Monomeric Version for Use in Fluorescent Labeling*" The Journal of Biological Chemistry 278(36):34167-34171 (2003).
Kim, K, et al., "Isolation and Characterization of the Smallest Bacteriophage P4 Derivatives Packaged into P4-Size Head in Bacteriophage P2-P4 System" The Journal of Microbiology 44(5):530-536 (2006).
King, S. R., et al., "Nucleotide Sequence Analysis of in vivo Recombinants Between Bacteriophage λ DNA and pBR322" Mol Gen Genet 186:548-557 (1982).
Levy R. et al., "Isolation of trans-acting genes that enhance soluble expression of scFv antibodies in the *E. coli* cytoplasm by lambda phage display" Journal of Immunological Methods 321:164-173 (2007).
Li, Q., et al., "Assembly of the Small Outer Capsid Protein, Soc, on Bacteriophage T4: A Novel System for High Density Display of Multiple Large Anthrax Toxins and Foreign Proteins on Phage Capsid" J. Mol. Biol. 370:1006-1019 (2007).
Lindqvist, B. H., "Mechanisms of Genome Propagation and Helper Exploitation by Satellite Phage P4" Microbiological Reviews 57(3):683-702 (1993).
Lindqvist, B. H., et al., "Peptide presentation by bacteriophage P4" FEMS Microbiology Reviews 17:33-39 (1995).
Ljungquist, E., et al., "DNA sequences of the repressor gene and operator region of bacteriophage P2" Proc. Natl. Acad. Sci. 81:3988-3992 (1984).
Maruyama, I. N., et al., "λfoo: A λ phage vector for the expression of foreign proteins" Proc. Nadl. Acad. Sci. USA 91:8273-8277 (1994).
Mikawa, Y. G., et al., "Surface Display of Proteins on Bacteriophage λ Heads" J. Mol. Biol. 262:21-30 (1996).
Montigiani, S., et al., "Alanine Substitutions in Calmodulin-binding Peptides Result in Unexpected Affinity Enhancement" J. Mol. Biol. 258:6-13 (1996).
Santini, C., et al., "Efficient Display of an HCV cDNA Expression Library as C-terminal Fusion to the Capsid Protein D of Bacteriophage Lambda" J. Mol. Biol. 282:125-135 (1998).
Sasaki, I., et al., "Growth abnormalities in Hfr Derivatives of *Escherichia coli* Strain c" J. gen. Microbiol. 40:365-376 (1965).
Sauer, B., et al., "Interaction of Satellite Phage P4 with Phage 186 Helper" Virology 116 528-534 (1982).
Sternberg, N., et al., "Display of peptides and proteins on the surface of bacteriophage λ" Proc. Natl. Acad. Sci. USA 92:1609-1613 (1995).

(56) References Cited

OTHER PUBLICATIONS

Vaccaro, P., et al., "Efficient display of scFv antibodies on bacteriophage lambda" Journal of Immunological Methods 310:149-158 (2006).
Wiman, M., et al., "Genetic Map of *Escherichia coil* Strain C" Molec. Gen. Genetics 107:1-31 (1970).
Woods, W. H., et al., "Prophage Induction of Noninducible Coliphage 186" Journal of Virology 14 (6):1349-1356 (1974).
Yankovsky, N. K, et al., "Phasmids as effective and simple tools for construction and analysis of gene libraries" Gene 81:203-210 (1989).
Younghusband, H. B., et al., "Characterization of the DNA from Bacteriophage P2-186 Hybrids and Physical Mapping of the 186 Chromosome" Molec. gen. Genet. 140:101-110 (1975).
Ziermann, R., et al., "Functions Involved in Bacteriophage P2-Induced Host Cell Lysis and Identification of a New Tail Gene" Journal of Bacteriology 176(16):4974-4984 (1994).
Breeuwer, P., et al. "Assessment of the membrane potential, intracellular pH and respiration of bacteria employing fluorescence techniques" Molecular Microbial Ecology Manual, Second Edition MMEM-8.01/1563-MMEM-8.01/1579 (2004).
Chen, W., et al. "A simple and rapid method for the preparation of gram-negative bacterial genomic DNA" Nucleic Acids Research 21(9):2260 (1993).
De Leu, F., et al., "Lac as a marker gene to track microbes in the environment" Molecular Microbial Ecology Manual, Second Edition MMEM-6.01/1187-MMEM-6.01/1199 (2004).
Devereus, R., et al., "Amplification of ribosomal RNA sequences" Molecular Microbial Ecology Manual, Second Edition MMEM-3.01/509-MMEM-3.01/521 (2004).
Goldenberger, D., et al. "A Simple "Universal" DNA Extration Procedure Using SDS and Proteinase K is Compatible with Direct PCR Amplification" Genome Res 4:368-370 (1995).
Harvey, B. R., et al. "Anchored periplasmic expression, a versatile technology for the isolation of high-affinity antibodies from *Escherichia coli*-espressed libraries" PNAS 101(25):9193-9198 (2004).
Insam, H., et al. "Use of Biolog® for the Community Level Physiological Profiling (CLPP) of environment samples" Molecular Microbial Ecology Manual, Second Edition MMEM-4.01/853-MMEM-4.01/860 (2004).
Moore, E., et al., "Simplified protocols for the preparation of genomic DNA from bacterial cultures" Molecular Microbial Ecology Manual, Second Edition MMEM-1.01/3-MMEM-1.01/17 (2004).
Paul, J. H. et al., "Natural transformation in aquatic environments" Molecular Microbial Ecology Manual, Second Edition MMEM-5.01/1047-MMEM-5.01/1068 (2004).
Torsvik, V., "Quantification of nucleic acids" Molecular Microbial Ecology Manual, Second Edition MMEM-2.01/215-MMEM-2.01/222 (2004).
Messens, J. et al., "Pathways of disulfide bond formation in *Escherichia coli*", The International Journal of Biochemistry & Cell Biology, (2006), vol. 38, pp. 1050-1062.
Begley, M. et al., "The interaction between bacteria and bile", FEMS Microbiology Reviews, (2005), vol. 29, pp. 625-651.
Liu, T., "Derepression of Prophage P2 by Satellite Phage P4: Cloning of the P4 ε Gene and Identification of Its Product" Journal of Virology 71(6):4502-4508 (1997).
Virta, M. et al., "Real-time measurement of cell permeablization with low-molecular-weight membranolytic agents", Journal of Antimicrobial Chemotherapy, (1995), vol. 36, pp. 303-315.

\* cited by examiner

PROTEIN DISPLAY

FIELD OF THE INVENTION

The present invention relates to methods for screening a polypeptide for desired activity against a target molecule. In particular, the present invention relates to methods for screening a polypeptide for desired activity against a target molecule by expressing the polypeptide in a bacterial cell and permeabilising the cell.

BACKGROUND OF THE INVENTION

The earliest method of protein display is phage display (Smith, 1985), in which the protein of interest is fused to one of the outer-coat proteins of the phage where it may be present along with wild-type copies of the protein. For example, a display platform based on the M13 filamentous phage using fusions to the pIII protein.

Other display methods include 'in vitro' display methods where the protein is expressed using a cellular translation extract, and the coupling between the protein and the coding nucleic acid is achieved through physical linkage (e.g. ribosome display, mRNA display) or through attachment to a common scaffold or encapsulation within a membrane, such as in in vitro compartmentalization (IVC) where the mRNA is translated within a micelle suspension that may also include a microbead (magnetic or sepharose) capture system for both mRNA and protein.

Another method of protein display is microbial surface display which involves the targeted location of expressed proteins to the exterior of a microbial cell, either gram-negative, gram-positive eubacteria or yeast. The proteins are fused to anchor domains that attach them to the cell surface. The anchor domains may have motifs dictating lipidation or covalent attachment to the cell wall, or they may be a fusion to an integral membrane protein within an exposed loop region. Due to the scalability of production, microbial surface display may not only be used for screening for improved protein variants from a diverse library, but may also be used to present antigens for vaccination or as a cellular-scaffold for enzymes for industrial biotechnology.

Protein display methods are commonly applied to the evolution of affinity proteins, such as antibodies. Single molecule display methods are historically the most popular, but they suffer from high background and low resolution between affinity scales. Proteins identified by surface display in yeast or by phage systems are usually reformatted for expression in the *E. coli* periplasm, even though periplasmic yields are often extremely poor comparable to expression in the cytoplasm. When antibodies are expressed in the cytoplasm at high yield, however, in almost every instance they form insoluble inclusion bodies that must be laboriously refolded and tested for activity.

Thus, there remains a need for methods of protein display, particularly for the screening of affinity protein display libraries and enzyme libraries.

SUMMARY OF THE INVENTION

The present inventors have developed a method of protein display which allows for screening of a polypeptide for a desired activity against a target molecule in a permeabilised bacterial cell. The polypeptide is either retained within, or bound to, the permeabilised bacterial cell.

Accordingly, the present invention provides a method of screening a polypeptide for a desired activity against a target molecule, the method comprising:

a) culturing a bacterial cell comprising a polynucleotide encoding the polypeptide such that the polypeptide is produced, b) permeabilising the bacterial cell, wherein the polypeptide and polynucleotide encoding the polypeptide are retained inside the permeabilised bacterial cell, c) contacting the permeabilised bacterial cell with the target molecule such that it diffuses into the permeabilised bacterial cell, and d) screening the polypeptide for the desired activity.

The present invention further provides a method of screening a polypeptide for a desired activity against a target molecule, the method comprising:

a) culturing a bacterial cell comprising a polynucleotide encoding the polypeptide such that the polypeptide is produced and attaches to the bacterial cell wall, b) permeabilising the bacterial cell, wherein the polynucleotide encoding the polypeptide is retained inside the permeabilised bacterial cell, c) contacting the permeabilised bacterial cell with the target molecule, and d) screening the polypeptide for the desired activity.

In one embodiment, step d) comprises:

i) determining if the polypeptide binds, and/or the extent of binding to, the target molecule, and/or ii) determining if the polypeptide enzymatically modifies, and/or the rate of enzymatic modification of, the target molecule.

The bacterial cell may be permeabilised with any suitable agent which solubilises the cellular membranes, but which retains the integrity of the bacterial cell wall. Such agents include detergents and organic solvents. In one embodiment, the bacterial cell is permeabilised with a detergent, for example a non-ionic detergent.

While the methods of the invention may be performed in any suitable Gram negative or Gram positive bacterial cell, preferably the bacterial cell is a Gram negative bacterial cell.

Thus, the present invention further provides a method of screening a polypeptide for a desired activity against a target molecule, the method comprising:

a) culturing a Gram negative bacterial cell comprising a polynucleotide encoding the polypeptide such that the polypeptide is produced, b) permeabilising the cellular membranes of the bacterial cell, wherein the polypeptide and polynucleotide encoding the polypeptide are retained inside the permeabilised bacterial cell, c) contacting the permeabilised bacterial cell with the target molecule such that it diffuses into the permeabilised bacterial cell, and d) screening the polypeptide for the desired activity.

The present invention further provides a method of screening a polypeptide for a desired activity against a target molecule, the method comprising:

a) culturing a Gram negative bacterial cell comprising a polynucleotide encoding the polypeptide such that the polypeptide is produced and attaches to the bacterial cell wall, b) permeabilising the cellular membranes of the bacterial cell, wherein the polynucleotide encoding the polypeptide is retained inside the permeabilised bacterial cell, c) contacting the permeabilised bacterial cell with the target molecule, and d) screening the polypeptide for the desired activity.

In one embodiment, the polypeptide is associated with a least a second polypeptide to form a protein complex that is retained inside the permeabilised bacterial cell and/or attached to the bacterial cell wall. The polypeptide may be, for example, indirectly associated with the second polypeptide such as by non-covalent or covalent bonds, or the polypeptide may be associated directly with the second polypeptide, for example such as a fusion protein.

Thus, in one embodiment, the polypeptide is fused to the second polypeptide, or a subunit thereof.

In the methods of the invention, the second polypeptide can be selected from:

i) a polypeptide having a molecular size such that the protein complex is retained inside the permeabilised bacterial cell wall;

ii) a DNA-binding protein; and/or iii) a bacterial cell wall-binding protein.

In one embodiment, the molecular weight of the protein complex is at least about 120 kDa.

In another embodiment, the second polypeptide forms multimers inside the permeabilised bacterial cell. The multimer may be, for example, a dimer, trimer, tetramer, pentamer, hexamer or higher order multimer. In one embodiment, the multimer is a tetramer.

In one particular embodiment, the second polypeptide is selected from RhnA, β-galactosidase, BetB, G5K, GshB, and YdcW.

Any DNA binding protein may be used in the methods of the invention in order to link the polypeptide being screened for a desired activity to the bacterial host cell DNA. In one embodiment, the DNA binding protein is ComE.

Alternatively or in addition, the polypeptide may be associated with a bacterial cell wall-binding protein, wherein the bacterial cell wall-binding protein is selected from a peptidoglycan-binding protein, and a lipoprotein or fragment thereof capable of binding to the cell wall.

In one embodiment, the bacterial cell wall binding protein is a peptidoglycan binding protein selected from KzPG, PAL, OmpA, YiaD, YfiB and MotB.

While the polypeptide may be attached either non-covalently or covalently to the bacterial cell wall, in one embodiment the polypeptide is covalently attached to the bacterial cell wall.

In another embodiment, the lipoprotein capable of binding to the cell wall is a lipoprotein lacking a functional N-terminal signal sequence necessary for outer membrane attachment.

In one particular embodiment, the lipoprotein is *E. coli* LPP.

In one embodiment of the methods of the invention, the non-ionic detergent is selected from Decanoyl-N-methylglucamide (Mega10), demithyloctylphosphine oxide (Apo8), n-octyl-β-D-thioglucopyranoside (8TGP), and a mixture of Decanoyl-N-methylglucamide (Mega10) and demithyloctylphosphine oxide (Apo8).

In one particular embodiment, permeabilising the bacterial cell is performed in a solution selected from:

i) about 0.5% n-octyl-β-D-thioglucopyranoside (8TGP) in LB, and ii) about 0.5% Decanoyl-N-methylglucamide (Mega10) and about 0.5% demithyloctylphosphine oxide (Apo8) in LB.

In another embodiment of the methods of the invention, step b) comprises selectively permeabilising the bacterial cell, whereby the outer membrane of the bacterial cell is permeablised to a greater extent than the inner membrane of the bacterial cell.

In an embodiment, the bacterial cell is selectively permeabilised with a detergent selected from demithyloctylphosphine oxide (Apo8) and/or polysorbate 20 (Tween20).

In one embodiment, selectively permeabilising the bacterial cell is performed in a solution comprising the detergent at about 0.2%.

In another embodiment, selectively permeabilising the bacterial cell is performed in a solution comprising EDTA or $Ca^{2+}$.

In another embodiment, the method further comprises isolating DNA comprising the polynucleotide encoding the polypeptide from the permeabilised bacterial cell.

The DNA which is isolated from the bacterial cell may be genomic DNA and/or episomal DNA. The episomal DNA may be, for example, a plasmid or a cosmid.

In one embodiment, the polynucleotide is an exogenous polynucleotide.

In another embodiment, the molecular weight of the target molecule is less than about 120 kDa.

The present invention further provides a method for identifying a polypeptide with a desired activity, the method comprising:

a) screening a library of polypeptides using a method of the invention; and b) selecting one or more polypeptides with the desired activity.

In one embodiment, the method further comprises c) isolating DNA comprising the polynucleotide encoding the polypeptide from the bacterial cell.

In another embodiment, the method further comprises d) determining the sequence of the polynucleotide encoding the polypeptide.

In an embodiment, the library of polypeptides is encoded by polynucleotides obtained from a cell, tissue, organ or organism.

In another embodiment, the library of polypeptides is encoded by polynucleotides obtained by mutating one or more parental polynucleotides.

In an embodiment, the polypeptide is an antibody or enzyme.

In one particular embodiment, the antibody is a single-chain variable fragment (scFV).

In another embodiment, the polypeptide is an enzyme and the target molecule is linked to the permeabilised bacterial cell. To achieve linkage of the target molecule to the permeabilised bacterial cell, the target molecule may be linked either directly or indirectly to the bacterial cell. To indirectly link the target molecule to the permeabilised bacterial cell, the target molecule may be, for example, linked to a bacterial cell wall-binding protein.

In another embodiment, the polypeptide is a binding protein other than an antibody. For example the polypeptide may be a binding protein including, but not limited to, a lipocalin, a fibronectin type III domain (FN3), ubiquitin, or γ-B-crystallin.

In one embodiment of the methods of the invention, the polypeptide comprises a domain selected from any one of I27, RL6, KzPG, SNAP, and/or DBP. In one particular embodiment, the polypeptide comprises the domains I27, RL6, KzPG, SNAP, and DBP.

In another embodiment of the methods of the invention, the polypeptide comprises an amino acid sequence at least 80%, preferably at least 90%, more preferably at least 95%, more preferably 100% identical to SEQ ID NO:13.

The present invention further provides a permeabilised bacterial cell comprising an exogenous polypeptide associated with a second polypeptide to form a protein complex that is retained inside the permeabilised bacterial cell.

The present invention further provides a Gram negative bacterial cell comprising permeabilised cellular membranes, wherein the bacterial cell comprises an exogenous polypeptide associated with a second polypeptide to form a protein complex that is retained inside the permeabilised bacterial cell.

The present invention further provides a permeabilised bacterial cell comprising an exogenous polypeptide attached to the bacterial cell wall.

The present invention further provides a Gram negative bacterial cell comprising permeabilised cellular membranes, wherein the bacterial cell comprises an exogenous polypeptide attached to the bacterial cell wall.

The present invention further provides a kit comprising:
a) a vector comprising
  i) a site for inserting into the vector a polynucleotide encoding a first polypeptide, and
  ii) an open reading frame encoding a second polypeptide which associates with the first polypeptide to form a protein complex that is retained inside a permeabilised bacterial cell, and
b) an agent capable of permeabilising a bacterial cell.

The present invention further provides a kit comprising:
a) a vector comprising
  i) a site for inserting into the vector a polynucleotide encoding a first polypeptide, and
  ii) an open reading frame encoding a second polypeptide which associates with the first polypeptide to form a protein complex that is attached to the bacterial cell wall, and
b) an agent capable of permeabilising a bacterial cell.

In one embodiment, the site and open reading frame are positioned such that the first polypeptide and the second polypeptide, or subunit thereof, are expressed as a fusion protein.

In another embodiment, the agent capable of permeabilising a bacterial cell is a detergent.

In yet another embodiment, the detergent is a non-ionic detergent selected from Decanoyl-N-methylglucamide (Mega10), demithyloctylphosphine oxide (Apo8), n-octyl-β-D-thioglucopyranoside (8TGP), and a mixture of Decanoyl-N-methylglucamide (Mega10) and demithyloctylphosphine oxide (Apo8).

In one embodiment, the kit further comprises bacterial cells.

Preferably, the bacterial cells are Gram negative. For example, the bacterial cells may be *E. coli*.

The present invention further provides a kit comprising:
a) a vector comprising
  i) a site for inserting into the vector a polynucleotide encoding a first polypeptide, and
  ii) an open reading frame encoding a second polypeptide which associates with the first polypeptide to form a protein complex that is retained inside a Gram negative bacterial cell comprising permeabilised cellular membranes, and
b) an agent capable of permeabilising a Gram negative bacterial cell.

The present invention further provides a kit comprising:
a) a vector comprising
  i) a site for inserting into the vector a polynucleotide encoding a first polypeptide, and
  ii) an open reading frame encoding a second polypeptide which associates with the first polypeptide to form a protein complex that attaches to a Gram negative bacterial cell wall, wherein the Gram negative bacterial cell comprises permeabilised cellular membranes, and
b) an agent capable of permeabilising a Gram negative bacterial cell.

The present invention further provides polypeptide comprising an amino acid sequence at least 80%, preferably at least 90%, more preferably at least 95%, more preferably 100% identical to SEQ ID NO:13.

The present invention further provides a polynucleotide comprising a nucleotide sequence at least 80%, preferably at least 90%, more preferably at least 95%, more preferably 100% identical to SEQ ID NO:14 or SEQ NO:15.

The present invention further provides a vector comprising the polynucleotide sequence of the invention.

The present invention further provides a polypeptide spacer comprising an amino acid sequence at least 90%, more preferably 100% identical to any one of SEQ ID NOs:6 to 12 or 16.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. Detergent permeabilisation of *E. coli* cells. *E. coli* cells expressing GFP were treated with detergents to determine the effectiveness of membrane permeabilisation. Cells were viewed by either brightfield (first column) or fluorescence microscopy (second and third columns). Permeabilisation was effective if GFP (green, column 2) was released from the cell concurrent with uptake of the membrane-impermeable DNA-binding dye, Gel Red (third column). Detergents 8TGP (0.5%) and 0.5% Mega10/0.5% Apo 8 ('Agent86') were found to be most effective in permeabilising *E. coli* cells.

Figure 2:
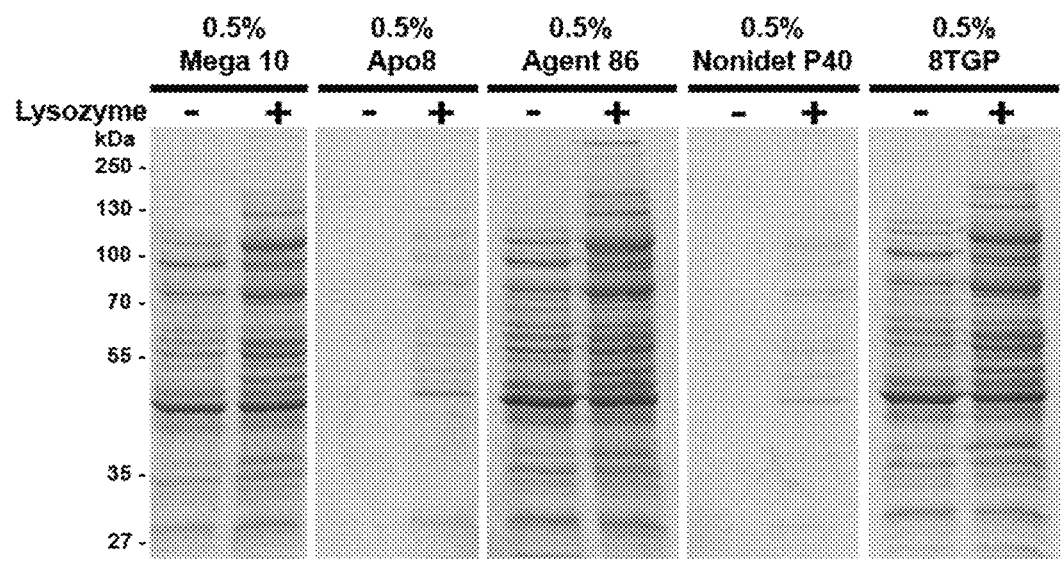

FIG. 2. SDS-PAGE of detergent supernatants. The supernatant of the detergent permeabilisation of *E. coli* cells shown in FIG. 1 were loaded onto a 9% SDS-PAGE to qualitatively judge protein release by the detergents (first lane). To demonstrate retention of a subset of cellular proteins by the cell wall capsule in detergent permeabilised cells, a sample of detergent permeabilised cells was treated with lysozyme (2 mg/mL) to hydrolyse the cell wall (second lane).

Figure 3:
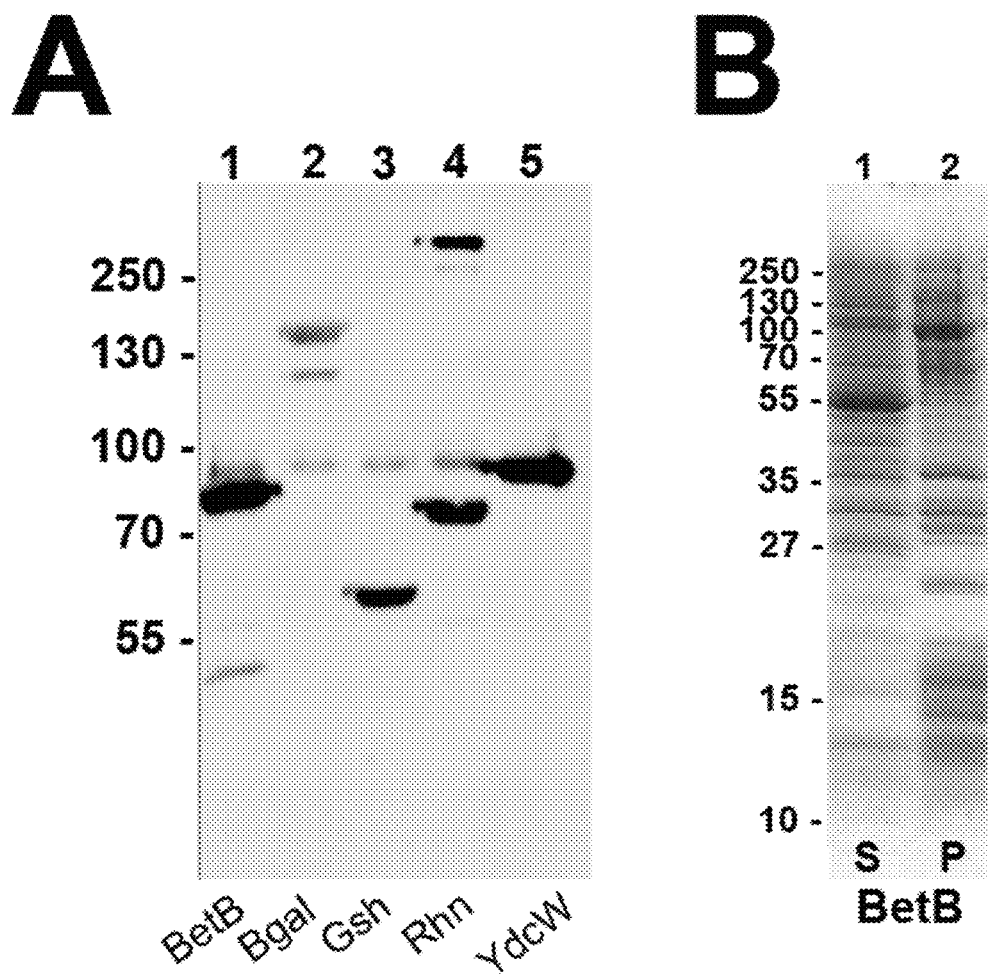

FIG. 3. Tetrameric-fusion protein expression. (A) Expression of His 6::SNAP::tetramer fusion proteins in *E. coli* was examined by Western blot using an αHis antibody probed against total cellular protein. A high-molecular weight band of >250 kD was observed in the RhnA tetramer fusion (lane 4), in addition to a band of the expected molecular weight, which is a presumptive SDS-resistant form of the complex that migrated as a tetramer. (B) The BetB tetrameric fusion protein extract was separated into the detergent-soluble and -insoluble (cell capsule pellet) extracts, and examined by SDS-PAGE.

Figure 4:
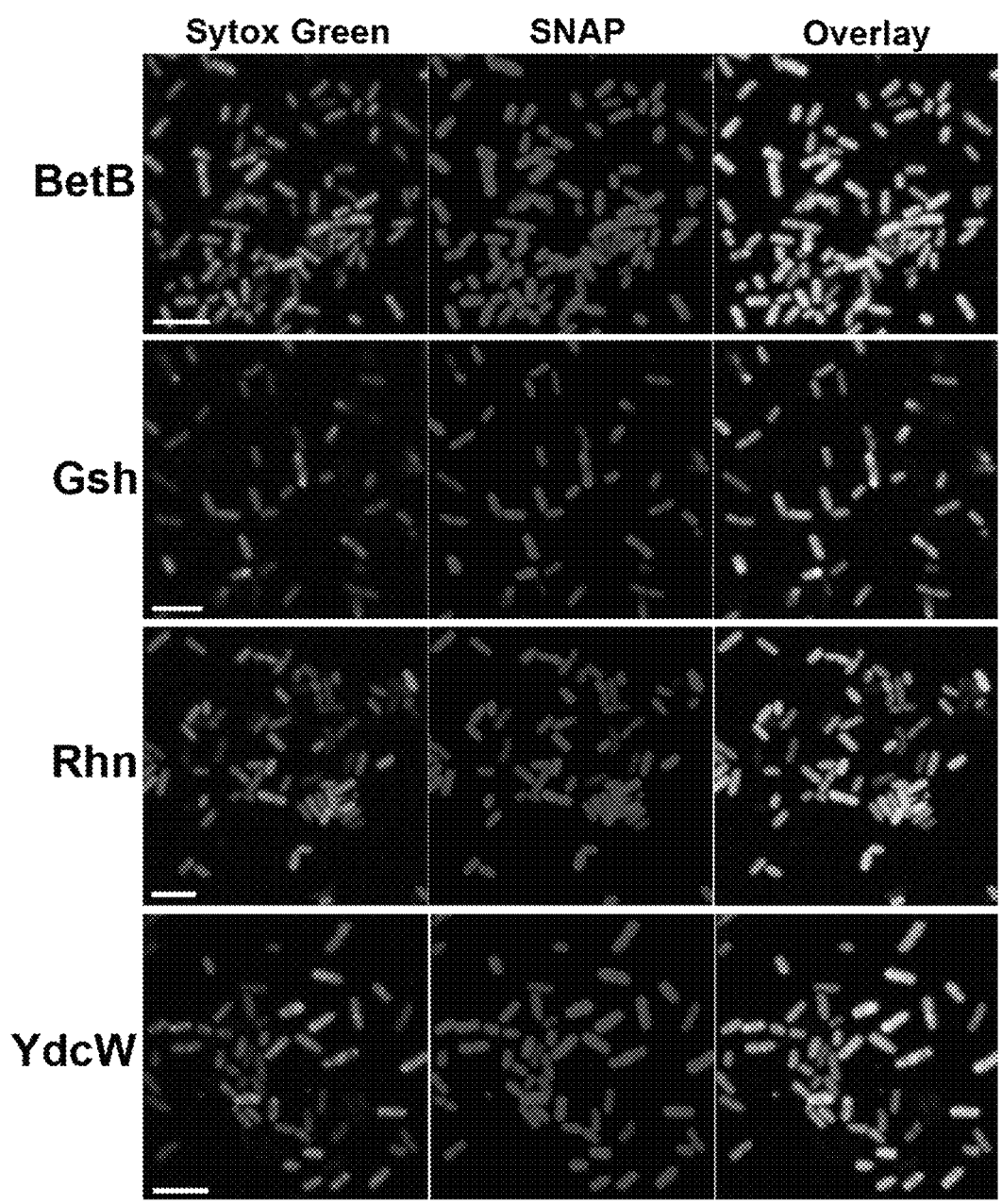

FIG. 4. SNAP labeling of tetramer-fusion proteins. The His 6::SNAP::tetramer fusion proteins were expressed in *E.* coli, and the cells were permeabilised with 8TGP, as described by Example 1. Expression of the fusion protein was detected by fluorescence microscopy of permeabilised cells labeled with the membrane-impermeable SNAP ligand BG-547 (second column), as described in Example 3. Cellular DNA was labeled with the membrane-permeable dye, Sytox Green (first column). The overlay of the SNAP and Sytox Green signal is presented in the third column.

Figure 5:
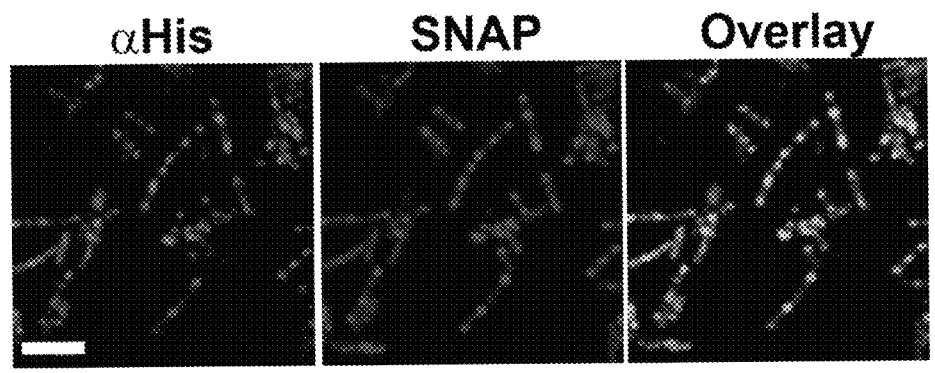

FIG. 5. αHis antibody labeling of His6::SNAP::BetB tetramer in permeabilised cells. Fluorescence microscopy of permeabilised cells expressing the His 6::SNAP::BetB tetramer probed with an αHis antibody (first panel), as described in Example 3. Cells were labeled with the SNAP ligand BG-547 (second panel). The co-localisation of both αHis and SNAP (third panel) indicates that the αHis antibody penetrated through the cell wall of permeabilised cells.

Figure 6:
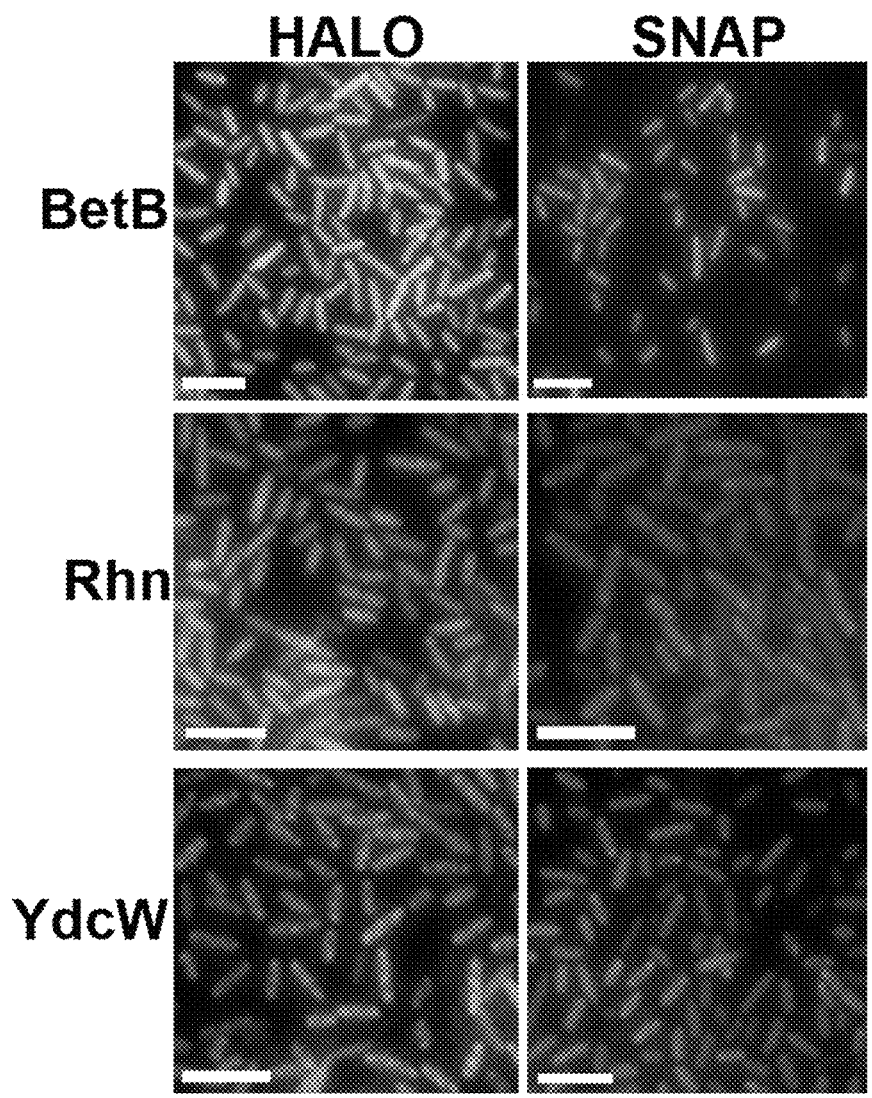

FIG. 6. BetB, RhnA and YdcW tetramer fusions with HALO and SNAP expression reporters. The BetB, RhnA and YdcW tetramers were separately fused to the expression reporters, HALO and SNAP. Cells expressing the fusion protein were permeabilised and the host DNA was labeled with Gel Red and the fusion protein was detected using the fluorescent ligands for HALO (G1001) and SNAP (BG-488).

Figure 7:
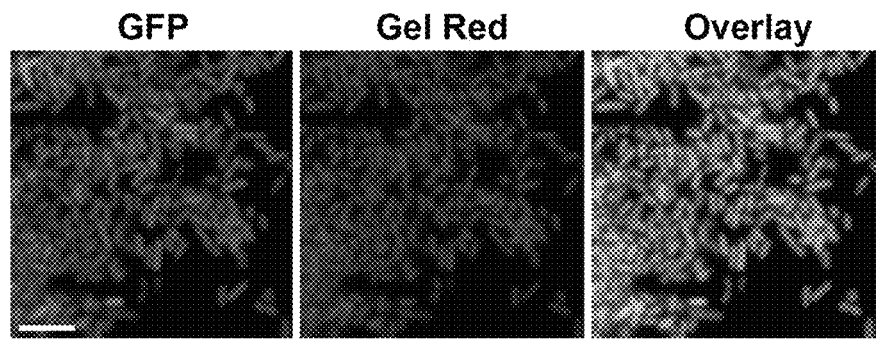

FIG. 7. Expression of the GFP5::DNA Binding Protein (DBP) fusion. The non-specific, high-affinity, DNA binding protein, ComE, from *N. gonorrhoeae* was fused to the C-terminus of GFP5 and expressed in *E. coli*. Cells were permeabilised and viewed by fluorescence microscopy for GFP (first panel) and Gel Red (second panel). Co-localisation (third panel) of the fluorescence indicates that both the fusion protein and host DNA were retained within the permeabilised cell capsule.

Figure 8:
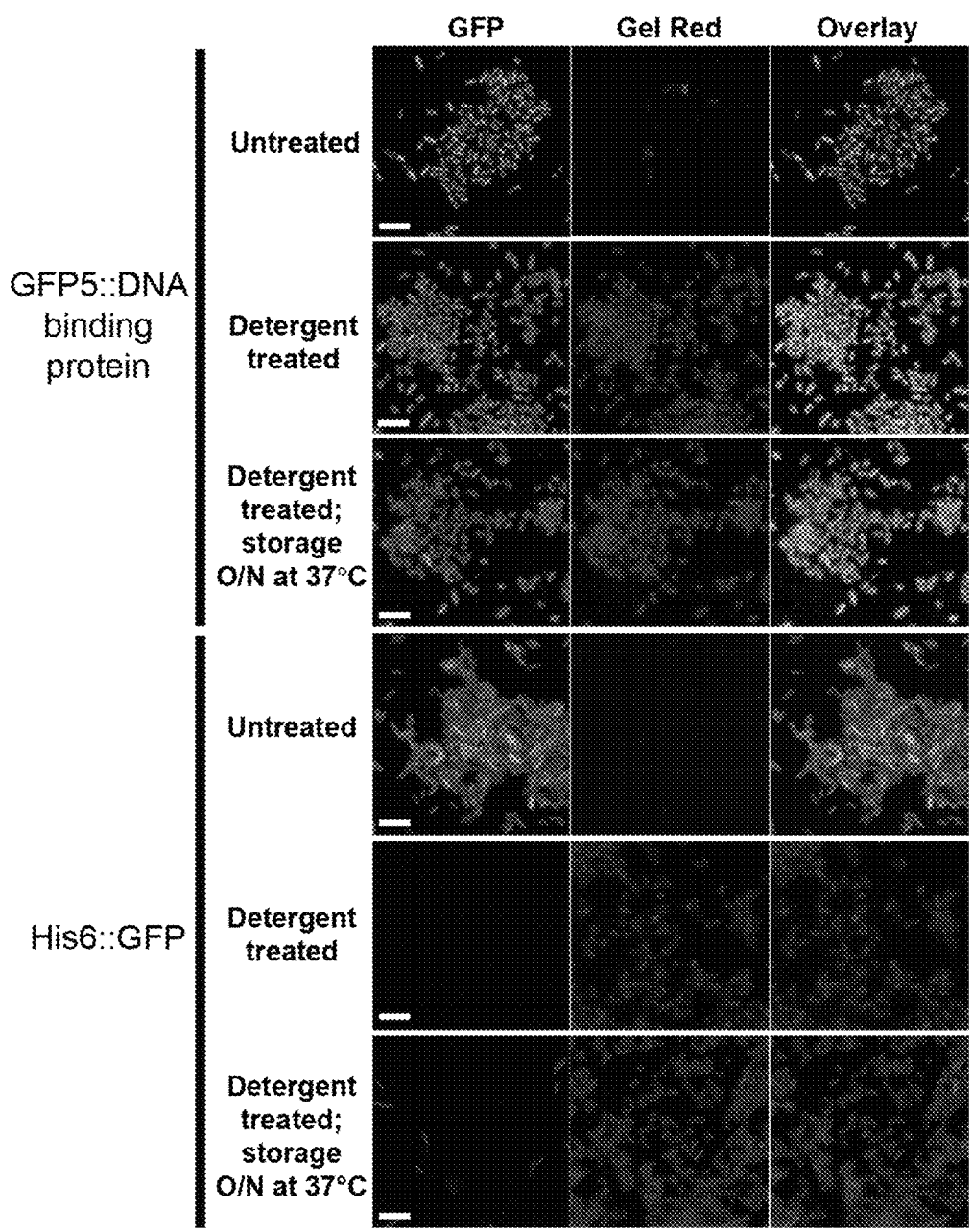

FIG. 8. Retention of DNA in permeabilised cells. *E. coli* cells expressing the GFP5::DBP fusion, or a His6::eGFP fusion were either left untreated (rows 1 and 4) or were permeabilised (rows 2, 3, 5 and 6) as described in Example 1. Permeabilised cells were either stored overnight at 4° C. or resuspended in TBS and shaken overnight at 37° C. before being viewed by fluorescence microscopy for GFP (first column) or Gel Red (second column). Co-localisation of GFP and Gel Red is presented in the third column.

Figure 9:
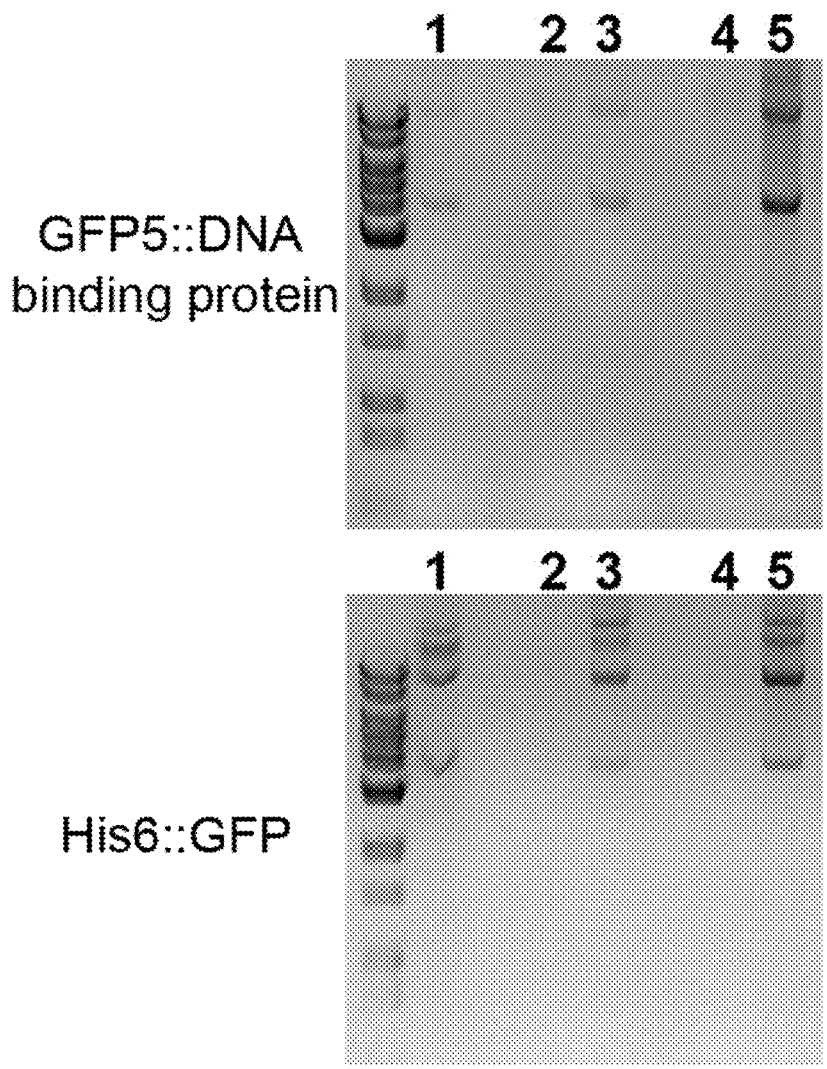

FIG. 9. DNA extraction from permeabilised cells. *E. coli* cells expressing (A) GFP5::DBP or (B) His6::eGFP fusion proteins were permeabilised as described in Example 1. Permeabilised cells were stored overnight at 4° C. or resuspended in TBS and shaken overnight at 37° C. before plasmid DNA was extracted and electrophoresed on an ethidium-bromide stained 1% agarose gel with TAE buffer. Lane 1 is the total plasmid DNA in untreated cells. Lanes 2 and 4 are the supernatants from the permeabilisation step of cell capsules stored overnight at 4° C. and shaking at 37° C., respectively, and lanes 3 and 5 are plasmid preparations from the cell capsules stored overnight at 4° C. and shaking at 37° C., respectively.

Figure 10:
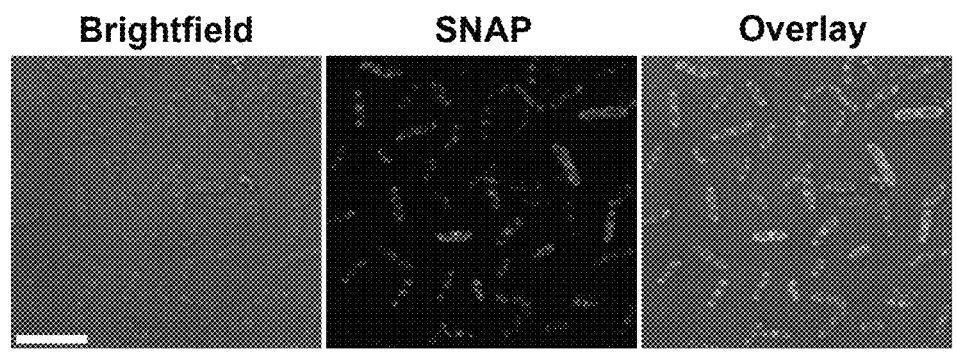

FIG. 10. SNAP labeling of the OmpF::SNAP::LPP fusion protein. *E. coli* cells expressing the OmpF::SNAP::LPP fusion protein were permeabilised as described in Example 1. Fusion protein localization was detected by labeling with the SNAP ligand BG-488 as described in Example 3. Labeled cells were viewed by brightfield microscopy (first panel) and by fluorescence microscopy (second panel). The third panel is the overlay of both brightfield and fluorescent views.

Figure 11:
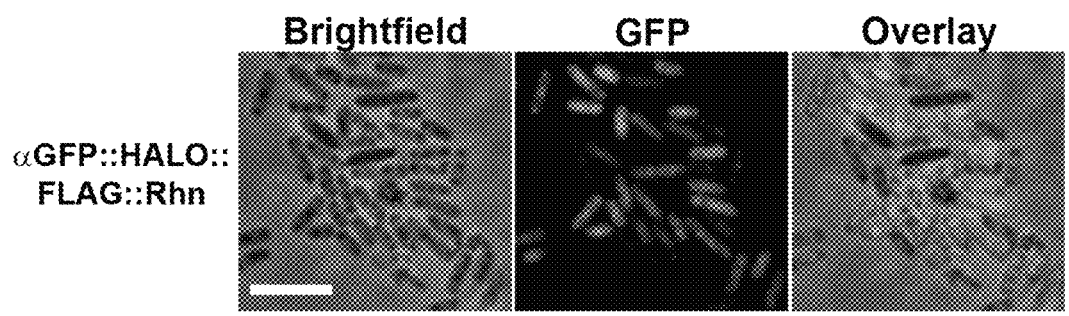

FIG. 11. Binding of eGFP by αGFP::HALO::RhnA fusion protein. *E. coli* cells expressing the αGFP::HALO::RhnA fusion protein were permeabilised as described in Example 1. Purified eGFP protein was bound to the cell capsules as described in Example 8 and eGFP was visualized by fluorescence microscopy. First panel, brightfield view; second panel, eGFP fluorescence; third panel, overlay of brightfield and fluorescence.

Figure 12:
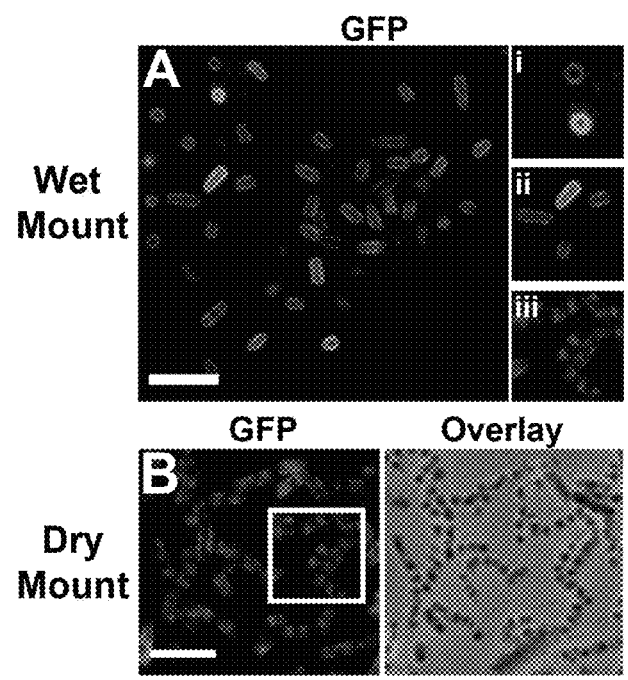

FIG. 12. Binding of eGFP by αGFP::KzPG::SNAP::DBP fusion protein. *E. coli* cells expressing the αGFP::KzPG::SNAP::DBP fusion protein were permeabilised as described in Example 1. Purified eGFP protein was bound to the cell capsules as described in Example 8 and eGFP was visualized by fluorescence microscopy by two methods, wet mount and dry mount, as described in Example 3. (A) eGFP bound to wet-mounted cell capsules. Inset panels (i) and (ii) show the cell-wall localization of the eGFP bound by the αGFP::KzPG::SNAP::DBP fusion protein. (B) and inset panel (Aiii) show the same cells prepared for microscopy by dry mount in DABCO/glycerol.

Figure 13:
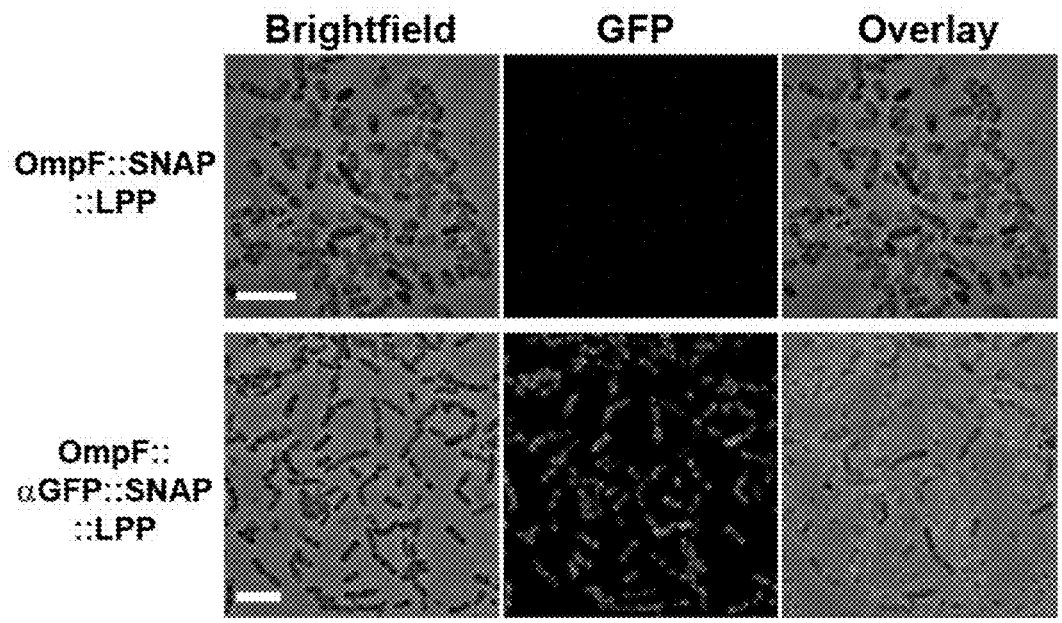

FIG. 13. Binding of eGFP by OmpF::αGFP::SNAP::LPP fusion protein. *E. coli* cells expressing the OmpF::SNAP::LPP or the OmpF::αGFP::SNAP::LPP fusion protein were permeabilised as described in Example 1. Purified eGFP protein was bound to the cell capsules as described in Example 8 and eGFP was visualized by fluorescence microscopy by dry mount, as described in Example 3. (A) Cells expressing the OmpF::SNAP::LPP fusion protein lack eGFP fluoresence (second panel, top row), unlike cells expressing the OmpF::αGFP::SNAP::LPP fusion protein (second panel, bottom row).

Figure 14:
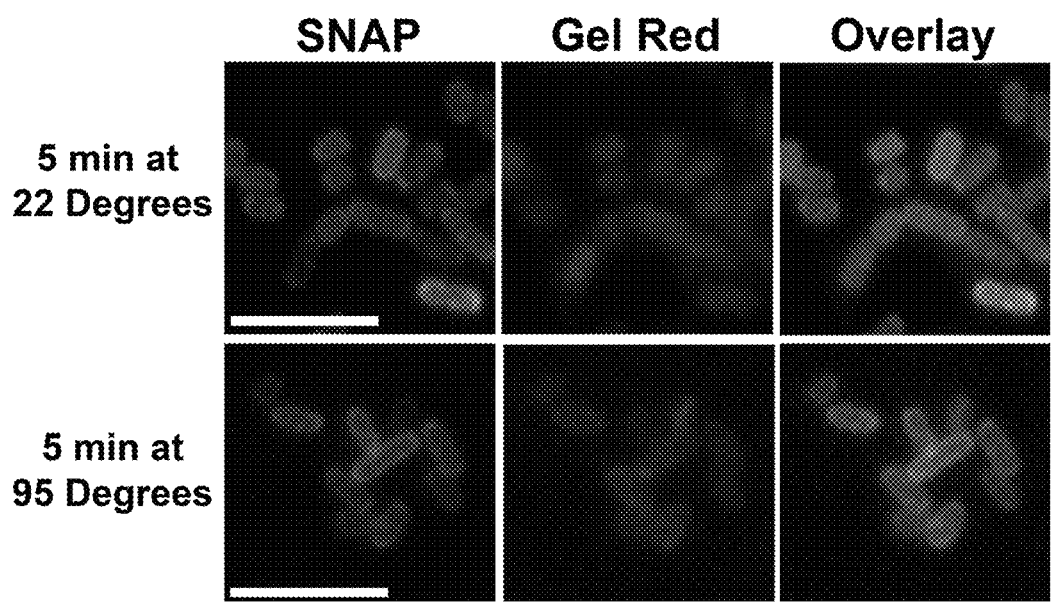

FIG. 14. Demonstration of covalent attachment to the cell wall by the LPP fusion protein. *E. coli* cells expressing the OmpF::αGFP::SNAP::LPP fusion protein were permeabilised as described in Example 1. Fusion protein localization was detected by labeling with the SNAP ligand BG-488 as described in Example 3 and DNA was stained with Gel Red. Samples were heated for 5 minutes at 22° C. (A) or at 95° C. (B) before being dry mounted and viewed by fluorescence microscopy.

Figure 15:
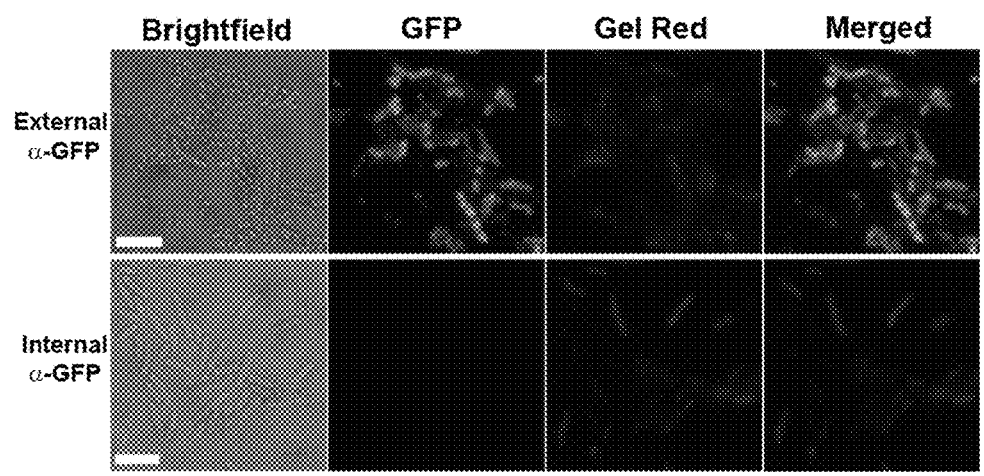
Figure 15:
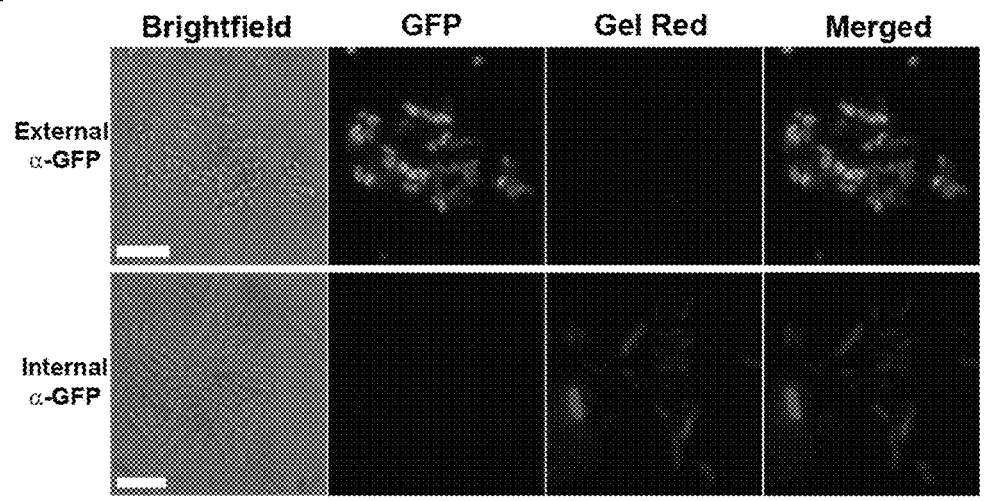

FIG. 15. Outer membrane permeabilisation using a detergent/$Ca^{2+}$ buffer. *E. coli* cells expressing the OmpF::αGFP::SNAP::LPP fusion protein (external αGFP or the αGFP::HALO::FLAG::RhnA fusion protein (internal αGFP) were permeabilised as described in Example 10. Permeabilisation of the outer membrane to large ligands was assessed by binding of eGFP to the αGFP domain attached to the cell wall. Permeabilisation of the inner membrane was assessed using a large ligand (eGFP) and small ligand (Gel Red). Both detergents Apo8 (A) and Tween20 (B) in $Ca^{2+}$ buffer demonstrated selective permeability of the outer membrane to large ligands.

Figure 16:
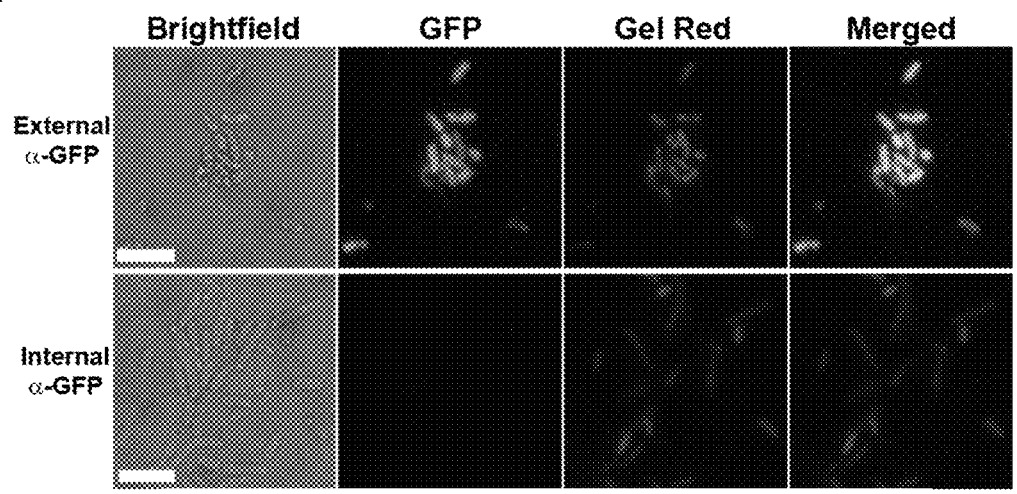
Figure 16:
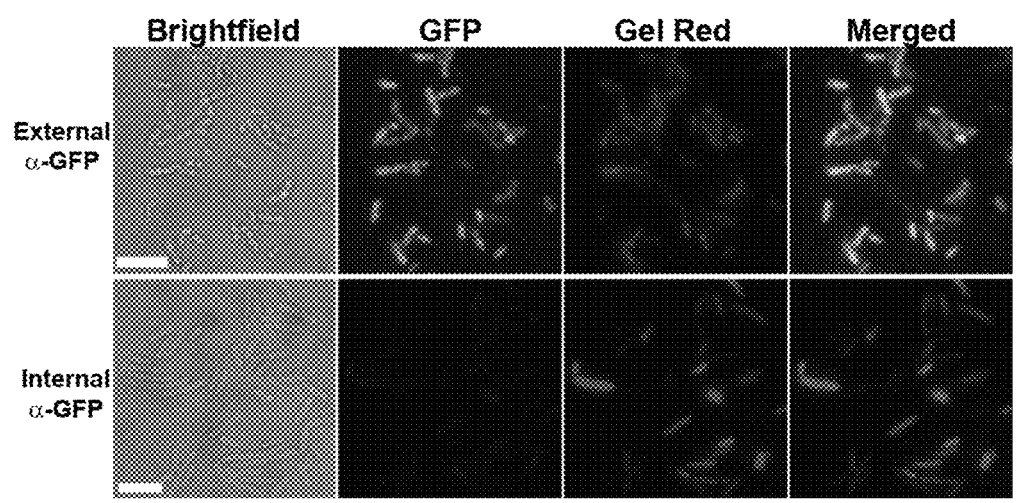

FIG. 16. Outer membrane permeabilisation using a detergent/EDTA buffer. *E. coli* cells expressing the OmpF::αGFP::SNAP::LPP fusion protein (external αGFP) or the αGFP::HALO::FLAG::RhnA fusion protein (internal αGFP) were permeabilised as described in Example 10. Permeabilisation of the outer membrane to large ligands was assessed by binding of eGFP to the αGFP domain attached to the cell wall. Permeabilisation of the inner membrane was assessed using a large ligand (eGFP) and small ligand (Gel Red). Both detergents Apo8 (A) and Tween20 (B) in EDTA buffer demonstrated selective permeability of the outer membrane to large ligands.

Figure 17:
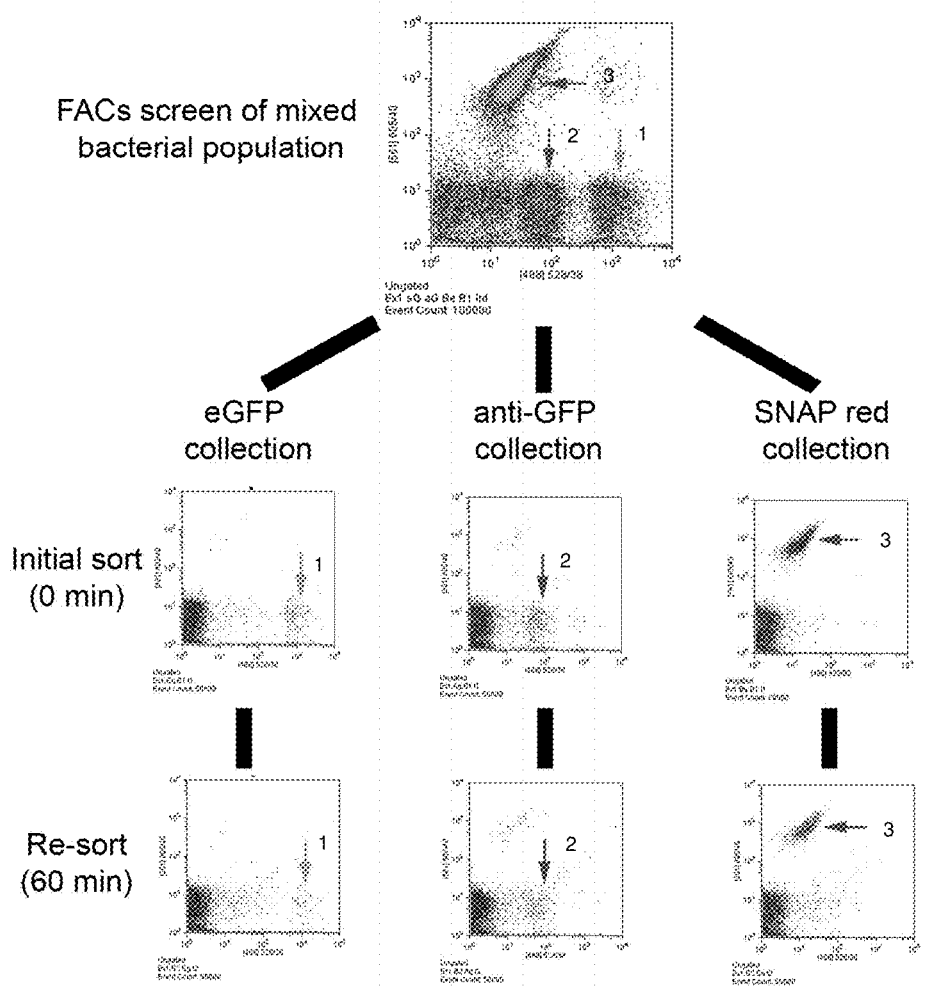

FIG. 17. FACS analysis of a mixed eGFP, and SNAP-labeled cells. Three populations of *E. coli* cells expressing; eGFP (#1 arrow); the αGFP::KzPG::SNAP::DBP fusion protein labeled with SNAP ligand BG-488 (#2 arrow); and His6::SNAP::BetB labeled with SNAP ligand BG-547 (#3 arrow) were sorted by FACS. Sorted populations were reanalysed for purity and cell integrity 60 minutes after the first sort.

Figure 18:
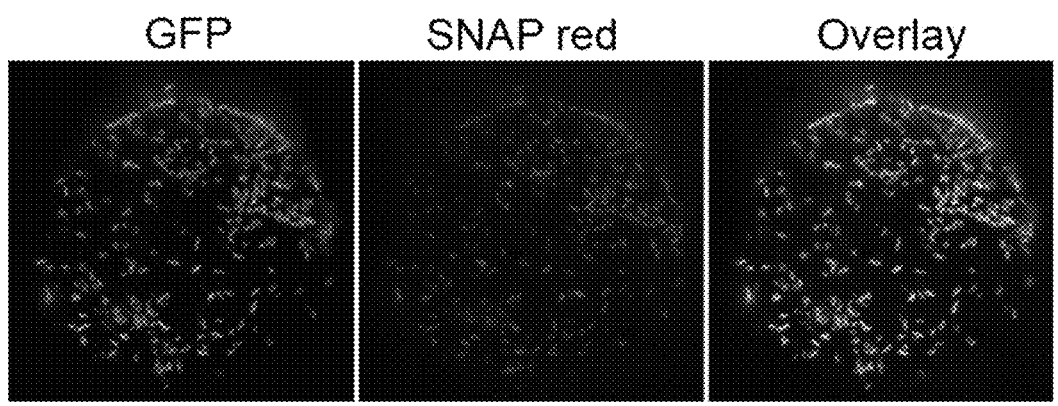

FIG. 18. A peptide linker between the αGFP and KzPG domains enables binding of E. coli cells expressing a αGFP::KzPG::SNAP::DBP fusion protein to a sepharose support. Cells expressing a αGFP::KzPG::SNAP::DBP fusion protein with a 12-mer linker region, RL6, between the αGFP and KzPG domains were bound to a $Co^{2+}$-sepharose support through a His6::eGFP intermediate. GFP binding is shown in the left panel (green); SNAP ligand (red) binding of the fusion protein is shown in the middle panel; overlay of each is shown on the right.

Figure 19:
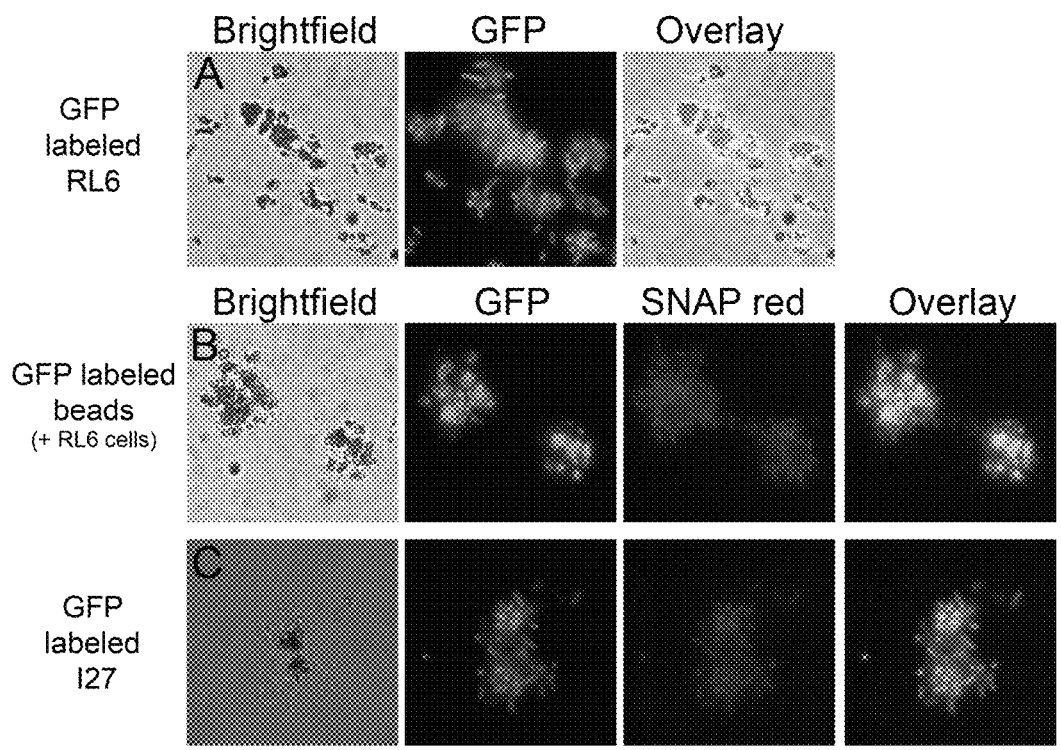

FIG. 19. Binding of E. coli cells expressing αGFP::RL6::KzPG::SNAP::DBP fusion protein to streptavidin-labeled magnetic beads. (A) Biotin-labeled eGFP (middle and right panels) was bound to cells expressing the αGFP::RL6::KzPG::SNAP::DBP fusion protein which was in turn bound to streptavidin-labeled magnetic particles. (B) Converse binding of cells expressing the αGFP::RL6::KzPG::SNAP::DBP fusion protein to streptavidin-labeled magnetic particles which had first been labeled with biotinylated-eGFP. In this example the beads are labeled green (GFP panel), the cells were labeled with the BG-547 SNAP ligand (red, SNAP red panel). (C) A domain linker, the $27^{th}$ Ig domain of human titin, was also effective as a binding spacer. E. coli cells expressing the αGFP::I27::RL6::KzPG::SNAP::DBP fusion protein were first bound to biotinylated eGFP (green, GFP panel) and labeled with the BG-547 SNAP ligand (red, SNAP red panel) before being bound to streptavidin-labeled magnetic particles.

Figure 20:
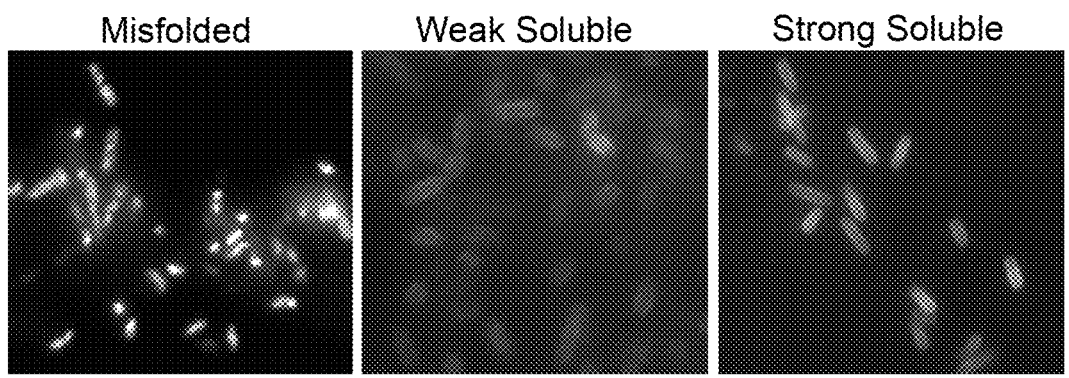

FIG. 20. Expression of mouse scFv genes in the E. coli cytoplasm as scFv::I27::RL6::KzPG::SNAP::DBP fusion proteins. A mouse scFv library was constructed and displayed according to the method of the invention in the E. coli cytoplasm. Clones with detectable expression were detected via SNAP ligand binding and were catagorised as misfolded (left panel), weakly expressed but soluble (middle panel) or highly expressed and soluble (right panel).

Figure 21:
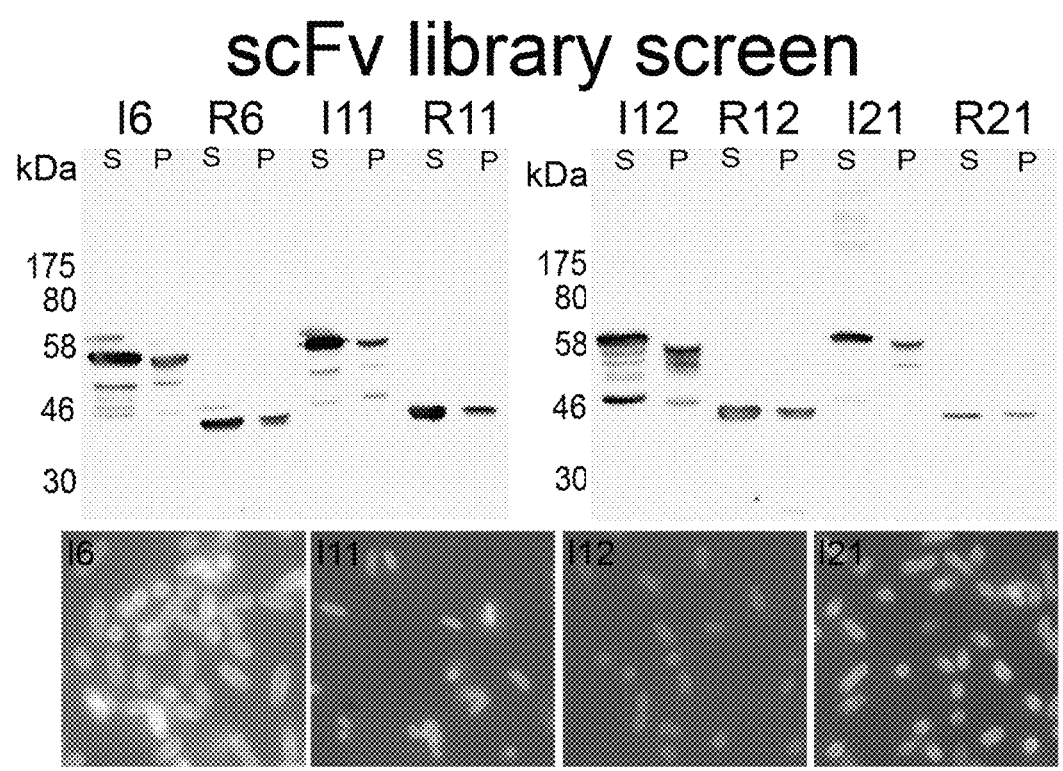

FIG. 21. Detection of soluble and insoluble scFv expression in the E. coli cytoplasm. Selected clones that were found to be highly expressed and soluble in a limited screen from the mouse scFv expression library were subcloned into expression constructs as scFv::I27::RL6::FLAG and scFv::RL6::FLAG fusion proteins. Protein fractions were loaded as either soluble or insoluble onto SDS-PAGE gels, transferred to nitrocellulose membranes and detected using αFLAG antibodies. Samples are paired for soluble (S) or insoluble (P) fractions, as well as each clone being expressed with the I27::RL6 (I) or RL6 (R) linker. A fluorescence microscopy image of the original scFv clone in the I27::RL6::KzPG::SNAP::DBP display construct isolated from the library screen is also shown in the lower panels.

KEY TO THE SEQUENCE LISTING

SEQ ID NO:1—Nucleotide sequence of pAra3::His6::SNAP arabinose vector
SEQ ID NO:2—Nucleotide sequence of pAra3::His6::KzPG::SNAP::DBP vector
SEQ ID NO:3—Nucleotide sequence of pAra3::OmpF::SNAP::LPP vector
SEQ ID NO:4—Nucleotide sequence of pAra3::αGFP (R35)::HALO::FLAG::RhnA vector.
SEQ ID NO:5—Randomized peptide spacer domain
SEQ ID NOs:6 to 12—Peptide linker spacers
SEQ ID NO:13—I27::RL6::KzPG::SNAP::DBP SEQ ID NO:14—I27::RL6::KzPG::SNAP::DBP coding sequence
SEQ ID NO:15—Library scaffold vector
SEQ ID NO:16—I27 spacer

DETAILED DESCRIPTION

General Techniques and Definitions

Unless specifically defined otherwise, all technical and scientific terms used herein shall be taken to have the same meaning as commonly understood by one of ordinary skill in the art (e.g., in protein chemistry, biochemistry, cell culture, molecular genetics, microbiology, and immunology).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, $3^{rd}$ edn, Cold Spring Harbour Laboratory Press (2001), R. Scopes, Protein Purification—Principals and Practice, $3^{rd}$ edn, Springer (1994), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The terms "polypeptide", "protein" and "peptide" are generally used interchangeably herein. As used herein, the term "exogenous polypeptide" refers to a polypeptide encoded by an exogenous polynucleotide. The term "exogenous polynucleotide" as used herein refers to a polynucleotide which is foreign to the cell into which it has been introduced, or that the sequence is homologous to a sequence in the cell into which it is introduced but in a position within the host cell nucleic acid in which the polynucleotide is not normally found.

The term "antibody" as used in this invention includes polyclonal antibodies, monoclonal antibodies, bispecific antibodies, diabodies, triabodies, multibodies, heteroconjugate antibodies, chimeric antibodies including intact molecules as well as fragments thereof, such as Fab, F(ab')2, Fv and scFv and other antibody-like molecules.

The term "about" as used herein refers to a range of +/−5% of the specified value.

Permeabilisation

In the methods of the present invention, the bacterial cell is permeabilised, thus allowing at least some of the soluble cellular components to diffuse through the cell wall. The polypeptide to be screened for a desired activity is retained within the bacterial cell wall, or is attached to the bacterial cell wall. As used herein, "permeabilised bacterial cell" refers to the use of a permeabilising agent to produce pores in one or more cellular membranes, or to solubilise cellular membranes, while not hydrolysing linkages between peptidoglycans thereby keeping the cell wall intact. Non-limiting examples of agents capable of permeabilising a bacterial cell include detergents and organic solvents. Permeabilisation advantageously allows the entry of small to moderately sized proteins, for example up to 120 kDa, or other molecules of equivalent or smaller size, into the cellular capsule that remains intact. Further, by maintaining the integrity of the bacterial cell wall, the permeabilised bacterial cells are less fragile than spheroplasts that are produced in prior art methods, for example by treatment of bacterial cells with Tris-EDTA-lysozyme, in which the bacterial cell wall is at least partially hydrolysed. The permeabilised bacterial cells produced in the methods of the present invention are well suited to techniques such as fluorescence activated cell sorting (FACS), whereas spheroplasts are damaged by the high shear flow cytometry environment and require controlled osmotic conditions, thus limiting their potential uses.

Preferably, the permeabilisation treatment preserves the cellular proteins in their native state and interactions. Non-ionic detergents are generally less disruptive to protein folding and protein complexes than ionic detergents. Thus, in a preferred embodiment, a non-ionic detergent is used to permeabilise the bacterial cell wall. Non-limiting examples of non-ionic detergents include Triton X-100, Triton X-114, Brij 35, Brij 58, Tween 20, Tween 80, Nonidet P-40 Substitute, Octyl β Glucoside, Mega 8, Mega 9, Mega 10, BigCHAP, Deoxy BigCHAP, Apo8, and 8TGP.

Mixtures of detergents may be used to permeabilise the bacterial cell. For example, the detergent may be a mixture of two or more non-ionic detergents. In one embodiment, the detergent is a mixture of Mega 10 and Apo8.

When the polypeptide to be screened for a desired activity is attached to the bacterial cell wall, or integrated or attached to the inner cell membrane, the skilled person will appreciate that it may not be necessary to permeabilise the inner membrane of the bacterial cell. Thus, in one embodiment the bacterial cell is selectively permeabilised. By "selectively permeabilised" it is meant the outer membrane of the permeabilised bacterial cell is permeabilised to a greater extent than the inner membrane, whereby 50% or less, or more preferably 40%, 30%, 20%, 10%, 5%, 4%, 3%, 2%, 1% or less, or none, of a membrane impermeable substance, for example the membrane impermeable DNA-binding ligand Gel Red, permeates the inner membrane of a selectively permeabilised cell when compared to a permeabilised cell in which both the inner and outer membranes have been permeabilised such as by using a solution comprising 0.5% Mega 10 and 0.5% Apo8.

While the skilled person will be able to determine suitable conditions for selectively permeabilising a bacterial cell in accordance with the methods of the present invention, in one embodiment the bacterial cell is selectively permeabilised with a non-inonic detergent. For example, the non-ionic detergent may be selected from Apo8 and Tween20. In one embodiment, a solution for selectively permeabilising the bacterial cell comprises the detergent at a concentration of about 0.2% to about 0.4%, or about 0.2% to about 0.3%, or at about 0.2%. Preferably, the solution for selectively permeabilising the bacterial cell comprises the detergent in a buffer comprising $Ca^{2+}$ or EDTA. Examplary buffers suitable for selectively permeabilising a bacterial cell include 0.2-0.4% Apo8 or Tween20 in 25 mM Tris, 1 mM EDTA (pH 8.0), or 25 mM Tris, 2 mM $Ca^{2+}$ (pH 8.0). In one embodiment, selective permeabilisation of a bacterial cell may be achieved, for example, by incubating the cell in a suitable buffer at about 25° C. for about 10 minutes.

Polypeptide Expression

A polypeptide to be screened for a desired activity may be cloned into a suitable vector for expression in a bacterial cell. "Vector" as used herein refers to any vector known in the art to be suitable for transforming a bacterial cell. Preferably, the vector is also capable of replicating within the bacterial cell independently of the host's genome. Vectors include plasmids, viruses and cosmids as well as linear DNA elements, such as the linear phage N15 of *E. coli*, and/or extrachromosomal DNA that replicates independently of a bacterial cell genome. Preferably, the vector is an expression vector.

As used herein, an "expression vector" is a vector that is capable of effecting expression of a specified polynucleotide molecule in a bacterial cell. Preferably, the expression vector is also capable of replicating within the bacterial cell. Suitable expression vectors typically contain regulatory sequences such as transcription control sequences, translation control sequences, origins of replication, and other regulatory sequences that are compatible with the recombinant bacterial cell and that control the expression of polynucleotide molecules encoding the polypeptide. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in a bacterial cell. A variety of such transcription control sequences are known to those skilled in the art.

Transformation of an expression vector into a bacterial cell can be accomplished by any suitable method by which a polynucleotide molecule can be inserted into the cell. Transformation techniques include, but are not limited to, electroporation and chemical transformation. Transformed polynucleotide molecules can remain extrachromosomal or can integrate into one or more sites within a chromosome of the transformed (i.e., recombinant) cell in such a manner that their ability to be expressed is retained.

Recombinant DNA technologies can be used to improve expression of a transformed polynucleotide molecule by manipulating, for example, the number of copies of the polynucleotide molecule within a host cell, the efficiency with which those polynucleotide molecules are transcribed, the efficiency with which the resultant transcripts are translated, and the efficiency of post-translational modifications. Recombinant techniques useful for increasing the expression of polynucleotide molecules include, but are not limited to, operatively linking polynucleotide molecules to high-copy number plasmids, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of polynucleotide molecules to correspond to the codon usage of the host cell, and the deletion of sequences that destabilize transcripts.

The skilled person will be able to readily determine bacterial strains suitable for expressing polypeptides in the methods of the invention. Those skilled in the art would understand that Gram negative bacteria suitable for use in the methods of the invention include *Salmonella, E. coli, Shigella, Campylobacter, Fusobacterium, Bordetella, Pasteurella, Actinobacillus, Haemophilus* and *Histophilus*. In a preferred embodiment, the Gram negative bacteria is *E. coli*.

Protein Complexes

The polypeptide to be screened for a desired activity may be associated with at least a second polypeptide to form a protein complex having a molecular size such that the protein complex is retained inside the permeabilised bacterial cell. The polypeptide may be associated with the second polypeptide by, for example, covalent bonds such as disulphide bridges, or by non-covalent association. "Non-covalent association" refers to molecular interactions that do not involve an interatomic bond. For example, non-covalent interactions involve ionic bonds, hydrogen bonds, hydrophobic interactions, and van der Waals forces. Non-covalent forces may be used to hold separate polypeptide chains together in proteins or in protein complexes. Thus, the polypeptide and second polypeptide may be expressed as separate polypeptides either from the same or different vectors, or one or both of the polypeptides may be expressed from DNA encoding the polypeptides that has been integrated into the bacterial cell genome.

Alternatively, the polypeptide and second polypeptide which are associated in a protein complex may be a fusion protein. As used herein, "fusion protein" refers to a hybrid protein, which consists of two or more polypeptides, or fragments thereof, resulting from the expression of a polynucleotide that encodes at least a portion of each of the two polypeptides.

Protein Complexes Retained in the Permeabilised Bacterial Cell by Molecular Size The second polypeptide may be any polypeptide having sufficient molecular size, i.e. sufficient molecular weight or molecular radius, such that at least some of the complex formed with the polypeptide being screened for a desired activity is incapable of diffusion from the permeabilised bacterial cell. Thus, the protein complex is retained within the bacterial cell following permeabilisation of the cell. The person skilled in the art will appreciate that the nature of the second polypeptide, including its molecular weight and whether it is a globular or rod (filamentous) protein, will determine its ability to prevent or inhibit diffusion of the protein complex through the bacterial cell wall. In one embodiment, the molecular weight of the second polypeptide is at least about 30 kDa, or at least about 40, 50, 60, 70, 80, 90, 100, 120, 130, 140, 150 or more kDa. In one embodiment, the second polypeptide is at least about 120 kDa.

In one embodiment, the second polypeptide forms multimers having a molecular size greater than the pore-exclusion size of the permeabilised bacterial cell. As used herein, the term "multimer" and grammatical variations thereof refer to formation of a multimeric complex between two or more distinct molecules. The multimer may comprise, for example, two or more molecules of the same protein (i.e. a homo-multimer) or a mixture of two or more different or non-identical proteins (i.e. a hetero-multimer). Proteins that form multimers suitable for use in the methods of the invention include those that form dimers, trimers, tetramers, pentamers, hexamers, and higher order multimers comprising seven or more subunits.

Multimeric proteins include homodimers, for example, PDGF receptor α, and β isoforms, erythropoietin receptor, MPL, and G-CSF receptor, heterodimers whose subunits each have ligand-binding and effector domains, for example, PDGF receptor αβ isoform, and multimers having component subunits with disparate functions, for example, IL-2, IL-3, IL-4, IL-5, IL-6, IL-7, and GM-CSF receptors. Non-limiting examples of other multimeric proteins that may be utilized in the methods of the present invention include factors involved in the synthesis or replication of DNA, such as DNA polymerase proteins involved in the production of mRNA, such as TFIID and TFIIH; cell, nuclear and other membrane-associated proteins, such as hormone and other signal transduction receptors, active transport proteins and ion channels, multimeric proteins in the blood, including hemoglobin, fibrinogen and von Willabrand's Factor; proteins that form structures within the cell, such as actin, myosin, and tubulin and other cytoskeletal proteins; proteins that form structures in the extra cellular environment, such as collagen, elastin and fibronectin; proteins involved in intra- and extra-cellular transport, such as kinesin and dynein, the SNARE family of proteins (soluble NSF attachment protein receptor) and clathrin; proteins that help regulate chromatin structure, such as histones and protamines, Swi3p, Rsc8p and moira; multimeric transcription factors such as Fos, Jun and CBTF (CCAAT box transcription factor); multimeric enzymes such as acetylcholinesterase and alcohol dehydrogenase; chaperone proteins such as GroE, Gro EL (chaperonin 60) and Gro ES (chaperonin 10); anti-toxins, such as snake venom, botulism toxin, *Streptococcus* super antigens; lysins (enzymes from bacteriophage and viruses); as well as most allosteric proteins. In one embodiment, the multimeric protein is an *E. coli* protein. Non-limiting examples of *E. coli* proteins that form multimers include L-rhamnose isomerase (RhnA; for example NCBI accession CAA43002), β-galactosidase (β-gal; for example NCBI accession YP 001461520), betaine aldehyde dehydrogenase (BetB; for example NCBI accession AAA23506), glutamate-5-kinase (GSK; for example NCBI accession AAB08662), glutathione synthase (GshB; for example NCBI accession AP_003504), and a medium chain aldehyde dehydrogenase (YdcW; for example NCBI accession AP_002067).

In one embodiment, the polypeptide being screened for a desired activity has a molecular size sufficient to retain the polypeptide within the bacterial cell wall. Thus, the person skilled in the art will appreciate that such a polypeptide need not necessarily be associated with a second polypeptide in order to retain the polypeptide within the permeabilised bacterial cell.

DNA Binding Proteins

The present inventors have found that DNA is retained within a bacterial cell following permeabilisation. Thus, in one embodiment, the polypeptide is associated with a DNA-binding protein to form a protein complex that binds DNA and that is retained inside the bacterial cell. As used herein, "DNA-binding protein" refers to any protein comprising a DNA-binding domain comprising at least one motif that recognizes double-stranded or single-stranded DNA. As would be known to the person skilled in the art, DNA-binding domains include helix-turn-helix, zinc finger, leucine zipper, winged helix, winged helix turn helix, helix-loop-helix, immunoglobulin fold recognizing DNA, or B3 domains. Associating the polypeptide with a DNA-binding protein advantageously provides for enhanced recovery of DNA, for example a plasmid, encoding the polypeptide in the screening methods of the invention.

Examples of DNA binding proteins include bacterial competence proteins such as, but not limited to, *E. coli* DNA binding proteins, *Neisseria gonorhoeae* DNA binding proteins, for example ComE, Adenovirus E2 proteins, AraC transcription factor, basic helix-loop-helix transcription factors, basic-leucine zipper transcription factors, butyrate response factor, centromere protein B, COUP transcription factors, early growth response transcription factors, G-box binding factors, GATA transcription factors, HMGA proteins, homeodomain proteins, 1-kappa B proteins, integration host factors, interferon regulatory factors, interferon-stimulated gene factor 3, Kruppel-like transcription factors, leucine responsive regulatory protein, matrix attachment region binding proteins, methyl-CpG-binding protein, MutS homolog 2 protein, myeloid-lymphoid leukaemia protein, NF-Kappa B, NF1 transcription factors, nuclear respiratory factors, oncogene protein p55, origin recognition complex, paired box transcription factors, POU domain factors, proto-oncogene factors, Rad51 recombinase, Rad52 DNA repair and recombination protein, replication protein A, replication protein C, retinoblastoma protein, Smad proteins, SOX transcription factors, T-box domain proteins, TCF transcription factors, telomere-binding proteins, Toll-like receptor 9, trans-activators, and winged-helix transcription factors. In one embodiment, the DNA binding protein is an *E. coli* DNA binding protein. In another embodiment, the DNA binding protein is a *Neisseria gonorrhoeae* protein, for example ComE.

Cell Wall Binding Proteins

The polypeptide that is being screened for a desired activity may be associated with a bacterial cell wall-binding protein. The skilled person will understand that the choice of a cell wall-binding protein would depend on the host cell species, as different bacteria have different cell wall compositions. While bacteria have cell walls made up of peptidoglycan (PG), chemical modifications between species can affect cross-species binding. The skilled person will readily be able to determine cell wall-binding proteins suitable for use in a particular bacterial species.

Bacterial cell wall-binding proteins include proteins known to have a domain structure, whereby part of the polypeptide chain in the native structure is able to recognise and bind specific molecules or molecular conformations on the bacterial cell wall. Thus, the term "bacterial cell wall-binding protein" includes a protein domain which is part of the protein which specifically binds to the bacterial cell wall. Examples of bacterial cell wall-binding proteins include the cell wall hydrolases as coded by bacteriophages, cell wall hydrolases of bacteria and different autolysins. Further encompassed are receptor molecules coded by the DNA of bacteriophages and other viruses. Where the bacterial cell wall-binding protein is from hydrolytic enzymes of bacteriophage origin, which are capable of specific binding to bacteria, the cell wall-binding protein maintain their binding ability but preferably have no significant hydrolytic activity.

In one embodiment, the cell wall-binding protein binds non-covalently to the cell wall of *E. coli*. For example, for an *E. coli* host cell there are endogenous PG-binding proteins with a conserved ~100 amino acid PG-binding domain occurring in PAL, OmpA, YiaD, YfiB, and MotB (Parsons et al., 2006). However, proteins from other organisms have been shown to be well expressed in *E. coli* and to bind the cell wall with high affinity, for example the ~70 amino acid PG-binding domain from *Pseudomonas* φKZ phage (KzPG) (Briers et al., 2009). Thus a PG-binding domain from a protein that binds PG may be used as a bacterial cell wall-binding protein in the methods of the invention.

In an exemplary embodiment, the PG-binding domain may be fused to the polypeptide that is being screened for a desired activity and expressed in the cytosol of the bacterial cell. Upon membrane permeabilisation, the PG-binding domain binds to the cell wall resulting in the retention of the polypeptide of interest within the permeabilised cell. To potentially further enhance retention of the polypeptide of interest within the cell, the skilled person will understand that the polypeptide may be associated with a DNA-binding protein in addition to a bacterial cell wall-binding protein.

Alternatively, the polypeptide of interest may be associated with a protein that is capable of linking covalently to the bacterial cell wall. Preferably the protein comprises a periplasmic-targeting signal. Thus, the polypeptide is expressed in the cytosol of the bacterial cell, but targeted to the periplasm where it is linked to the cell wall before membrane permeabilisation.

By way of non-limiting example, the bacterial cell wall-binding protein that attaches to the cell wall covalently may be a lipoprotein capable of binding to the cell wall and which lacks a functional N-terminal signal sequence necessary for outer membrane attachment. For example, the lipoprotein may be *E. coli* LPP. LPP is an abundant *E. coli* protein that forms a trimeric coiled-coil. In its native form, one end is tethered to the outer membrane via lipidation and the other is covalently bound to the cell wall via a C-terminal lysine. The lipoprotein may further comprise a sequence which targets the lipoprotein to the periplasm, for example an OmpF periplasmic targeting sequence. In one embodiment, the lipoprotein is *E. coli* lipoprotein lacking a functional N-terminal signal sequence necessary for outer membrane attachment.

In light of the teaching of the present specification, the person skilled in the art will be able to identify or design proteins that attach covalently to the bacterial cell wall and that are suitable for use in the methods of the present invention.

In one embodiment of the invention, the polypeptide being screened for a desired activity is a fusion polypeptide comprising a KzPG domain and one or more other domains selected from a spacer, SNAP and/or DBP. In one particular embodiment, the fusion polypeptide comprises one or more spacers and the KzPG, SNAP and DBP domains.

Spacers

In one embodiment, the polypeptide being screened for a desired activity may be expressed as a fusion polypeptide which comprises one or more spacers. A "spacer" as used herein refers to peptide or polypeptide that may be included in a fusion polypeptide to enhance expression of the polypeptide in a bacterial cell or to decrease steric hindrance such that the polypeptide being screened for a desired activity may assume its desired tertiary structure and/or interact appropriately with its target molecule. Thus, the fusion protein may comprise one or more spacers before, after, or between one or more polypeptide domains in the fusion polypeptide. For spacers and methods of identifying desirable spacers, see, for example, George, et al. (2003).

In one embodiment, the spacer comprises one or more amino acid sequences that are between 1-50 amino acid residues in length, or about 1-25 residues, or about 5-15 residues in length. For example, the spacer may be selected from one or more of I27, RL1, RL2, RL3, RL4, RL5 and/or RL6. The person skilled in the art will understand that a limited number of amino acid substitutions, for example, 1, 2, 3, 4 or 5 amino acid substitutions may be introduced into the spacer without affecting its ability to function as a spacer. In one particular embodiment, the one or more spacers are selected from any one of SEQ ID NOs:6 to 12 or 16. Thus in one embodiment, the polypeptide being screended for a desired activity is a fusion polypeptide comprising I27, RL6, KzPG, SNAP and DBP.

Screening Methods and Protein Evolution

The present invention provides methods for screening polypeptides for a desired activity against a target molecule. As used herein, the term "desired activity" refers to any potential useful activity of a polypeptide and includes, but is not limited to, binding, enzymatic modification, folding stability and/or thermal stability.

The term "target molecule" refers to a molecule that binds to and/or is modified by the polypeptide and may be for example an antibody, a receptor, an antigen, an enzyme etc.

Thus, "target molecule" can be used to refer to a substrate such as an enzymatic substrate or a molecule that is being evaluated for binding (e.g., a ligand, eptiope, antigen, multimerization partner such as a homo or hetero dimeric partner, etc., or any combination thereof).

It will be appreciated that polypeptide activities may be screened for or selected in the context of a single type of cell expressing a single polypeptide, or in the context of a library of cells each expressing a different polypeptide or polypeptide variant. Thus, the methods of the present invention may be used for in vitro protein evolution. In vitro protein evolution allows for a large number of protein functions and characteristics to be investigated and typically comprises two main steps: diversification and selection. Diversification relies on the ability to generate diverse libraries of nucleic acids coding for polypeptides. Selection can be achieved by screening the libraries for a desired activity and linking the activity to the genotype, for example, by identifying the member of the library that comprises the genotype that is responsible for the observed activity.

DNA libraries are a collection of recombinant vectors containing DNA inserts (DNA fragments) that encode a polypeptide. The origin of the DNA inserts can be genomic, cDNA, synthetic or semi-synthetic. The polypeptide may have any desired activity, for example the polypeptide of interest may be a binding protein, for example an antibody, or an enzyme for example, a polymerase, ligase, restriction enzyme, topoisomerase, kinase, phosphatase, metabolic enzyme, catalytic enzyme, or a growth factor hormone, antimicrobial peptide, antigen, receptor, reporter protein, immunomodulatory protein, neurotransmitter, structural protein, transcription factor or transporter. In one embodiment, the polypeptide is an antibody or an enzyme. Thus, the methods of the present invention can be used for screening for variants of a polypeptide having a desired activity.

The cloning and construction of DNA libraries of, for example, binding proteins or enzymes, can be performed using methods known in the art. For example, Lutz and Patrick (2004) have reviewed methods of generating library variability and strategies for gene recombination for use in protein engineering. For screening of displayed polypeptide variants, the strategies used for surface-displayed libraries could be adopted and adapted for the methods of the present invention (Becker et al., 2004; Kenrick et al., 2007; Miller et al., 2006; Daugherty et al., 2000).

A library of nucleic acids can be introduced into a plurality of bacterial cells resulting in the expression of a member of the library in each of the bacterial cells. In addition to being expressed, the polypeptides are retained within the permeabilised bacterial cell, or attached to the cell wall, in order to evaluate their function or characteristic. Nucleic acid libraries of a polypeptide, for example, a binding protein such as an antibody, or of an enzyme, can be generated through a variety of methods including through the introduction of mutations such as point mutations, deletions, and insertions, or through recombination events. Methods for the generation of libraries of variants are known in the art and include error-prone PCR, synthesis of DNA in DNA repair compromised bacteria, and chemical modification of DNA. Methods for the generation of libraries through recombination are known in the art and include gene shuffling, assembly of DNA in highly recombinogenic bacteria, synthetic nucleic acid library assembly, etc., or any combination thereof. In this way a library of polynucleotides encoding polypeptides can be introduced into a plurality of bacterial cells resulting in the expression of one or members of the library in each of the bacterial cells.

In some embodiments, a library comprises two or more variants of a polypeptide wherein each variant comprises a unique polypeptide with a minor change in amino acid sequence. In other embodiments, a library comprises two or more unrelated sequences. For example, to identify a candidate polypeptide that can inhibit an enzyme, a library of random sequences or predetermined sequences may be interrogated. A library can have at least 2, at least 5, at least 10, at least 50, at least 100, at least 1000, at least 10,000, at least 100,000, at least 1,000,000, at least $10^7$ or more members.

Binding Protein Display

In one embodiment, the methods of the present invention are applied to the evolution of binding proteins, such as for example antibodies. Thus, in one embodiment, the polypeptide that is screened for a desired activity is a binding protein, the target molecule may be any molecule to which the binding protein may bind, and the desired activity is binding, and/or the extent of binding to the target molecule. The methods of the invention may comprise, for example, culturing a bacterial cell comprising a polynucleotide encoding a binding protein so that the protein is produced in the cell. The cell is subsequently permeabilised and the permeabilised cell contacted with a target molecule. Any suitable method in the art may be used for determining if the polypeptide binds, and/or the extend of binding to, the target molecule.

The methods of the invention are particularly suited to the screening of binding protein display libraries. Unlike other methods of in vivo surface display, which absolutely require the targeting of the protein to an extracellular space as the cellular membranes prevent interaction with the labeled target presented to the display protein, the methods of the invention can express and fold the affinity proteins in the cytoplasm of the host cell. Thus, the screening parameters can include the high yield and productive folding of the affinity variant protein in the cytoplasm of bacteria.

Furthermore, as cytoplasmic protein expression and folding is in a reducing environment, the methods of the invention can be applied to select for variants of antibodies, or other proteins that have disulphide bonds in their native form, that can productively fold in a reducing environment. The variants selected would be expected to be more stable as they would not be reliant on intra- or inter-domain disulphide bonds for folding stability. This approach has application towards the development of antibodies that could be used for intracellular binding of targets, to either neutralize or label.

The methods of the invention can therefore be used as a platform for the display and selection of a variety of binding proteins, including those scaffolds known to the art, such as single-chain antibodies (scFv), domain antibodies, Fab, and the non-antibody scaffolds such as lipocalins, FN3, ubiquitin, γ-B-crystallin.

Enzyme Display

The methods of the invention can be used for the display of enzymes and enzyme libraries and for the evolution of enzyme properties. Thus, in one embodiment, the polypeptide that is screened for a desired activity is an enzyme, the target molecule is a substrate of the enzyme, and the desired activity is binding to and/or enzymatic modification of the target molecule. The skilled person will understand that methods for the development of assays for enzyme activities using other surface display technologies could be equally applied as assays to the methods of the invention.

The methods of the invention would also be well suited in the use of enzyme libraries that are expressed in the host cell, which is permeabilised and then suspended as a water-in-oil-in-water emulsion (w/o/w). Aharoni et al. (2005) demonstrated the utility of using surface-displayed enzyme libraries in a w/o/w emulsion by FACS for the improvement of paraoxonase. The advantages of encapsulation in a non-permeable oil membrane are that a diffusible substrate and product can be kept in proximity to the enzyme activity and coding nucleic acid sequence. However, the screen described by Aharoni et al. (2005) requires that the enzyme be displayed on the exterior of the host cell. Using the methods of the invention, intracellular expression and folding of enzyme libraries could be used for the improvement in enzyme function.

In the methods of the invention, a bacterial cell comprising a polynucleotide encoding an enzyme is cultured in order to produce the enzyme. Following permeabilisation of the bacterial cell, the cell is contacted with a substrate of the enzyme and known methods may be used to determine if the enzyme modifies, and/or the rate of enzymatic modification of, the substrate.

In some instances, it may be desirable that the target molecule (for example an enzyme substrate) is linked to the bacterial cell. The skilled person will understand that the target molecule may be linked to any component of the permeabilised bacterial cell, either directly or indirectly. Direct linking may be achieved, by way of non-limiting example, by linking the target molecule to the bacterial cell wall. Indirect linking of the target molecule may be achieved, for example, by linking the target molecule to the second polypeptide that is associated with the polypeptide being screened for a desired activity to form a protein complex. For example, the target molecule may be linked to the polypeptide having a molecular size sufficient to retain the protein complex inside the permeabilised bacterial cell, or it may be linked to the DNA-binding protein, or to the bacterial cell wall-binding protein as used in the methods of the invention. Linking the target molecule to the bacterial cell advantageously enables the isolation of bacterial cells presenting active enzymes using technologies such as, for example, FACS or by magnetic bead selections.

The person skilled in the art will readily be able to determine a coupling chemistry suitable for linking a target molecule to a bacterial cell. Suitable coupling chemistries include cysteine labeling with thiol coupling reagents such as acrydite and maleimide, amine labeling, and carboxyl labeling which are commercially available from suppliers including Pierce Protein Research Products and Invitrogen.

Flow Cytometry Analysis

The cellular display technology of the present invention may present many thousands of molecules of a polypeptide of interest at once and, unlike molecular display technologies such as ribosomal/mRNA display or phage display, may be screened using flow cytometry techniques, for example using fluorescence activated cell sorting (FACS) machines. Not only can positive events in the library be captured but parameters such as enzymatic activity or affinity can be simultaneously defined for each positive member, thereby improving the output of the screen. Instruments for carrying out flow cytometry are known in the art and include FACS Star Plus, FACScan and FACSort (Becton Dickinson), Epics C, and MoFlo. Flow cytometric techniques in general involve the separation of cells in a liquid sample. Typically, the purpose of FACS is to analyse the cells for one or more characteristics, for example, the presence of a target molecule. Methods for performing flow cytometry analysis are well known in the art. For example, a review of methods using FACS for assaying enzyme activity is described by Farinas (2006).

For the present invention, flow cytometry is useful for multiple rounds of screening that can be carried out sequentially. Cells may be isolated from an initial round of sorting and immediately reintroduced into the flow cytometer and screened again to improve the stringency of the screen. Since flow cytometry is essentially a particle sorting technology, the ability to culture cells is not necessary. Techniques for the recovery of nucleic acids from non-viable cells are well known in the art and may include, for example, template-dependant amplification techniques including PCR.

After a bacterial cell has been identified that produces a polypeptide having a desired activity, DNA comprising the polynucleotide encoding the polypeptide may be isolated from the bacterial cell using any suitable known technique. Thus, the DNA encoding the polypeptide may be isolated and sequenced using conventional procedures. If desired, the polynucleotide may go through another round of diversification in order to generate another library of variants to be screened for the desired activity. In this way it is possible to use an iterative process to optimise the desired activity of a polypeptide.

Kits

The necessary components for performing the methods of the invention may conveniently be provided in the form of a kit. As will be understood to a person skilled in the art, the various components in the kit may be supplied in individual containers or aliquots, or the solution components may be combined in different combinations and at different concentrations to achieve optimal performance of the methods of the invention. It is within the knowledge of the skilled addressee to determine which components of the kit may be combined such that the components are maintained in a stable form prior to use.

The kits of the invention will typically at a minimum contain a vector which comprises a site for inserting into the vector a polynucleotide encoding a first polypeptide, and an open reading frame encoding a second polypeptide which associates with the first polypeptide to form a protein complex that is retained inside or attaches to the cell wall of a permeabilised bacterial cell. Preferably, the kit also contains an agent for permeabilising a bacterial cell. In one embodiment, the kit further comprises bacterial cells, preferably Gram negative bacterial cells. Other additional components may be included with the kit, or other components supplied by the end user, if required.

EXAMPLES

Example 1. Screening for Detergents that Permeabilise *E. coli*

To identify detergents that would permeabilise *E. coli* cells, we screened a number of detergents, both ionic (n-dodecyl-β-iminodipropionic acid; decyltrimethylammonium chloride; sodium dodecanoyl sarcosine; anzergent 3-10) and non-ionic (dimethyloctylphosphine oxide [Apo8]; dimethyldecylphosphine oxide; n-octyl-β-D-thioglucopyranoside [8TGP]; sucrose monododecanoate; Mega10; Tween 80; Triton X100; Triton X114), both for the uptake of the membrane-impermeable dye, Gel Red (Biotium, cat. no. 41002) and for the release of GFP. The detergents tested for permeabilisation were purchased from Anatrace.

The E. coli host strain used in all reported experiments was the K12-derived Argentum (Alchemy Biosciences) cell line (ΔmcrA Δ(mrr-hsdRMS-mcrBC) ΔendA lacZΔM15). However, the method of the invention was also tested, with comparable results, with the B-strain-derived BL21 (F– dcm ompT hsdS($r_B$– $m_B$–) gal) and with the K12 cloning strain DH5α (F⁻ endA1 glnV44 thi-1 recA1 relA1 gyrA96 deoR nupG Φ80dlacZΔM15 Δ(lacZYA-argF)U169, hsdR17($r_K^-$ $m_K^+$), λ–).

GFP was cloned into an arabinose-inducible, high copy-number vector (pAra1::GFP5). Expression was from a culture heavily inoculated from a plate with freshly-streaked colonies. The culture was grown at 37° C. until an OD600 of ~0.3 when expression was induced by the addition of arabinose to a final concentration of 0.2%. The induced culture was shaken at 25° C. for 2 hours before harvesting.

Cells were pelleted from 1 mL of induced culture by centrifugation and permeabilised by suspension in 300 µL, of 0.5% detergent in LB and incubated at 25° C. for 10 minutes. The permeabilised cells were pelleted and resuspended in 1× Gel Red in water for 2 minutes before being pelleted and washed once in 300 µL, of TBS. They were suspended in 300 µL, of TBS and processed for fluorescence microscopy by the addition of DABCO/glycerol (0.0325 g DABCO dissolved in 900 µl glycerol+100 µl PBS).

Samples were visualized on either an Olympus Provis AX70 Light Microscope with a Slider Camera (SPOT RT 2.3.0 Software v4.6), or a Leica TCS SP2 Confocal Scanning Laser Microscope/Leica DM IRE2 Inverted Microscope (Leica Confocal Software v2.0).

FIG. 1 shows the result of detergent permeabilisation with GFP-expressing E. coli. Whereas untreated cells are green (GFP), cells that have been permeabilised lose their internal GFP and take up the DNA-binding Gel Red dye to be stained red. While nonidet-40 shows some permeabilisation, Apo8 and Mega10 display a higher proportion of cells that have been permeabilised. A blend of these two detergents at 0.5% each, named Agent 86, demonstrated almost complete permeabilisation, as did another detergent, n-octyl-β-D-thioglucopyranoside (8TGP). Mega10, Apo8 and 8TGP are all non-ionic detergents, which are less disruptive than ionic detergents to protein folding and function.

As the cell wall remained intact following permeabilisation, soluble protein extracts of the supernatant from the detergent permeabilisation described above were analysed by SDS-PAGE. Hen egg-white lysozyme (Boehringer Mannheim; 837 059) was also added to a final concentration of 2 mg/mL to a sample of the cells being permeabilised to remove the cell wall and release the total cellular proteins. SDS-PAGE loading dye with β-mercaptoethanol was then added to the samples, which were denatured at 95° C. for 2 minutes. 20 µL, of samples were loaded onto a 9% SDS-PAGE and stained/fixed with Coomassie Brilliant Blue/methanol/acetic acid.

FIG. 2 shows that the release of soluble protein directly correlates to the release of GFP and intake of Gel Red as observed by microscopy. Significantly, there were differences between the release of protein from cells with intact cell walls compared to those whose cell walls were removed using lysozyme, with the cell-wall encapsulated cells releasing soluble protein up to a size of ~120 kD. This is presumably the cut-off size above which globular proteins are unable to leave the cell through the pores of the peptidoglycan lattice that constitutes the cell wall of gram-negative eubacteria.

Example 2. Screening for Permeabilisation Solutions that Retain Host DNA

If the method of the invention is to be used for screening gene libraries for protein variants with improved properties, there must remain a linkage between the expressed protein and its coding nucleic acid. As the membrane permeabilisation step removes the barrier that prevents DNA loss through the cell wall, conditions for permeabilisation were examined that might reduce or prevent host DNA loss.

Permeabilisation of cells using 0.5% 8TGP was conducted in different media and the loss of DNA was examined by fluorescence microscopy using the DNA-binding dye, Gel Red.

Compositions of permeabilisation media tested (all media with 0.5% 8TGP):
LB media (10 g typtone, 5 g yeast extract, 10 g NaCl per Lt)
LB [-salt] media (10 g typtone, 5 g yeast extract per Lt)
50 mM Tris, pH 7.5
50 mM Hepes, pH 7.0
170 mM NaCl
250 mM NaCl
25 mM Tris, pH 7.5+1.5% PEG 6000 (w/v)
50 mM Tris, pH 7.5+3% PEG 6000 (w/v)
50 mM Tris, pH 7.5+170 mM NaCl
50 mM Tris, pH 7.5+250 mM NaCl An optimal media for permeabilisation was identified as LB bacterial media. Accordingly, permeabilisation was henceforth conducted using either 0.5% 8TGP in LB or Agent 86 in LB (0.5% Mega10 and 0.5% Apo8 in LB).

Example 3. Protein Fusions to a Tetramer Scaffold

As was observed by the experiments reported in Example 1, proteins larger than ~120 kD in size were retained within permeabilised E. coli cells by the cell wall. Therefore, it was reasoned that a protein of interest that was smaller than 120 kD would be retained within the cell wall capsule if, by fusion to a protein partner, the total size could be made to exceed 120 kD.

Accordingly, we cloned 6 different tetrameric proteins from E. coli for use as fusion partners. These were β-gal, BetB, GSK, GshB, RhnA, and YdcW, that had monomeric sizes of 116 kD, 52 kD, 39 kD, 35 kD, 47 kD and 50 kD respectively.

An arabinose-inducible high copy vector was built for tetrameric expression. The SNAP tag (NEB/Covalys), a 20 kD domain that covalently binds a fluorescent substrate, was cloned upstream of the tetramer genes and used as a expression reporter. A 6× His epitope was also included at the N-terminus of the fusion protein to facilitate purification or detection.

The sequence of the arabinose vector, pAra3::His6::SNAP, is provided as SEQ ID NO:1.

Fusion protein expression was induced with the addition of 0.2% arabinose, and the culture incubated at 25° C. for 2 hours.

To permeabilise the cells for protein display by the method of the invention, the protocol was as follows:
1. Pellet 1 ml of cells by centrifugation
2. Resuspend cells in 300 µL of 0.5% 8TGP/LB
3. Incubate at 25° C. for 10 minutes
4. Pellet cells by centrifugation
5. Resuspend cells in 200 µL of TBS or LB To label the SNAP expression reporter domain with the membrane-impermeable SNAP dyes (Covalys/New England Biolabs), the protocol was as follows:

1. Dissolve 20 nmol of BG-488 (green dye) or BG-547 (red dye) in 300 μL DMSO as a 200× stock
2. Add 1 μL of 200× stock to 200 μL of permeabilised cells suspended in TBS or LB
3. Incubate at 25° C. for 15 minutes
4. Wash cells twice by pelleting by centrifugation and resuspending in 300 μL TBS To view the tetrameric fusion proteins by fluorescence microscopy for retention within the permeabilised cellular capsule, the protocol was as follows:
1. Drop 20 uL of cell suspension onto a glass microscope slide, cover with coverslip and seal edges with nail polish (wet mount); alternatively, allow the cell droplet to almost dry, drop 20 μL, of DABCO/glycerol on top, cover with coverslip and seal edges with nail polish (dry mount)
2. Visualise sample using either Olympus or Leica fluorescence microscope Expression of the full-length fusion protein was confirmed by Western blot of protein extracts run on SDS-PAGE gels and probed with α-His6 antibody. All tetrameric constructs expressed in E. coli at detectable levels (FIG. 3A).

Fluorescence microscopy of the tetrameric fusion proteins expressed in E. coli found that β-gal and G5K had significant inclusion bodies and low fluorescence, presumably due to difficulties in folding of the fusion protein. However, as shown by FIG. 4, expression of the fusion protein, as judged by SNAP fluorescence, was good for GshB, and excellent for RhnA, BetB and YdcW. It was noted that the distribution of the fusion protein in the permeabilised host cell was not homogeneous, with foci evident both by bright-field microscopy and fluorescence. However, as the fluorescent SNAP substrate would not be bound by a misfolded domain, and as the signal was very intense, it is thought that these bodies are likely to be aggregates of folded protein, and not inclusion bodies of unfolded protein which are frequently observed when over-expressing proteins in E. coli.

The SNAP::tetramer fusions also had a His6::N-terminal epitope. To test whether a large molecule such as an antibody would be able to penetrate through the lattice structure of the E. coli cell wall permeabilised cells were probed with αHis antibody to detect the SNAP::tetramer fusion.
1. Expression and permeabilisation of the His6::SNAP::BetB scaffold fusion was performed as described above.
2. Labeling with the BG-547 SNAP ligand was performed as described above.
3. 200 μl of permeabilised, SNAP-labeled cells were washed three times in LB and allowed to settle onto a polyethyleneimine (PEI)-coated coverslip. Excess cell media was removed by aspiration and the slides allowed to air dry.
4. Cells were blocked for one hour in blocking buffer (1% BSA, 1% cold-water fish gelatin (Sigma, G7765), 0.02% Azide in PBS-Tween20).
5. Cells were incubated overnight at 25° C. in αHis primary antibody (Abcam, AB9136-100), diluted 1:10 in blocking buffer.
6. Cells were washed 3× in PBS-Tween20 (10 min each).
7. Cells incubated in secondary antibody diluted 1:2,000 (Molecular Probes, A11015) in blocking buffer for 1 hour at room temp.
8. Cells washed 3× in PBS-Tween20.
9. Mounted in DABCO/glycerol and viewed under the confocal/Olympus microscope.

FIG. 5 shows that the αHis antibody co-localised with the SNAP fluorescent ligand within the cell wall capsule, indicating that the pores of the cell wall are wide enough to allow diffusion of a relatively large protein into the inner capsule volume. Thus, even quite large protein ligands may be used as affinity substrates for affinity proteins expressed in the cytoplasm according to the method of the invention.

The SNAP fusion partner and expression reporter was compared with the HALO protein (Promega) in an attempt to see if the formation of the sub-cellular bodies was altered. The HALO protein covalently binds a membrane-impermeable fluorescent substrate (Alexa fluor 488; G1001, Promega) similarly to SNAP. The HALO reporter gene was cloned in frame directly into the place of the SNAP gene in the tetrameric expression constructs. Expression of the HALO::tetrameric scaffold proteins was compared to the SNAP variants. Labeling of the permeabilised HALO cells was conducted essentially as described for SNAP, and following the manufacturer's instructions. FIG. 6 shows that the expression patterns of the HALO::tetramers and the SNAP::tetramers was found to be similar, with the exception that the HALO::RhnA fusion protein was fractionally more soluble than the SNAP::RhnA fusion, with fewer cells containing fluorescent foci.

Therefore, expressing a protein as a fusion to a tetrameric scaffold (in this example, SNAP or HALO), and then permeabilising the E. coli host cell with a suitable detergent enables retention of the protein of interest inside the cell wall.

Example 4. DNA Binding Proteins as a Cellular Scaffold

To couple the phenotype to genotype, the host cell must retain at least some episomal DNA following permeabilisation and throughout the functional screen. Having identified permeabilisation conditions that retained the host genomic DNA, as well as plasmid DNA, we reasoned that DNA could be used as a retaining scaffold for the expressed protein of interest.

We therefore cloned a small (80 aa) high-affinity helix-hairpin-helix DNA binding protein (DBP) from the Neisseria gonorrhoeae ComE gene (Chen and Gotschlich, 2001) and fused it to the C-terminus of GFP in an arabinose-inducible construct (pAra3::GFP::DBP; seq 2).

Expression by arabinose induction was conducted as described for Example 1. Cells were permeabilised and prepared for fluorescence microscopy as described for Examples 1 and 3.

FIG. 7 shows that the GFP::DBP fusion (green) was retained in permeabilised cells and co-localised with the DNA-binding dye, Gel Red (red).

Therefore, expressing a protein as a fusion to a high-affinity, non-specific DNA-binding protein, and then permeabilising the E. coli host cell with a suitable detergent enables retention of the protein of interest within the cellular capsule.

Example 5. DNA Retention in Permeabilised Cells

To demonstrate the retention of DNA, both genomic and episomal plasmid, within the cellular capsule following permeabilisation, we prepared cells expressing GFP5::DBP and His6::eGFP for fluorescence microscopy and plasmid DNA extraction.

Following induction, cells were permeabilised then either frozen or left in TBS at 37° C. with shaking overnight. All samples were processed the following day for either fluorescence microscopy, to visualize GFP and the capsule DNA content by the DNA-binding dye Gel Red, or a plasmid DNA preparation was conducted.

Fluorescence microscopy was performed as described for Example 3. FIG. 8 shows that both the host cell DNA (red) and the GFP5::DBP (green) were retained in the cellular capsule immediately following permeabilisation and also with overnight incubation at 37° C., without any apparent loss. The His6::GFP protein was lost from cells following permeabilisation, but the host cell DNA (red) was still retained both following permeabilisation, and also overnight, again without apparent loss.

To confirm that the plasmid DNA, and not just the host genome, was retained within the permeabilised cells, plasmid mini-preparations were conducted on identically prepared samples.

Plasmid DNA from 1 mL of detergent-treated or untreated cells was prepared by a plasmid mini-preparation alkaline lysis protocol. Plasmid DNA released into the supernatant from the detergent extraction was extracted using a Perfectprep Gel Cleanup (Eppendorf; 955152051) column and solution, following the protocol of the manufacturer.

The entire amount from each sample was loaded onto a 1% agarose gel and imaged on a FujiFilm LAS-3000 Intelligent Darkbox using Image Reader LAS-3000 software and Multi Gauge v3.0 software.

FIG. 9 shows an ethidium-bromide stained 1% agarose gel with TAE buffer with samples of plasmid DNA from both cell lines.

Lane 1 of FIG. 9 is the total plasmid DNA in untreated cells. Lane 2 is the supernatant from the permeabilisation step and Lane 3 is the plasmid retained in the cell capsule following permeabilisation. It is observed that there is very little plasmid release into the supernatant with permeabilisation, despite the complete loss of soluble His 6::GFP protein observed in FIG. 8. Therefore, plasmid DNA is almost completely retained by the cell wall and may be used in the method of the invention for the linkage of genotype to phenotype in screens for improved protein variants.

Confirming the microscopy data, the overnight incubation did not reveal any loss of plasmid DNA following overnight incubation at 37° C. of permeabilised cells suspended in TBS (lane 5).

Example 6. Peptidoglycan-Binding Scaffold

Another cellular structure that is retained following membrane permeabilisation is the cell wall, which is composed of a latticed polymer of peptidoglycan (PG).

To bind PG non-covalently, we cloned a 70 aa PG-binding domain from the *Pseudomonas* φKZ phage (KzPG) that was previously shown to be well expressed in *E. coli*, and to bind to the cell wall with high affinity (K=3×10$^7$ M-1) (Briers et al., 2009). As a screen for affinity proteins would hopefully identify variants that have even higher affinities for their targets than the KzPG-binding domain for PG, we needed to increase the affinity of the scaffold-binding protein. To increase the affinity of the scaffold-binding moiety we linked both the ComE DNA binding domain (DBD) and the PG-binding domain in the same fusion protein. Therefore, the final dissociation constant of the fusion protein from both scaffolds (PG or DNA) should be the close to a multiple of each rate constant.

We therefore constructed an expression vector pAra3::His6::KzPG::SNAP::DBP (SEQ ID NO:2). Expression was induced as described in Example 1 and cells were prepared for fluorescence microscopy as described in Example 3. Expression and distribution of the fusion protein was monitored by SNAP labeling, as described in Example 3.

Fluorescence was observed at the periphery of the cell, in the area of the cell wall, and at a lower level in a diffuse area within the cell wall-bounded volume of the capsule.

Another embodiment of the invention would be to covalently attach the protein of interest to a cellular scaffold before permeabilisation. To achieve this, we used a protein fusion to LPP, an abundant *E. coli* protein that forms a trimeric coiled-coil in the periplasm. In its native form, one end is tethered to the outer membrane via lipidation and the other is covalently bound to the cell wall via a C-terminal lysine.

We constructed an expression construct that fused the OmpF periplasmic-targeting signal sequence to the SNAP expression reporter, followed by the 57 aa *E. coli* LPP sequence lacking the N-terminal signal sequence and cysteine required for outer membrane attachment. The expression vector, pAra3::OmpF::SNAP::LPP (SEQ ID NO:3) was induced with arabinose, as described by Example 1, and cells were prepared for fluorescence microscopy as described by Example 3. Expression and distribution of the fusion protein was monitored by SNAP labeling, as described in Example 3.

FIG. 10 shows the distribution of the LPP fusion protein was uneven across the surface of the cell wall, with areas of intense fluorescence and areas absent of any fluorescence. However, in almost all instances, the poles of the cells were labeled.

Example 7. Display of an αGFP Affinity Protein Using a Tetrameric Protein Scaffold To demonstrate the method of the invention as applied to affinity proteins, a single-domain antibody generated from a Llama immunized against eGFP was cloned into the cellular scaffold vectors. It should be noted that, of the two sequences listed in the patent application for the αGFP antibody (WO 2007/068313), only the R35 variant was found to be functional (αGFP-R35; Protein Database ID 3K1K). Therefore, this sequence was used all experimental testing.

The αGFP-R35 gene was cloned as an N-terminal fusion to the pAra3::HALO::FLAG::RhnA tetrameric scaffold to create the pAra3::αGFP(R35)::HALO::FLAG::RhnA vector (SEQ ID NO:4).

A pAra3::His6::eGFP vector was also constructed to produce a His6::eGFP fusion protein as the target substrate of the antibody. The His6::eGFP protein was induced as described in Example 1. Soluble protein was released from cells using 0.5% 8TGP, was purified by IMAC using Ni-NTA agarose resin (Qiagen; 30230). His 6::eGFP was eluted from the Ni-NTA resin in NTTW buffer+imidazole (500 mM NaCl, 50 mM Tris-HCl, pH 7.5, 0.1% Tween20+200 mM imidazole).

Expression of the antibody::tetrameric fusion protein and permeabilisation of host cells was conducted as described in Example 1 and 3.

For binding of αGFP to eGFP in permeabilised cellular capsules, the capsule pellet was suspended in 300 µL, of eGFP and allowed to equilibrate for 20 minutes at 25° C., at which point the capsules were pelleted by centrifugation, washed once in 300 µL TBS, and then resuspended in TBS. Florescence microscopy on αGFP/eGFP capsules was conducted as described in Example 3.

FIG. 11 shows that the permeabilised capsules expressing αGFP::HALO::RhnA fusion protein bound eGFP throughout the cell, although there appeared to be foci of more intense staining that may correlate to the foci observed in FIG. 5 with HALO ligand labeling.

Therefore, the Llama αGFP antibody is functionally expressed in the cytoplasm and, furthermore, is retained within the capsule following detergent permeabilisation.

The αHis antibody labeling described in Example 3 and observed in FIG. 5 already demonstrated that a larger protein of ~150 kD is capable of diffusing through the permeabilised cell wall into the interior of the capsule. However, native antibodies are irregular-shaped proteins with 3 approximately equal-sized domains separated by a flexible hinge region. Thus, the effective radius that these proteins may present may be of a much smaller globular protein. However, GFP, which has a β-barrel structure and a molecular size of ~27 kD, is a symmetrical protein with a radius proportional to its size, was able to pass through the cell walls of the permeabilised capsule to be bound by the internal αGFP antibody.

Thus, the method of the invention may be used to express affinity proteins in the E. coli cytoplasm for the use in display of affinity libraries for binding symmetrical targets of at least 30 kD.

Example 8. Display of an αGFP Affinity Protein Using a PG- and DNA-Binding Protein Scaffold The method of the invention was further demonstrated using the αGFP camelid antibody fused to PG- and DNA-binding domains.

Expression of the antibody::KzPG::SNAP::DBP fusion protein, permeabilisation of host cells and labeling with His6::eGFP was conducted as described for Example 6.

Both wet and dry mounts were used to image the binding of eGFP by the αGFP fusion protein. FIG. 12 shows that there were significant differences with the GFP fluorescence between the two different imaging methods. Dry mounted (DABCO/glycerol) cells had mostly internal fluorescence, with a merge between the brightfield and eGFP labeling showing that the region around the cell wall was no more intense than the internal volume (FIG. 12B). Cells mounted directly in TBS, however, had a distinctive pattern of an outer border of strong fluorescence that appears to be the cell wall-bound eGFP with a weaker internal signal (FIG. 12A). Without being bound by theory, we speculate that the DABCO/glycerol solvent environment, being viscous and non-aqueous, prevented the interaction between the KzPG domain with the peptidoglycan cell wall, but did not prevent the binding of αGFP to eGFP, or the DBP to DNA.

However, as the screening procedures for affinity proteins or enzymes will almost always be conducted in aqueous environments, the distribution of the affinity fusion protein will approximate the observed cell wall-bound wet mount of FIG. 12A.

Example 9. Display of an αGFP Affinity Protein Through Covalent Attachment to the Cell Wall The method of the invention was further demonstrated by covalently linking the αGFP antibody to the cell wall.

The αGFP antibody was cloned as an arabinose-inducible fusion downstream from the OmpF signal sequence and upstream from the SNAP and LPP sequences.

Upon induction of expression by arabinose, the OmpF signal sequence will direct the nascent protein through the inner cell membrane into the periplasm and will be cleaved off as it passes through the membrane pore.

In the periplasm, the LPP domain is expected to form a trimeric coiled-coil with two other partners, either wild-type LPP or with other αGFP fusion proteins. The C-terminal residue of the LPP domain is a lysine that is covalently linked to the E. coli cell wall through the ε amine group, most probably by the YbiS L,D-transpeptidase (Magnet et al., 2007).

Expression of the OmpF::αGFP::SNAP::LPP fusion protein, cellular permeabilisation and eGFP labeling was performed as described for Example 8.

FIG. 13 shows that eGFP was bound unevenly, but intensely, around the cell wall (FIG. 13B). eGFP was not bound by cells expressing the OmpF::SNAP::LPP fusion without the αGFP domain (FIG. 13A).

Covalent attachment of the OmpF::SNAP::LPP fusion to the cell wall was demonstrated by first labeling permeabilised cells expressing the fusion protein with a SNAP ligand before heating a sample of the labeled cell capsules to 95° C. for 5 minutes. FIG. 14 demonstrates that the fluorescence from the SNAP ligand labeling the cell wall was unchanged between the heat-treated sample, and a control that was not heated. Gel Red staining also demonstrated that the genomic DNA was still retained in the cell, even in the heat-treated sample.

Example 10. Outer Membrane Permeabilisation Experiments

In a further embodiment of the invention, the outer membrane may be selectively permeabilised for ligand targets, such as for example enzyme substrates or polypeptides, while retaining the polypeptide that is being screened either within, or attached to, the cell wall.

To identify conditions that would selectively permeabilise the outer membrane, a range of detergents and buffers were screened. Both large (eGFP) and small (Gel Red) ligands were used to determine if the permeabilisation of the outer/inner membranes generated either large or small membrane pores.

E. coli strains expressing arabinose-inducible OmpF:: αGFP::SNAP::LPP (cell wall attached) or αGFP::HALO:: FLAG::RhnA (cytoplasmic) were grown and induced as described for Example 1.

1 mL of induced culture was washed once in 50 mM Tris (pH 8) before being suspended in permeabilisation buffer variants containing 0.2-0.4% detergent in either 25 mM Tris+1 mM EDTA (pH 8) or 25 mM Tris+2 mM $Ca^{2+}$ (pH 8) and incubated at 25° C. for 10 minutes.

Permeabilised cells were washed once in appropriate buffer and then stained with Gel Red (1× in water) and washed with TBS. They were then incubated with purified His6::eGFP for 1 hour at 25° C. before being pelleted by centrifugation and resuspended in TBS and viewed by fluorescence microscopy as a wet mount.

FIGS. 15 and 16 demonstrate that 0.2% Apo8 (A) or Tween20 (B) in either a Tris/$Ca^{2+}$ or Tris/EDTA buffer selectively permeabilised the outer membrane allowing the permeation of a large ligand (eGFP) through the outer membrane but not through the inner membrane. The smaller, membrane impermeable, DNA-binding ligand Gel Red was partially permeable to the cytoplasm in most samples, indicating that some degree of poration of the inner membrane was occurring in some cells. However, the degree of Gel Red binding was much reduced compared to samples that had been treated with the detergents 0.5% 8TGP or Agent86 where both the outer and inner membranes were fully permeable to eGFP.

Example 11. Fluorescence Sorting and Analysis of Encapsulated Display

As a cellular display platform, the method of the invention is ideally suited for fluorescence-activated cell sorting (FACS) to identify ligand-binding clones. To test the stability of permeabilised *E. coli* cells for sorting by FACS, three populations were induced for expression: i) eGFP; ii) αGFP::KzPG::SNAP::DBP; and iii) His6::SNAP::BetB.

The eGFP-expressing cells were not permeabilised, and were a positive control for fluorescence in intact *E. coli* cells. The αGFP::KzPG::SNAP::DBP expressing cells were permeabilised according to the method of the invention, and were labeled with the SNAP BG-488 ligand (green). The His6::SNAP::BetB expressing cells were permeabilised according to the method of the invention, and were labeled with the SNAP BG-547 ligand (red).

Cells were suspended in PBS and mixed in approximately equal numbers for sorting of mixed populations or sorted separately for signal calibration. Cell sorting was performed on a Becton Dickson Influx FACS. Data analysis was performed on FlowJo software. Parameters for *E. coli* sorting were determined by the operator.

FIG. 17 demonstrates that the three populations were identifiable by fluorescence. Reanalysis of the sorted populations showed that the sorting provided relatively pure populations of each. The signals present in the low-fluorescence region of the graph were later shown to be inherent noise in the signal and later removed by the operator by instrument corrections.

Example 12. Spacer Region Selection for Solid Support Binding

Cells expressing the αGFP::KzPG::SNAP::DBP fusion protein were permeabilised using 8TGP media, and cells bound to His Pur Co$^{2+}$ sepharose beads (Thermo Scientific) via an intermediate, His6-tagged eGFP. Either cells or beads were first incubated with an excess of His6-eGFP before being washed in TBS and then incubated together for 30 minutes at 25° C. Unbound cells were then washed away from the beads before the extent of bead binding was assessed by fluorescence microscopy.

Initially no binding of the αGFP::KzPG::SNAP::DBP fusion protein to sepharose beads was detected. It was theorized that the αGFP binding domain may be in too close proximity to the cell wall to reach the cobalt-complexed eGFP on the sepharose resin. Accordingly, a 12-residue peptide spacer domain with randomized codons was cloned between the αGFP binding domain and the kzPG peptidoglycan binding domain (GGT ACC gcy gcy gkk wtb gck wtb gkk gkk gck gkk gcy gcy GGT CTG (SEQ ID NO:5))

A small library (~2,000 members) of the spacer variants was expressed and then bound to Co2+ sepharose, as described above. A proportion of the library was observed to bind to the beads. These clones were then PCR amplified, re-cloned and a dozen clones were tested individually for binding and sequenced. A variety of peptide spacers were found to be both resistant to proteolytic cleavage (maintaining high levels of αGFP in the fusion protein) as well as enabling binding of the detergent-treated cells to the sepharose beads as demonstrated by FIG. 18. Spacer sequences that were found to be functional for support binding are listed in Table 1.

TABLE 1

| Random linker (RL) spacers for solid support binding | |
|---|---|
| Linker | Amino acid sequence |
| RL1 | GSNSNNQSKPSS (SEQ ID NO: 6) |
| RL2 | GGPRNPQRHTGS (SEQ ID NO: 7) |
| RL6 | SGTRHHNSHNSS (SEQ ID NO: 8) |
| RL9 | SSNRTHKSNNSS (SEQ ID NO: 9) |
| RL10 | SGHRTTERKHSS (SEQ ID NO: 10) |
| RL13 | GGHRHTQRHNGG (SEQ ID NO: 11) |
| RL14 | GGPRTPQSQPSG (SEQ ID NO: 12) |

One spacer sequence, RL6, was chosen for further binding studies. Other factors contributing to strong binding to solid support matrixes were examined. The length of time for incubation of the cells with the matrix and the salt (NaCl) concentration of the binding solution were both found to have positive effects on binding. Incubation lengths of 30 minutes and a range of NaCl concentrations from ~200 mM to 500 mM were found to be effective although 300 mM was considered optimal. Binding was effective in a range of buffers, including Tris, phosphate and MOPS buffered solutions with 300 mM salt.

Conditions of binding for cells expressing the αGFP::RL6::KzPG::SNAP::DBP fusion protein to streptavadin magnetic nanoparticles (MagneSphere; Roche diagnostics) via biotinylated eGFP were also confirmed as being within the ranges identified for sepharose bead binding and demonstrated by FIG. 19.

In addition to the 12-residue spacers, protein domains were also considered for use as spacer domains. The small, stable and highly-expressed 27$^{th}$ immunoglobin domain from the human titin gene (I27) was cloned upstream from the RL6 spacer. This domain was also found to enable high and stable expression of the N-terminal αGFP domain as well as excellent solid matrix binding (FIG. 19).

Example 13. Construction of a Mouse scFv Library for Encapsulated Display

The final domain structure for the intracellular display of a single-chain antibody (scFv) library was: scFv::I27::RL6::KzPG::SNAP::DBP. The protein and DNA sequences of the fusion protein without the scFv domain are provided as SEQ ID NO:13 and SEQ ID NO:14. This protein fusion has the scFv at the N-terminus, followed by the two spacer domains, I27 and RL6, then the peptidoglycan binding domain, KzPG, the SNAP reporter domain and, finally, the DNA binding domain (DBP).

Random-primed cDNA was produced from mouse spleen total RNA using the Superscript 111 (Invitrogen) enzyme. From this cDNA, the scFv light ($V_L$) and heavy ($V_H$) chain variable domains were amplified using Vent DNA polymerase (New England Biolabs) and degenerate oligonucleotide primers for the mouse antibody family sequences, as described by Schaefer et al. (2010). The oligonucleotide primers used for library cloning differed from those described by Schaefer et al. in that they had appropriate ends for cloning via Bsm BI into our library scaffold vector (SEQ ID NO:15). The VL and VH domains were joined using overlapping extension PCR. The final scFv band had been subjected to a total of 60 PCR amplification cycles (30 first round, 30 second round).

For library cloning, 900 ng of the display construct was cut with BsmBI, precipitated using Sureclean (Bioline) according to the manufacturer's instructions, and ligated using T4 DNA ligase to 400 ng of similarly-treated scFv product. The ligase was killed by incubation at 65° C. for 10 minutes and the ligation electroporated into the *E. coli* Argentum strain (Alchemy Biosciences). The electroporated cells were recovered in SOC media and incubated for 1 hour at 37° C. before pooling and then spread across 20×150 mm LB agar plates with 75 ug/mL ampicillin. The plates were incubated overnight at 30° C. The library size was estimated at $4 \times 10^5$ independent clones. 20 out of 20 colonies were found to contain an insert of the expected size.

Example 14. Screening of an Encapsulated Display Mouse scFv Library

Single chain antibodies isolated from phage display libraries are often difficult to express in *E. coli*, with either low levels of expression in the periplasm, or are completely insoluble in the cytoplasm due to the lack of disulphide bond formation between the B-sheets of the Ig fold. To determine whether encapsulated display could be used to select for a mouse scFv scaffold that would be soluble in the *E. coli* cytoplasm, it was necessary to determine whether scFv solubility was correlated with the behavior of the fusion protein.

It was predicted that a useful soluble scFv would have low levels of aggregation and at least a moderate level of expression. This could be judged visually as a clone that allowed binding of the KzPG domain in a permeabilised cell to the cell wall (and not therefore, localized to an inclusion body within the cell) and that showed at least moderate expression of the SNAP reporter domain.

To screen for these parameters, single colonies were picked and induced for fusion protein expression using arabinose as described previously for Example 1. Following permeabilisation they were labeled with SNAP ligand and viewed using fluorescence microscopy. We characterised the library clones into four categories based on their expression and cellular distribution of SNAP reporter, examples of which can be seen in FIG. 20.
1) no expression of SNAP
2) moderate/high expression of SNAP in aggregated inclusion bodies (FIG. 20, left panel)
3) weak expression of SNAP with cell wall localization (FIG. 20, mid panel)
4) high expression of SNAP with cell wall localization (FIG. 20, right panel)

Only clones with both high expression and solubility were analysed further. However, as the weak expression of the SNAP reporter could be due to inefficient expression of a protein not optimized for *E. coli* expression it is expected that a proportion of these clones would prove to be excellent for soluble cytoplasmic library display if their codon usage were optimised.

Clones with high expression of the SNAP reporter and an even distribution around the cell wall of permeabilised cells were sequenced to confirm the presence of a scFv insert that was in the correct translation frame with the remainder of the fusion protein. In all 21 clones analysed, the scFv insert was found to be full length, with the correct length of the glycine/serine linker region, and in the correct reading frame for translation of the entire fusion protein. This suggested that the method of screening of the invention was correctly identifying mouse scFv genes that were expressed in a soluble form in the cytoplasm of *E. coli* cells. To confirm that the scFv proteins isolated from the library were soluble in the *E. coli* cytoplasm they were shuttled from the library construct to an arabinose-inducible expression vector with a C-terminal FLAG epitope with an intervening spacer region of either I27-RL6 or RL6.

Following induction of protein expression by arabinose, the soluble scFv::I27::RL6::FLAG or scFv::RL6::FLAG fusion proteins were extracted with 0.5% 8TGP. The insoluble cellular material was pelleted and resuspended in SDS-PAGE loading buffer with β-mercaptoethanol by sonication of the sample and heated to 95° C. for 5 minutes. Equal volumes of each fraction were loaded onto 10% SDS-PAGE gels and electrophoresed. Separated proteins were transferred to nitrocellulose membranes, which were then blocked with 5% skim milk powder. Recombinant protein expression was probed using a 1:1000 dilution of a sheep αFLAG antibody (Sigma) followed by an anti-mouse-HRP conjugated secondary antibody. Detection was using chemilumesence.

FIG. 21 demonstrates that the method of the invention is capable of identifying scFv genes that are expressed in a mostly soluble form within the bacterial cytoplasm. The Western blot of the expression profiles is matched in each sample with the fluorescence microscopy detected by SNAP ligand for the scFv::I27::RL6::FLAG construct.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

All publications discussed and/or referenced herein are incorporated herein in their entirety.

The present application claims priority from AU 2009906310, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Aharoni et al. (2005) Chem Biol, 12:1281-1289
Becker et al. (2004) Curr Opin Biot, 15:323-329
Briers et al. (2009) Biochem Biophys Res Comm, 383:187-191
Chen and Gotschlich (2001) J Bact, 183: 3160-3168
Daugherty et al. (2000) J Immunol Methods, 243:211-227
Farinas (2006) Comb Chem High Thro Screen, 9:321-328
George, et al. (2003) Protein Engineering, 15:871-879
Kenrick et al. (2007) Curr Prot Cyt, 4.6.1-4.6.27
Lutz and Patrick (2004) Curr Opin Biot, 15:291-297
Magnet et al. (2007) J Bact 189:3927-3931
Miller et al. (2006) Nat Meth, 3:561-570
Parsons et al. (2006) Biochem 45:2122-2128
Schaefer et al. (2010) Antibody Eng, 1:21-44
Smith (1985) Science, 228:1315-1317

The invention claimed is:

1. A method of screening a polypeptide for a desired activity against a target molecule, the method comprising:
   a) culturing a gram negative bacterial cell comprising a polynucleotide encoding the polypeptide such that the polypeptide is produced, folded and localized in the cytoplasm,
   b) permeabilising the bacterial cell with a non-ionic detergent or organic solvent, wherein the polypeptide and polynucleotide encoding the polypeptide are retained inside the permeabilised bacterial cell,
   c) contacting the permeabilised bacterial cell with the target molecule such that the target molecule diffuses into the permeabilised bacterial cell, and
   d) screening the polypeptide for the desired activity.

2. The method of claim 1, wherein said screening in step d) comprises:
   i) determining if the polypeptide binds, and/or the extent of binding to, the target molecule, and/or
   ii) determining if the polypeptide enzymatically modifies, and/or the rate of enzymatic modification of, the target molecule.

3. The method of claim 1 which further comprises e) isolating DNA comprising the polynucleotide encoding the polypeptide from the permeabilised bacterial cell.

4. The method of claim 3 which further comprises f) determining the sequence of the polynucleotide encoding the polypeptide.

5. The method of claim 1, wherein the polypeptide is an antibody or enzyme.

6. The method of claim 5, wherein the antibody is a single-chain variable fragment (scFV).

7. The method of claim 5, wherein the polypeptide is an enzyme and the method comprises linking the target molecule to the permeabilised bacterial cell.

\* \* \* \* \*

SEQUENCE LISTING

<160> NUMBER OF SEQ ID NOS: 16

<210> SEQ ID NO 1
<211> LENGTH: 4641
<212> TYPE: DNA
<213> ORGANISM: Artificial Sequence
<220> FEATURE:
<223> OTHER INFORMATION: Vector

<400> SEQUENCE: 1

| | | | | | |
|---|---|---|---|---|---|
| ggttttcgc | cctttgacgt | tggagtccac | gttctttaat | agtggactct | tgttccaaac | 60 |
| tggaacaaca | ctcaaccta | tctcggtcta | ttcttttgat | ttataaggga | ttttgccgat | 120 |
| ttcggcctat | tggttaaaaa | atgagctgat | ttaacaaaaa | tttaacgcga | attttaacaa | 180 |
| aatattaacg | cttacaattt | aggtggcact | tttcggggaa | atgtgcgcgg | aaccccctatt | 240 |
| tgtttatttt | tctaaataca | ttcaaatatg | tatccgctca | tgagacaata | accctgataa | 300 |
| atgcttcaat | aatattgaaa | aaggaagagt | atgagtattc | aacatttccg | tgtcgccctt | 360 |
| attccctttt | ttgcggcatt | ttgccttcct | gttttgctc | acccagaaac | gctggtgaaa | 420 |
| gtaaaagatg | ctgaagatca | gttgggtgca | cgagtgggtt | acatcgaact | ggatctcaac | 480 |
| agcggtaaga | tccttgagag | ttttcgcccc | gaagaacgtt | ttccaatgat | gagcactttt | 540 |
| aaagttctgc | tatgtggcgc | ggtattatcc | cgtattgacg | ccgggcaaga | gcaactcggt | 600 |
| cgccgcatac | actattctca | gaatgacttg | gttgagtact | caccagtcac | agaaaagcat | 660 |
| cttacggatg | gcatgacagt | aagagaatta | tgcagtgctg | ccataaccat | gagtgataac | 720 |
| actgcggcca | acttacttct | gacaacgatc | ggaggaccga | aggagctaac | cgcttttttg | 780 |
| cacaacatgg | gggatcatgt | aactcgcctt | gatcgttggg | aaccggagct | gaatgaagcc | 840 |
| ataccaaacg | acgagcgtga | caccacgatg | cctgtagcaa | tggcaacaac | gttgcgcaaa | 900 |
| ctattaactg | gcgaactact | tactctagct | tcccggcaac | aattaataga | ctggatggag | 960 |
| gcggataaag | ttgcaggacc | acttctgcgc | tcggcccttc | cggctggctg | gtttattgct | 1020 |
| gataaatctg | gagccggtga | gcgtgggtct | cgcggtatca | ttgcagcact | ggggccagat | 1080 |
| ggtaagccct | cccgtatcgt | agttatctac | acgacgggga | gtcaggcaac | tatggatgaa | 1140 |
| cgaaatagac | agatcgctga | gataggtgcc | tcactgatta | agcattggta | actgtcagac | 1200 |
| caagtttact | catatatact | ttagattgat | ttaaaacttc | atttttaatt | taaaaggatc | 1260 |
| taggtgaaga | tcctttttga | taatctcatg | accaaaatcc | cttaacgtga | gttttcgttc | 1320 |
| cactgagcgt | cagaccccgt | agaaaagatc | aaaggatctt | cttgagatcc | ttttttttctg | 1380 |
| cgcgtaatct | gctgcttgca | aacaaaaaaa | ccaccgctac | cagcggtggt | ttgtttgccg | 1440 |
| gatcaagagc | taccaactct | ttttccgaag | gtaactggct | tcagcagagc | gcagatacca | 1500 |
| aatactgtcc | ttctagtgta | gccgtagtta | ggccaccact | tcaagaactc | tgtagcaccg | 1560 |
| cctacatacc | ccgctctgct | aatcctgtta | ccagtggctg | ctgccagtgg | cgataagtcg | 1620 |
| tgtcttaccg | ggttggactc | aagacgatag | ttaccggata | aggcgcagcg | gtcgggctga | 1680 |
| acggggggtt | cgtgcacaca | gcccagcttg | gagcgaacga | cctacaccga | actgagatac | 1740 |
| ctacagcgtg | agctatgcga | aagcgccacg | cttcccgaag | ggagaaaggc | ggacaggtat | 1800 |
| ccggtaagcg | gcagggtcgg | agcaggagag | cgcacgaggg | agcttccagg | gggaaacgcc | 1860 |
| tggtatcttt | atagtcctgt | cgggtttcgc | cacctctgac | ttgagcgtcg | atttttgtga | 1920 |
| tgctcgtcag | gggggcggag | cctatggaaa | aacgccagca | acgcggcctt | tttacggttc | 1980 |
| ctggccttt | gctggccttt | tgctcacatg | ttctttcctg | cgttatcccc | tgattctgtg | 2040 |

```
gataaccgta ttaccgcctt tgagtgagct gataccgctc gccgcagccg aacgaccgag    2100
cgcagcgagt cagtgagcga ggaagcggaa gagcgcccaa tacgcaaacc gcctctcccc    2160
gcgcgtggcc gttcattaat gcagctggca cgacaggttt cccgactgcg gccgcgacac    2220
ggaaatgttg aatactcata ctcttccttt ttcaatatta ttgaagcatt tatcagggtt    2280
attgtctcat gagcggatac atatttgaat gtatttagaa aaataaacaa ataggggttc    2340
cgcgcacatt tccccgaaaa gtgccacctg catcgattta ttatgacaac ttgacggcta    2400
catcattcac ttttttcttca caaccggcac ggaactcgct cgggctggcc ccggtgcatt    2460
ttttaaatac ccgcgagaaa tagagttgat cgtcaaaacc aacattgcga ccgacggtgg    2520
cgataggcat ccgggtggtg ctcaaaagca gcttcgcctg gctgatacgt tggtcctcgc    2580
gccagcttaa gacgctaatc cctaactgct ggcggaaaag atgtgacaga cgcgacggcg    2640
acaagcaaac atgctgtgcg acgctggcga tatcaaaatt gctgtctgcc aggtgatcgc    2700
tgatgtactg acaagcctcg cgtacccgat tatccatcgg tggatggagc gactcgttaa    2760
tcgcttccat gcgccgcagt aacaattgct caagcagatt tatcggcagc agctccgaat    2820
agcgcccttc cccttgcccg gcgttaatga tttgcccaaa caggtcgctg aaatgcggct    2880
ggtgcgtttc atccgggcga agaaccccg tattggcaaa tattgacggc cagttaagcc    2940
attcatgcca gtaggcgcgc ggacgaaagt aaacccactg gtgataccat cgcgagcct    3000 ccggatgacg accgtagtga tgaatctctc ctggcgggaa cagcaaaata tcacccggtc    3060
ggcaaacaaa ttctcgtccc tgattttca ccacccctg accgcgaatg gtgagattga    3120
gaatataacc tttcattccc agcggtcggt cgataaaaaa atcgagataa ccgttggcct    3180
caatcggcgt taaacccgcc accagatggg cattaaacga gtatcccggc agcaggggat    3240
cattttgcgc ttcagccata cttttcatac tcccgccatt cagagaagaa accaattgtc    3300
catattgcat caaacattgc cgtcactgcg tcttttactg gctcttctcg ctaaccaaac    3360
cggtaacccc gcttattaaa agcattctgt aacaaagcgg gaccaaagcc atgacaaaaa    3420
cgcgtaacaa aagtgtctat aatcacggca gaaaagtcca cattgattat ttgcacggcg    3480
tcacactttg ctatgccata gcatttttat ccataagatt agcggatcct acctgacgct    3540
ttttatcgca actctctact gtttctccat acccgttttt ttggtaagga ggttatctag    3600
aatgcaccat caccatcacc acggcgcgcc taacctcgag ggtacctcca tggacaaaga    3660
ttgcgaaatg aaacgtacca ccctggatag ccgctgggc aaactggaac tgagcggctg    3720
cgaacagggc ctgcatgaaa ttaaactgct gggtaaaggc accagcgcgg ccgatgcggt    3780
tgaagttccg gccccggccg ccgtgctggg tggtccggaa ccgctgatgc aggcgaccgc    3840
gtggctgaac gcgtattttc atcagccgga agcgattgaa gaatttccgg ttccggcgct    3900
gcatcatccg gtgtttcagc aggagagctt taccgtcag gtgctgtgga aactgctgaa    3960
agtggttaaa tttggcgaag tgattagcta tcagcagctg gcggccctgg cgggtaatcc    4020
ggcggccacc gccgccgtta aaaccgcgct gagcggtaac ccggtgccga ttctgattcc    4080
gtgccatcgt gtggttagct ctagcggtgc ggttggcggt tatgaaggtg gtctggcggt    4140
gaaagagtgg ctgctggccc atgaaggtca tcgtctgggt aaaccgggtc tgggacctgc    4200
agggtaaaag cttgaattcg cgcgctcact ggccgtcgtt ttacaacgtc gtgactggga    4260
aaaccctggc gttacccaac ttaatcgcct tgcagcacat ccccctttcg ccagctggcg    4320
taatagcgaa gaggcccgca ccgatcgccc ttcccaacag ttgcgcagcc tgaatggcga    4380
```

| | |
|---|---|
| atgggacgcg ccctgtagcg gcgcattaag cgcggcgggt gtggtggtta cgcgcagcgt | 4440 |
| gaccgctaca cttgccagcg ccctagcgcc cgctccttc gctttcttcc cttcctttct | 4500 |
| cgccacgttc gccggctttc cccgtcaagc tctaaatcgg gggctccctt tagggttccg | 4560 |
| atttagtgct ttacggcacc tcgaccccaa aaaacttgat tagggtgatg gttcacgtag | 4620 |
| tgggccatcg ccctgataga c | 4641 |

<210> SEQ ID NO 2
<211> LENGTH: 5082
<212> TYPE: DNA
<213> ORGANISM: Artificial Sequence
<220> FEATURE:
<223> OTHER INFORMATION: Vector

<400> SEQUENCE: 2

| | |
|---|---|
| ggttttcgc cctttgacgt tggagtccac gttctttaat agtggactct tgttccaaac | 60 |
| tggaacaaca ctcaaccta tctcggtcta ttcttttgat ttataaggga ttttgccgat | 120 |
| ttcggcctat tggttaaaaa atgagctgat ttaacaaaaa tttaacgcga attttaacaa | 180 |
| aatattaacg cttacaattt aggtggcact tttcggggaa atgtgcgcgg aacccctatt | 240 |
| tgtttatttt tctaaataca ttcaaatatg tatccgctca tgagacaata accctgataa | 300 |
| atgcttcaat aatattgaaa aaggaagagt atgagtattc aacatttccg tgtcgccctt | 360 |
| attccctttt ttgcggcatt ttgccttcct gttttgctc acccagaaac gctggtgaaa | 420 |
| gtaaaagatg ctgaagatca gttgggtgca cgagtgggtt acatcgaact ggatctcaac | 480 |
| agcggtaaga tccttgagag ttttcgcccc gaagaacgtt ttccaatgat gagcactttt | 540 |
| aaagttctgc tatgtggcgc ggtattatcc cgtattgacg ccgggcaaga gcaactcggt | 600 |
| cgccgcatac actattctca gaatgacttg gttgagtact caccagtcac agaaaagcat | 660 |
| cttacggatg gcatgacagt aagagaatta tgcagtgctg ccataaccat gagtgataac | 720 |
| actgcggcca acttacttct gacaacgatc ggaggaccga aggagctaac cgcttttttg | 780 |
| cacaacatgg gggatcatgt aactcgcctt gatcgttggg aaccggagct gaatgaagcc | 840 |
| ataccaaacg acgagcgtga caccacgatg cctgtagcaa tggcaacaac gttgcgcaaa | 900 |
| ctattaactg gcgaactact tactctagct tcccggcaac aattaataga ctggatggag | 960 |
| gcggataaag ttgcaggacc acttctgcgc tcggcccttc cggctggctg gtttattgct | 1020 |
| gataaatctg gagccggtga gcgtgggtct cgcggtatca ttgcagcact ggggccagat | 1080 |
| ggtaagccct cccgtatcgt agttatctac acgacgggga gtcaggcaac tatggatgaa | 1140 |
| cgaaatagac agatcgctga gataggtgcc tcactgatta agcattggta actgtcagac | 1200 |
| caagtttact catatatact ttagattgat ttaaaacttc atttttaatt taaaaggatc | 1260 |
| taggtgaaga tcctttttga taatctcatg accaaaatcc cttaacgtga gttttcgttc | 1320 |
| cactgagcgt cagacccgt agaaaagatc aaaggatctt cttgagatcc ttttttctg | 1380 |
| cgcgtaatct gctgcttgca acaaaaaaa ccaccgctac cagcggtggt ttgtttgccg | 1440 |
| gatcaagagc taccaactct ttttccgaag gtaactggct tcagcagagc gcagatacca | 1500 |
| aatactgtcc ttctagtgta gccgtagtta ggccaccact tcaagaactc tgtagcaccg | 1560 |
| cctacatacc ccgctctgct aatcctgtta ccagtggctg ctgccagtgg cgataagtcg | 1620 |
| tgtcttaccg ggttggactc aagacgatag ttaccggata aggcgcagcg gtcgggctga | 1680 |
| acgggggggtt cgtgcacaca gcccagcttg gagcgaacga cctacaccga actgagatac | 1740 |
| ctacagcgtg agctatgcga aagcgccacg cttcccgaag ggagaaaggc ggacaggtat | 1800 |

```
ccggtaagcg gcagggtcgg agcaggagag cgcacgaggg agcttccagg gggaaacgcc    1860
tggtatcttt atagtcctgt cgggtttcgc cacctctgac ttgagcgtcg attttttgtga   1920 tgctcgtcag gggggcggag cctatggaaa aacgccagca acgcggcctt tttacggttc    1980
ctggcctttt gctggccttt tgctcacatg ttctttcctg cgttatcccc tgattctgtg    2040
gataaccgta ttaccgcctt tgagtgagct gataccgctc gccgcagccg aacgaccgag    2100
cgcagcgagt cagtgagcga ggaagcggaa gagcgcccaa tacgcaaacc gcctctcccc    2160
gcgcgtggcc gttcattaat gcagctggca cgacaggttt cccgactgcg gccgcgacac    2220
ggaaatgttg aatactcata ctcttccttt tcaatatta ttgaagcatt tatcagggtt     2280
attgtctcat gagcggatac atatttgaat gtatttagaa aaataaacaa ataggggttc    2340
cgcgcacatt tccccgaaaa gtgccacctg catcgattta ttatgacaac ttgacggcta    2400
catcattcac ttttcttca caaccggcac ggaactcgct cgggctggcc ccggtgcatt     2460
ttttaaatac ccgcgagaaa tagagttgat cgtcaaaacc aacattgcga ccgacggtgg    2520
cgataggcat ccgggtggtg ctcaaaagca gcttcgcctg gctgatacgt tggtcctcgc    2580
gccagcttaa gacgctaatc cctaactgct ggcggaaaag atgtgacaga cgcgacggcg    2640
acaagcaaac atgctgtgcg acgctggcga tatcaaaatt gctgtctgcc aggtgatcgc    2700
tgatgtactg acaagcctcg cgtacccgat tatccatcgg tggatggagc gactcgttaa    2760
tcgcttccat gcgccgcagt aacaattgct caagcagatt tatcggcagc agctccgaat    2820
agcgcccttc cccttgcccg gcgttaatga tttgcccaaa caggtcgctg aaatgcggct    2880
ggtgcgtttc atccgggcga agaaccccg tattggcaaa tattgacggc cagttaagcc     2940
attcatgcca gtaggcgcgc ggacgaaagt aaacccactg gtgataccat cgcgagcct    3000 ccggatgacg accgtagtga tgaatctctc ctggcgggaa cagcaaaata tcacccggtc    3060
ggcaaacaaa ttctcgtccc tgatttttca ccaccccctg accgcgaatg gtgagattga    3120
gaatataacc tttcattccc agcggtcggt cgataaaaaa atcgagataa ccgttggcct    3180
caatcggcgt taaacccgcc accagatggg cattaaacga gtatcccggc agcaggggat    3240
cattttgcgc ttcagccata cttttcatac tcccgccatt cagagaagaa accaattgtc    3300
catattgcat caaacattgc cgtcactgcg tcttttactg gctcttctcg ctaaccaaac    3360
cggtaacccc gcttattaaa agcattctgt aacaaagcgg gaccaaagcc atgacaaaaa    3420
cgcgtaacaa aagtgtctat aatcacggca gaaaagtcca cattgattat ttgcacggcg    3480
tcacactttg ctatgccata gcatttttat ccataagatt agcggatcct acctgacgct    3540
ttttatcgca actctctact gtttctccat acccgttttt ttggtaagga ggttatctag    3600
aggtaccaac agcccaccga aagtgttacg caagggtgat cgtggcgatg aagtgtgcca    3660
gctgcaaacg ttactgaatc tctgcggtta tgacgttggc aaacctgatg gcattttcgg    3720
caataacacc ttcaaccagg ttgtgaaatt ccagaaggac aactgtttag acagcgatgg    3780
tattgtgggt aaaaacacgt gggcagaact gttcagcaaa tactcgccac cgtccatgga    3840
caaagattgc gaaatgaaac gtaccaccct ggatagcccg ctgggcaaac tggaactgag    3900
cggctgcgaa cagggcctgc atgaaattaa actgctgggg aaaggcacca gcgcggccga    3960
tgcggttgaa gttccggccc cggccgccgt gctgggtggt ccggaaccgc tgatgcaggc    4020
gaccgcgtgg ctgaacgcgt attttcatca gccggaagcg attgaagaat tccggttcc     4080 ggcgctgcat catccggtgt ttcagcagga gagctttacc cgtcaggtgc tgtggaaact    4140
```

```
gctgaaagtg gttaaatttg gcgaagtgat tagctatcag cagctggcgg ccctggcggg    4200
taatccggcg gccaccgccg ccgttaaaac cgcgctgagc ggtaacccgg tgccgattct    4260
gattccgtgc catcgtgtgg ttagctctag cggtgcggtt ggcggttatg aaggtggtct    4320
ggcggtgaaa gagtggctgc tggcccatga aggtcatcgt ctgggtaaac cgggtctggg    4380
acctgcaggg aactcaggta aaggcgcagt gaacattaac gccgcatcac agcaagaact    4440
ggaggcgtta ccgggtattg gccctgcaaa ggccaaagcg atcgctgaat atcgcgcaca    4500
aaatggcgca ttcaagagcg tcgacgatct gatcaaagtc aagggcatcg tccggcagt    4560
gctagccaag ctgaaagacc aggcatcagt tggtgcaccg gctcctaaag gtccggccaa    4620
accggtcctg cccgctgtaa agaaattaaa gcttgaattc gcgcgctcac tggccgtcgt    4680
tttacaacgt cgtgactggg aaaaccctgg cgttacccaa cttaatcgcc ttgcagcaca    4740
tccccctttc gccagctggc gtaatagcga agaggcccgc accgatcgcc cttcccaaca    4800
gttgcgcagc ctgaatggcg aatgggacgc gccctgtagc ggcgcattaa gcgcggcggg    4860
tgtggtggtt acgcgcagcg tgaccgctac acttgccagc gccctagcgc ccgctccttt    4920
cgctttcttc ccttcctttc tcgccacgtt cgccggcttt ccccgtcaag ctctaaatcg    4980
ggggctccct ttagggttcc gatttagtgc tttacggcac ctcgacccca aaaaacttga    5040
ttagggtgat ggttcacgta gtgggccatc gccctgatag ac                      5082

<210> SEQ ID NO 3
<211> LENGTH: 4855
<212> TYPE: DNA
<213> ORGANISM: Artificial Sequence
<220> FEATURE:
<223> OTHER INFORMATION: Vector
<400> SEQUENCE: 3
ggttttcgc cctttgacgt tggagtccac gttctttaat agtggactct tgttccaaac      60
tggaacaaca ctcaacccta tctcggtcta ttcttttgat ttataaggga ttttgccgat    120
ttcggcctat tggttaaaaa atgagctgat ttaacaaaaa tttaacgcga attttaacaa    180
aatattaacg cttacaattt aggtggcact tttcggggaa atgtgcgcgg aaccnctatt    240
tgtttatttt tctaaataca ttcaaatatg tatccgctca tgagacaata accctgataa    300
atgcttcaat aatattgaaa aaggaagagt atgagtattc aacatttccg tgtcgccctt    360
attcccttt ttgcggcatt ttgccttcct gtttttgctc acccagaaac gctggtgaaa     420
gtaaaagatg ctgaagatca gttgggtgca cgagtgggtt acatcgaact ggatctcaac    480
agcggtaaga tccttgagag ttttcgcccc gaagaacgtt ttccaatgat gagcactttt    540
aaagttctgc tatgtggcgc ggtattatcc cgtattgacg ccgggcaaga gcaactcggt    600
cgccgcatac actattctca gaatgacttg gttgagtact caccagtcac agaaaagcat    660
cttacggatg gcatgacagt aagagaatta tgcagtgctg ccataaccat gagtgataac    720
actgcggcca acttacttct gacaacgatc ggaggaccga aggagctaac cgcttttttg    780
cacaacatgg ggatcatgt aactcgcctt gatcgttggg aaccggagct gaatgaagcc     840
ataccaaacg acgagcgtga caccacgatg cctgtagcaa tggcaacaac gttgcgcaaa    900
ctattaactg gcgaactact tactctagct tcccggcaac aattaataga ctggatggag    960
gcggataaag ttgcaggacc acttctgcgc tcggcccttc cggctggctg gtttattgct   1020
gataaatctg gagccggtga gcgtgggtct cgcggtatca ttgcagcact ggggccagat   1080
ggtaagccct cccgtatcgt agttatctac acgacgggga gtcaggcaac tatggatgaa   1140
```

```
cgaaatagac agatcgctga gataggtgcc tcactgatta agcattggta actgtcagac    1200
caagtttact catatatact ttagattgat ttaaaacttc attttaatt taaaaggatc    1260 taggtgaaga tccttttga taatctcatg accaaaatcc cttaacgtga gttttcgttc    1320
cactgagcgt cagaccccgt agaaaagatc aaaggatctt cttgagatcc ttttttctg    1380 cgcgtaatct gctgcttgca acaaaaaaa ccaccgctac cagcggtggt ttgtttgccg    1440
gatcaagagc taccaactct ttttccgaag gtaactggct tcagcagagc gcagatacca    1500
aatactgtcc ttctagtgta gccgtagtta ggccaccact tcaagaactc tgtagcaccg    1560
cctacatacc cgctctgct aatcctgtta ccagtggctg ctgccagtgg cgataagtcg    1620
tgtcttaccg ggttggactc aagacgatag ttaccggata aggcgcagcg gtcgggctga    1680 acgggggtt cgtgcacaca gcccagcttg gagcgaacga cctacaccga actgagatac    1740
ctacagcgtg agctatgcga aagcgccacg cttcccgaag ggagaaaggc ggacaggtat    1800
ccggtaagcg gcagggtcgg agcaggagag cgcacgaggg agcttccagg gggaaacgcc    1860
tggtatcttt atagtcctgt cgggtttcgc cacctctgac ttgagcgtcg attttgtga    1920 tgctcgtcag gggggcggag cctatggaaa aacgccagca acgcggcctt tttacggttc    1980
ctggcctttt gctggccttt tgctcacatg ttctttcctg cgttatcccc tgattctgtg    2040
gataaccgta ttaccgcctt tgagtgagct gataccgctc gccgcagccg aacgaccgag    2100
cgcagcgagt cagtgagcga ggaagcggaa gagcgcccaa tacgcaaacc gcctctcccc    2160 gcgcgttggcc gttcattaat gcagctggca cgacaggttt cccgactgcg gccgcgacac    2220
ggaaatgttg aatactcata ctcttccttt ttcaatatta ttgaagcatt tatcagggtt    2280
attgtctcat gagcggatac atatttgaat gtatttagaa aaataaacaa atagggtc    2340 cgcgcacatt tccccgaaaa gtgccacctg catcgattta ttatgacaac ttgacggcta    2400
catcattcac tttttcttca aaccggcac ggaactcgct cgggctggcc ccggtgcatt    2460
ttttaaatac ccgcgagaaa tagagttgat cgtcaaaacc aacattgcga ccgacggtgg    2520
cgataggcat ccgggtggtg ctcaaaagca gcttcgcctg gctgacgt tggtcctcgc    2580 gccagcttaa gacgctaatc cctaactgct ggcggaaaag atgtgacaga cgcgacggcg    2640
acaagcaaac atgctgtgcg acgctggcga tatcaaaatt gctgtctgcc aggtgatcgc    2700
tgatgtactg acaagcctcg cgtacccgat tatccatcgg tggatggagc gactcgttaa    2760
tcgcttccat cgccgcagt aacaattgct caagcagatt tatcggcagc agctccgaat    2820
agcgcccttc cccttgcccg gcgttaatga tttgcccaaa caggtcgctg aaatgcggct    2880
ggtgcgtttc atccgggcga aagaacccg tattggcaaa tattgacggc cagttaagcc    2940
attcatgcca gtaggcgcgc ggacgaaagt aaacccactg gtgataccat tcgcgagcct    3000
ccggatgacg accgtagtga tgaatctctc ctggcgggaa cagcaaaata tcacccggtc    3060
ggcaaacaaa ttctcgtccc tgatttttca ccacccctg accgcgaatg gtgagattga    3120
gaatataacc tttcattccc agcggtcggt cgataaaaaa atcgagataa ccgttggcct    3180
caatcggcgt taaacccgcc accagatggg cattaaacga gtatcccggc agcagggat    3240 cattttgcgc ttcagccata cttttcatac tcccgccatt cagagaagaa accaattgtc    3300
catattgcat caaacattgc cgtcactgcg tcttttactg gctcttctcg ctaaccaaac    3360
cggtaacccc gcttattaaa agcattctgt aacaaagcgg gaccaaagcc atgacaaaaa    3420
cgcgtaacaa aagtgtctat aatcacggca gaaaagtcca cattgattat ttgcacggcg    3480
```

```
tcacactttg ctatgccata gcattttat  ccataagatt agcggatcct acctgacgct   3540
ttttatcgca actctctact gtttctccat acccgttttt ttggtaagga ggttatctag   3600
catgatgaag cgcaatattc tggcagtgat cgtccctgct ctgttagtag caggtactgc   3660
aaacgctgcc gaatctagac tcgagggtac ctccatggac aaagattgcg aaatgaaacg   3720
taccaccctg atagcccgc  tgggcaaact ggaactgagc ggctgcgaac agggcctgca   3780
tgaaattaaa ctgctgggta aaggcaccag cgcggccgat gcggttgaag ttccggcccc   3840
ggccgccgtg ctgggtggtc cggaaccgct gatgcaggcg accgcgtggc tgaacgcgta   3900
ttttcatcag ccggaagcga ttgaagaatt tccggttccg cgcgctgcatc atccggtgtt   3960
tcagcaggag agctttaccc gtcaggtgct gtggaaactg ctgaaagtgg ttaaatttgg   4020
cgaagtgatt agctatcagc agctggcggc cctggcgggt aatccggcgg ccaccgccgc   4080
cgttaaaacc gcgctgagcg gtaacccggt gccgattctg attccgtgcc atcgtgtggt   4140
tagctctagc ggtgcggttg gcggttatga aggtggtctg gcggtgaaag agtggctgct   4200
ggcccatgaa ggtcatcgtc tgggtaaacc gggtctggga cctgcagggt ccagcaacgc   4260
taaaatcgat cagctgtctt ctgacgttca gactctgaac gctaaagttg accagctgag   4320
caacgacgtg aacgcaatgc gttccgacgt tcaggctgct aaagatgacg cagctcgtgc   4380
taaccagcgt ctggacaaca tggctactaa ataccgcaag taagcttgaa ttcgcgcgct   4440
cactggccgt cgttttacaa cgtcgtgact gggaaaaccc tggcgttacc caacttaatc   4500
gccttgcagc acatccccct ttcgccagct ggcgtaatag cgaagaggcc cgcaccgatc   4560
gcccttccca acagttgcgc agcctgaatg gcgaatggga cgcgccctgt agcggcgcat   4620
taagcgcggc gggtgtggtg gttacgcgca gcgtgaccgc tacacttgcc agcgccctag   4680
cgcccgctcc tttcgctttc ttcccttcct ttctcgccac gttcgccggc tttccccgtc   4740
aagctctaaa tcggggggctc cctttagggt tccgatttag tgctttacgg cacctcgacc   4800
ccaaaaaact tgattagggt gatggttcac gtagtgggcc atcgccctga tagac         4855
```

<210> SEQ ID NO 4
<211> LENGTH: 5931
<212> TYPE: DNA
<213> ORGANISM: Artificial Sequence
<220> FEATURE:
<223> OTHER INFORMATION: Vector

<400> SEQUENCE: 4

```
ggttttcgc  cctttgacgt tggagtccac gttctttaat agtggactct tgttccaaac    60
tggaacaaca ctcaacccta tctcggtcta ttcttttgat ttataaggga ttttgccgat   120
ttcggcctat tggttaaaaa atgagctgat ttaacaaaaa tttaacgcga attttaacaa   180
aatattaacg cttacaattt aggtggcact tttcggggaa atgtgcgcgg aacccctatt   240
tgtttatttt tctaaataca ttcaaatatg tatccgctca tgagacaata accctgataa   300
atgcttcaat aatattgaaa aaggaagagt atgagtattc aacatttccg tgtcgccctt   360
attcccttt  ttgcggcatt ttgccttcct gttttgctc  acccagaaac gctggtgaaa   420
gtaaaagatg ctgaagatca gttgggtgca cgagtgggtt acatcgaact ggatctcaac   480
agcggtaaga tccttgagag ttttcgcccc gaagaacgtt ttccaatgat gagcactttt   540
aaagttctgc tatgtggcgc ggtattatcc cgtattgacg ccgggcaaga gcaactcggt   600
cgccgcatac actattctca gaatgacttg gttgagtact caccagtcac agaaaagcat   660
cttacggatg gcatgacagt aagagaatta tgcagtgctg ccataaccat gagtgataac   720
```

```
actgcggcca acttacttct gacaacgatc ggaggaccga aggagctaac cgcttttttg    780
cacaacatgg gggatcatgt aactcgcctt gatcgttggg aaccggagct gaatgaagcc    840
ataccaaacg acgagcgtga caccacgatg cctgtagcaa tggcaacaac gttgcgcaaa    900
ctattaactg gcgaactact tactctagct tcccggcaac aattaataga ctggatggag    960
gcggataaag ttgcaggacc acttctgcgc tcggcccttc cggctggctg gtttattgct   1020
gataaatctg gagccggtga gcgtgggtct cgcggtatca ttgcagcact ggggccagat   1080
ggtaagccct cccgtatcgt agttatctac acgacgggga gtcaggcaac tatggatgaa   1140
cgaaatagac agatcgctga gataggtgcc tcactgatta agcattggta actgtcagac   1200
caagtttact catatatact ttagattgat ttaaaacttc atttttaatt taaaaggatc   1260
taggtgaaga tcctttttga taatctcatg accaaaatcc cttaacgtga gttttcgttc   1320
cactgagcgt cagaccccgt agaaaagatc aaaggatctt cttgagatcc ttttttttctg   1380 cgcgtaatct gctgcttgca acaaaaaaac caccgctac cagcggtggt ttgtttgccg   1440
gatcaagagc taccaactct ttttccgaag gtaactggct tcagcagagc gcagatacca   1500
aatactgtcc ttctagtgta gccgtagtta ggccaccact tcaagaactc tgtagcaccg   1560
cctacatacc cgctctgct aatcctgtta ccagtggctg ctgccagtgg cgataagtcg   1620
tgtcttaccg ggttggactc aagacgatag ttaccggata aggcgcagcg gtcgggctga   1680
acggggggtt cgtgcacaca gcccagcttg gagcgaacga cctacaccga actgagatac   1740
ctacagcgtg agctatgcga aagcgccacg cttcccgaag ggagaaaggc ggacaggtat   1800
ccggtaagcg gcagggtcgg agcaggagag cgcacgaggg agcttccagg gggaaacgcc   1860
tggtatcttt atagtcctgt cgggtttcgc cacctctgac ttgagcgtcg atttttgtga   1920
tgctcgtcag gggggcggag cctatggaaa aacgccagca acgcggcctt tttacggttc   1980
ctggcctttt gctggccttt tgctcacatg ttctttcctg cgttatcccc tgattctgtg   2040
gataaccgta ttaccgcctt tgagtgagct gataccgctc gccgcagccg aacgaccgag   2100
cgcagcgagt cagtgagcga ggaagcggaa gagcgcccaa tacgcaaacc gcctctcccc   2160
gcgcgtggcc gttcattaat gcagctggca cgacaggttt cccgactgcg gccgcgacac   2220
ggaaatgttg aatactcata ctcttccttt ttcaatatta ttgaagcatt tatcagggtt   2280
attgtctcat gagcggatac atatttgaat gtatttagaa aaataaacaa ataggggttc   2340
cgcgcacatt tccccgaaaa gtgccacctg catcgattta ttatgacaac ttgacggcta   2400
catcattcac ttttttcttca caaccggcac ggaactcgct cgggctggcc ccggtgcatt   2460
ttttaaatac cgcgagaaa tagagttgat cgtcaaaacc aacattgcga ccgacggtgg   2520
cgataggcat ccgggtggtg ctcaaaagca gcttcgcctg gctgtacgt tggtcctcgc   2580 gccagcttaa gacgctaatc cctaactgct ggcggaaaag atgtgacaga cgcgacggcg   2640
acaagcaaac atgctgtgcg acgctggcga tatcaaaatt gctgtctgcc aggtgatcgc   2700
tgatgtactg acaagcctcg cgtacccgat tatccatcgg tggatggagc gactcgttaa   2760
tcgcttccat gcgccgcagt aacaattgct caagcagatt tatcgccagc agctccgaat   2820
agcgcccttc cccttgcccg gcgttaatga tttgcccaaa caggtcgctg aaatgcggct   2880
ggtgcgcttc atccgggcga aagaaccccg tattggcaaa tattgacggc cagttaagcc   2940
attcatgcca gtaggcgcgc ggacgaaagt aaacccactg gtgataccat tcgcgagcct   3000
ccggatgacg accgtagtga tgaatctctc ctggcgggaa cagcaaaata tcacccggtc   3060
```

```
ggcaaacaaa ttctcgtccc tgattttca ccaccccctg accgcgaatg gtgagattga    3120
gaatataacc tttcattccc agcggtcggt cgataaaaaa atcgagataa ccgttggcct    3180
caatcggcgt taaacccgcc accagatggg cattaaacga gtatcccggc agcaggggat    3240
cattttgcgc ttcagccata cttttcatac tcccgccatt cagagaagaa accaattgtc    3300
catattgcat cagacattgc cgtcactgcg tcttttactg gctcttctcg ctaaccaaac    3360 cggtaaccc gcttattaaa agcattctgt aacaaagcgg gaccaaagcc atgacaaaaa    3420
cgcgtaacaa aagtgtctat aatcacggca gaaaagtcca cattgattat ttgcacggcg    3480
tcacactttg ctatgccata gcatttttat ccataagatt agcggatcct acctgacgct    3540
ttttatcgca actctctact gtttctccat acccgttttt ttggtaagga ggttatctag    3600
aatgcaccat caccatcacc acggcgcgcc taacctcgag ggtacctcca tggacaaaga    3660
ttgcgaaatg aaacgtacca ccctggatag cccgctgggc aaactggaac tgagcggctg    3720
cgaacagggc ctgcatgaaa ttaaactgct gggtaaaggc accagcgcgg ccgatgcggt    3780
tgaagttccg gccccggccg ccgtgctggg tggtccggaa ccgctgatgc aggcgaccgc    3840
gtggctgaac gcgtattttc atcagccgga agcgattgaa gaatttccgg ttccggcgct    3900
gcatcatccg gtgtttcagc aggagagctt tacccgtcag gtgctgtgga aactgctgaa    3960
agtggttaaa tttggcgaag tgattagcta tcagcagctg gcggccctgg cgggtaatcc    4020
ggcggccacc gccgccgtta aaccgcgct gagcggtaac ccggtgccga ttctgattcc    4080
gtgccatcgt gtggttagct ctagcggtgc ggttggcggt tatgaaggtg gtctggcggt    4140
gaaagagtgg ctgctggccc atgaaggtca tcgtctgggt aaaccgggtc tgggacctgc    4200
acaagattac aaagatgacg acgataagtc tgcagggatg accactcaac tggaacaggc    4260
ctgggagcta gcgaaacagc gtttcgcggc ggtgggatt tgatgtcgagg aggcgctgcg    4320 ccaacttgat cgtttacccg tttcaatgca ctgctggcag ggcgatgatg tttccggttt    4380
tgaaaacccg gaaggttcgc tgaccggggg gattcaggcc acaggcaatt atccgggcaa    4440
agcgcgtaat gccagtgagc tacgtgccga tctggaacag gctatgcggc tgattccggg    4500
gccgaaacgg cttaatttac atgccatcta tctggaatca gatacgccag tctcgcgcga    4560
ccagatcaaa ccagagcact tcaaaaactg ggttgaatgg gcgaaagcca atcagctcgg    4620
tctggatttt aaccctcct gcttttcgca tccgctaagc gccgatggct ttacgctttc    4680
ccatgccgac gacagcattc gccagttctg gattgatcac tgcaaagcca gccgtcgcgt    4740
ttcggcctat tttggcgagc aactcggcac accatcggtg atgaacatct ggatcccgga    4800
tggtatgaaa gatatcaccg ttgaccgtct cgccccgcgt cagcgtctgc tggcagcact    4860
ggatgaggtg atcagcgaga agctaaaccc tgcgcaccat atcgacgccg ttgagagcaa    4920 attgttggc attggcgcag agagctacac ggttggctcc aatgagtttt acatggggta    4980
tgccaccagc cgccagactg cgctgtgcct ggacgccggg cacttccacc cgactgaagt    5040
gatttccgac aagatttccg ccgccatgct gtatgtgccg cagttgctgc tgcacgtcag    5100
ccgtccggtt cgctgggaca gcgatcacgt agtgctgctg gatgatgaaa cccaggcaat    5160
tgccagtgag attgtgcgtc acgatctgtt tgaccgggtg catatcggcc ttgacttctt    5220
cgatgcctct atcaaccgca ttgccgcgtg ggtcattggt acacgcaata tgaaaaaagc    5280
cctgctgcgt gcgttgctgg aacctaccgc tgagctgcgc aagctggaag cgccgggcga    5340
ttacactgcg cgtctggcac tgctggaaga gcagaaatcg ttgccgtggc aggcggtctg    5400
ggaaatgtat tgccaacgtc acgatacgcc agcaggtagc gaatggctgg agagcgtgcg    5460
```

```
ggcttatgag aaagaaattt tgagtcgccg cgggtaaaag cttgaattcg cgcgctcact    5520
ggccgtcgtt ttacaacgtc gtgactggga aaaccctggc gttacccaac ttaatcgcct    5580
tgcagcacat ccccctttcg ccagctggcg taatagcgaa gaggcccgca ccgatcgccc    5640
ttcccaacag ttgcgcagcc tgaatggcga atgggacgcg ccctgtagcg gcgcattaag    5700
cgcggcgggt gtggtggtta cgcgcagcgt gaccgctaca cttgccagcg ccctagcgcc    5760
cgctcctttc gctttcttcc cttcctttct cgccacgttc gccggctttc ccgtcaagc    5820 tctaaatcgg gggctccctt tagggttccg atttagtgct ttacggcacc tcgaccccaa    5880
aaaacttgat tagggtgatg gttcacgtag tgggccatcg ccctgataga c             5931
```

<210> SEQ ID NO 5
<211> LENGTH: 48
<212> TYPE: DNA
<213> ORGANISM: Artificial Sequence
<220> FEATURE:
<223> OTHER INFORMATION: coding sequence for randmised spacer

<400> SEQUENCE: 5

```
ggtaccgcyg cygkkwtbgc kwtbgkkgkk gckgkkgcyg cyggtctg                     48
```

<210> SEQ ID NO 6
<211> LENGTH: 12
<212> TYPE: PRT
<213> ORGANISM: Artificial Sequence
<220> FEATURE:
<223> OTHER INFORMATION: peptide linker

<400> SEQUENCE: 6

Gly Ser Asn Ser Asn Asn Gln Ser Lys Pro Ser Ser
1               5                   10

<210> SEQ ID NO 7
<211> LENGTH: 12
<212> TYPE: PRT
<213> ORGANISM: Artificial Sequence
<220> FEATURE:
<223> OTHER INFORMATION: peptide linker

<400> SEQUENCE: 7

Gly Gly Pro Arg Asn Pro Gln Arg His Thr Gly Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: peptide linker

<400> SEQUENCE: 8

Ser Gly Thr Arg His His Asn Ser His Asn Ser Ser
1               5                   10

<210> SEQ ID NO 9
<211> LENGTH: 12
<212> TYPE: PRT
<213> ORGANISM: Artificial Sequence
<220> FEATURE:
<223> OTHER INFORMATION: peptide linker

<400> SEQUENCE: 9

Ser Ser Asn Arg Thr His Lys Ser Asn Asn Ser Ser

<210> SEQ ID NO 10
<211> LENGTH: 12
<212> TYPE: PRT
<213> ORGANISM: Artificial Sequence
<220> FEATURE:
<223> OTHER INFORMATION: peptide linker

<400> SEQUENCE: 10

Ser Gly His Arg Thr Thr Glu Arg Lys His Ser Ser
1               5                   10

<210> SEQ ID NO 11
<211> LENGTH: 12
<212> TYPE: PRT
<213> ORGANISM: Artificial Sequence
<220> FEATURE:
<223> OTHER INFORMATION: peptide linker

<400> SEQUENCE: 11

Gly Gly His Arg His Thr Gln Arg His Asn Gly Gly
1               5                   10

<210> SEQ ID NO 12
<211> LENGTH: 12
<212> TYPE: PRT
<213> ORGANISM: Artificial Sequence
<220> FEATURE:
<223> OTHER INFORMATION: peptide linker

<400> SEQUENCE: 12

Gly Gly Pro Arg Thr Pro Gln Ser Gln Pro Ser Gly
1               5                   10

<210> SEQ ID NO 13
<211> LENGTH: 456
<212> TYPE: PRT
<213> ORGANISM: Artificial Sequence
<220> FEATURE:
<223> OTHER INFORMATION: I27::RL6::KzPG::SNAP::DBP

<400> SEQUENCE: 13

Ser Leu Ile Glu Val Glu Lys Pro Leu Tyr Gly Val Glu Val Phe Val
1               5                   10                  15

Gly Glu Thr Ala His Phe Glu Ile Glu Leu Ser Glu Pro Asp Val His
                20                  25                  30

Gly Gln Trp Lys Leu Lys Gly Gln Pro Leu Thr Ala Ser Pro Asp Cys
            35                  40                  45

Glu Ile Ile Glu Asp Gly Lys Lys His Ile Leu Ile Leu His Asn Cys
        50                  55                  60

Gln Leu Gly Met Thr Gly Glu Val Ser Phe Gln Ala Ala Asn Ala Lys
65                  70                  75                  80

Ser Ala Ala Asn Leu Lys Val Lys Glu Leu Asn Ser Ser Ser Gln Thr
                85                  90                  95

Ser Gly Thr Arg His His Asn Ser His Asn Ser Ser Gly Thr Asn Ser
            100                 105                 110

Pro Pro Lys Val Leu Arg Lys Gly Asp Arg Gly Asp Glu Val Cys Gln
        115                 120                 125

Leu Gln Thr Leu Leu Asn Leu Cys Gly Tyr Asp Val Gly Lys Pro Asp
    130                 135                 140

Gly Ile Phe Gly Asn Asn Thr Phe Asn Gln Val Val Lys Phe Gln Lys

```
                145                 150                 155                 160
Asp Asn Cys Leu Asp Ser Asp Gly Ile Val Gly Lys Asn Thr Trp Ala
                165                 170                 175

Glu Leu Phe Ser Lys Tyr Ser Pro Pro Ser Met Asp Lys Asp Cys Glu
            180                 185                 190

Met Lys Arg Thr Thr Leu Asp Ser Pro Leu Gly Lys Leu Glu Leu Ser
        195                 200                 205

Gly Cys Glu Gln Gly Leu His Glu Ile Lys Leu Leu Gly Lys Gly Thr
    210                 215                 220

Ser Ala Ala Asp Ala Val Glu Val Pro Ala Pro Ala Ala Val Leu Gly
225                 230                 235                 240

Gly Pro Glu Pro Leu Met Gln Ala Thr Ala Trp Leu Asn Ala Tyr Phe
                245                 250                 255

His Gln Pro Glu Ala Ile Glu Glu Phe Pro Val Pro Ala Leu His His
            260                 265                 270

Pro Val Phe Gln Gln Glu Ser Phe Thr Arg Gln Val Leu Trp Lys Leu
        275                 280                 285

Leu Lys Val Val Lys Phe Gly Glu Val Ile Ser Tyr Gln Gln Leu Ala
    290                 295                 300

Ala Leu Ala Gly Asn Pro Ala Ala Thr Ala Ala Val Lys Thr Ala Leu
305                 310                 315                 320

Ser Gly Asn Pro Val Pro Ile Leu Ile Pro Cys His Arg Val Val Ser
                325                 330                 335

Ser Ser Gly Ala Val Gly Gly Tyr Glu Gly Gly Leu Ala Val Lys Glu
            340                 345                 350

Trp Leu Leu Ala His Glu Gly His Arg Leu Gly Lys Pro Gly Leu Gly
        355                 360                 365

Pro Ala Gly Asn Ser Gly Lys Gly Ala Val Asn Ile Asn Ala Ala Ser
    370                 375                 380

Gln Gln Glu Leu Glu Ala Leu Pro Gly Ile Gly Pro Ala Lys Ala Lys
385                 390                 395                 400

Ala Ile Ala Glu Tyr Arg Ala Gln Asn Gly Ala Phe Lys Ser Val Asp
                405                 410                 415

Asp Leu Ile Lys Val Lys Gly Ile Gly Pro Ala Val Leu Ala Lys Leu
            420                 425                 430

Lys Asp Gln Ala Ser Val Gly Ala Pro Ala Pro Lys Gly Pro Ala Lys
        435                 440                 445

Pro Val Leu Pro Ala Val Lys Lys
    450                 455

<210> SEQ ID NO 14
<211> LENGTH: 1371
<212> TYPE: DNA
<213> ORGANISM: Artificial Sequence
<220> FEATURE:
<223> OTHER INFORMATION: I27::RL6::KzPG::SNAP::DBP coding sequence

<400> SEQUENCE: 14
agcctgattg aagttgaaaa accgttgtac ggcgtggagg tgttcgtcgg cgagactgcc      60
cacttcgaaa ttgaactgag cgaaccggac gttcatggtc agtggaagct gaagggtcag    120
ccgctgaccg cgagcccgga ctgcgagatc atcgaggatg gtaagaagca tattctgatc    180
ctgcacaatt gtcagctggg tatgaccggc gaggtcagct ttcaagctgc gaacgcaaaa    240
agcgcagcga atttgaaagt taagagctg aactcgagca gccagaccag cggcacccgc    300
```

| | | |
|---|---|---|
| caccacaata gccataacag cagcggtacc aacagcccac cgaaagtgtt acgcaagggt | 360 | |
| gatcgtggcg atgaagtgtg ccagctgcaa acgttactga atctctgcgg ttatgacgtt | 420 | |
| ggcaaacctg atggcatttt cggcaataac accttcaacc aggttgtgaa attccagaag | 480 | |
| gacaactgtt tagacagcga tggtattgtg ggtaaaaaca cgtgggcaga actgttcagc | 540 | |
| aaatactcgc caccgtccat ggacaaagat tgcgaaatga acgtaccac cctggatagc | 600 | |
| ccgctgggca aactggaact gagcggctgc gaacagggcc tgcatgaaat taaactgctg | 660 | |
| ggtaaaggca ccagcgcggc cgatgcggtt gaagttccgg ccccggccgc cgtgctgggt | 720 | |
| ggtccggaac cgctgatgca ggcgaccgcg tggctgaacg cgtattttca tcagccggaa | 780 | |
| gcgattgaag aatttccggt tccggcgctg catcatccgg tgtttcagca ggagagcttt | 840 | |
| acccgtcagg tgctgtggaa actgctgaaa gtggttaaat tggcgaagt gattagctat | 900 | |
| cagcagctgg cggccctggc gggtaatccg gcggccaccg ccgccgttaa aaccgcgctg | 960 | |
| agcggtaacc cggtgccgat tctgattccg tgccatcgtg tggttagctc tagcggtgcg | 1020 | |
| gttggcggtt atgaaggtgg tctggcggtg aaagagtggc tgctggccca tgaaggtcat | 1080 | |
| cgtctgggta aaccgggtct gggacctgca gggaactcag gtaaaggcgc agtgaacatt | 1140 | |
| aacgccgcat cacagcaaga actggaggcg ttaccgggta ttggccctgc aaaggccaaa | 1200 | |
| gcgatcgctg aatatcgcgc acaaaatggc gcattcaaga gcgtcgacga tctgatcaaa | 1260 | |
| gtcaagggca tcggtccggc agtgctagcc aagctgaaag accaggcatc agttggtgca | 1320 | |
| ccggctccta aaggtccggc caaaccggtc ctgcccgctg taaagaaata a | 1371 | |

<210> SEQ ID NO 15
<211> LENGTH: 5017
<212> TYPE: DNA
<213> ORGANISM: Artificial Sequence
<220> FEATURE:
<223> OTHER INFORMATION: Library scaffold vector

<400> SEQUENCE: 15

| | | |
|---|---|---|
| ggttttcgc cctttgacgt tggagtccac gttctttaat agtggactct tgttccaaac | 60 | |
| tggaacaaca ctcaacccta tctcggtcta ttcttttgat ttataaggga ttttgccgat | 120 | |
| ttcggcctat tggttaaaaa atgagctgat ttaacaaaaa tttaacgcga attttaacaa | 180 | |
| aatattaacg cttacaattt aggtggcact tttcggggaa atgtgcgcgg aaccccctatt | 240 | |
| tgtttatttt tctaaataca ttcaaatatg tatccgctca tgagacaata accctgataa | 300 | |
| atgcttcaat aatattgaaa aaggaagagt atgagtattc aacatttccg tgtcgccctt | 360 | |
| attcccttttt ttgcggcatt ttgccttcct gttttttgctc acccagaaac gctggtgaaa | 420 | |
| gtaaaagatg ctgaagatca gttgggtgca cgagtgggtt acatcgaact ggatctcaac | 480 | |
| agcggtaaga tccttgagag ttttcgcccc gaagaacgtt ttccaatgat gagcactttt | 540 | |
| aaagttctgc tatgtggcgc ggtattatcc cgtattgacg ccgggcaaga gcaactcggt | 600 | |
| cgccgcatac actattctca gaatgacttg gttgagtact caccagtcac agaaaagcat | 660 | |
| cttacggatg gcatgacagt aagagaatta tgcagtgctg ccataaccat gagtgataac | 720 | |
| actgcggcca acttacttct gacaacgatc ggaggaccga aggagctaac cgcttttttg | 780 | |
| cacaacatgg gggatcatgt aactcgcctt gatcgttggg aaccggagct gaatgaagcc | 840 | |
| ataccaaacg acgagcgtga caccacgatg cctgtagcaa tggcaacaac gttgcgcaaa | 900 | |
| ctattaactg gcgaactact tactctagct tcccggcaac aattaataga ctggatggag | 960 | |
| gcggataaag ttgcaggacc acttctgcgc tcggcccttc cggctggctg gtttattgct | 1020 | |

```
gataaatctg gagccggtga gcgtgggtct cgcggtatca ttgcagcact ggggccagat    1080
ggtaagccct cccgtatcgt agttatctac acgacgggga gtcaggcaac tatggatgaa    1140
cgaaatagac agatcgctga gataggtgcc tcactgatta agcattggta actgtcagac    1200
caagtttact catatatact ttagattgat ttaaaacttc atttttaatt taaaaggatc    1260
taggtgaaga tccttttttga taatctcatg accaaaatcc cttaacgtga gttttcgttc    1320
cactgagcgt cagaccccgt agaaaagatc aaaggatctt cttgagatcc ttttttttctg    1380 cgcgtaatct gctgcttgca aacaaaaaaa ccaccgctac cagcggtggt ttgtttgccg    1440
gatcaagagc taccaactct ttttccgaag gtaactggct tcagcagagc gcagatacca    1500
aatactgtcc ttctagtgta gccgtagtta ggccaccact tcaagaactc tgtagcaccg    1560
cctacatacc cgctctgct aatcctgtta ccagtggctg ctgccagtgg cgataagtcg    1620
tgtcttaccg ggttggactc aagacgatag ttaccggata aggcgcagcg gtcgggctga    1680 acgggggggtt cgtgcacaca gcccagcttg gagcgaacga cctacaccga actgagatac    1740
ctacagcgtg agctatgcga aagcgccacg cttcccgaag ggagaaaggc ggacaggtat    1800
ccggtaagcg gcagggtcgg agcaggagag cgcacgaggg agcttccagg gggaaacgcc    1860
tggtatcttt atagtcctgt cgggtttcgc cacctctgac ttgagcgtcg atttttgtga    1920
tgctcgtcag gggggcggag cctatggaaa aacgccagca acgcggcctt tttacggttc    1980
ctggcctttt gctggccttt tgctcacatg ttctttcctg cgttatcccc tgattctgtg    2040
gataaccgta ttaccgcctt tgagtgagct gataccgctc gccgcagccg aacgaccgag    2100
cgcagcgagt cagtgagcga ggaagcggaa gagcgcccaa tacgcaaacc gcctctcccc    2160
gcgcgtggcc gttcattaat gcagctggca cgacaggttt cccgactgcg gccgcgacac    2220
ggaaatgttg aatactcata ctcttccttt ttcaatatta ttgaagcatt tatcagggtt    2280
attgtctcat gagcggatac atatttgaat gtatttagaa aaataaacaa ataggggttc    2340
cgcgcacatt tccccgaaaa gtgccacctg catcgattta ttatgacaac ttgacggcta    2400
catcattcac ttttttcttca caaccggcac ggaactcgct cgggctggcc ccggtgcatt    2460
ttttaaatac ccgcgagaaa tagagttgat cgtcaaaacc aacattgcga ccgacggtgg    2520
cgataggcat ccgggtggtg ctcaaaagca gcttcgcctg gctgatacgt tggtcctcgc    2580
gccagcttaa gacgctaatc cctaactgct ggcggaaaag atgtgacaga cgcgacggcg    2640
acaagcaaac atgctgtgcg acgctggcga tatcaaaatt gctgtctgcc aggtgatcgc    2700
tgatgtactg acaagcctcg cgtacccgat tatccatcgg tggatggagc gactcgttaa    2760
tcgcttccat gcgccgcagt aacaattgct caagcagatt tatcggcagc agctccgaat    2820
agcgcccttc cccttgcccg gcgttaatga tttgcccaaa caggtcgctg aaatgcggct    2880
ggtgcgtttc atccgggcga aagaacccccg tattggcaaa tattgacggc cagttaagcc    2940
attcatgcca gtaggcgcgc ggacgaaagt aaacccactg gtgataccat tcgcgagcct    3000
ccggatgacg accgtagtga tgaatctctc ctggcgggaa cagcaaaata tcacccggtc    3060
ggcaaacaaa ttctcgtccc tgattttttca ccaccccctg accgcgaatg gtgagattga    3120
gaatataacc tttcattccc agcggtcggt cgataaaaaa atcgagataa ccgttggcct    3180
caatcggcgt taaacccgcc accagatggg cattaaacga gtatcccggc agcaggggat    3240
cattttgcgc ttcagccata cttttcatac tcccgccatt cagagaagaa accaattgtc    3300
catattgcat caaacattgc cgtcactgcg tcttttactg gctcttctcg ctaaccaaac    3360
```

```
cggtaacccc gcttattaaa agcattctgt aacaaagcgg gaccaaagcc atgacaaaaa   3420
cgcgtaacaa aagtgtctat aatcacggca gaaaagtcca cattgattat ttgcacggcg   3480
tcacactttg ctatgccata gcattttat ccataagatt agcggatcct acctgacgct    3540
ttttatcgca actctctact gtttctccat acccgttttt ttggtaagga ggttatctag   3600
aatgggagac gcctaatgaa gttcgtctca gaccagcctg attgaagttg aaaaaccgtt   3660
gtacggcgtg gaggtgttcg tcggcgagac tgcccacttc gaaattgaac tgagcgaacc   3720
ggacgttcat ggtcagtgga agctgaaggg tcagccgctg accgcgagcc cggactgcga   3780
gatcatcgag gatggtaaga agcatattct gatcctgcac aattgtcagc tgggtatgac   3840
cggcgaggtc agctttcaag ctgcgaacgc aaaaagcgca gcgaatttga agttaaaga    3900 gctgaactcg agcagccaga ccagcggcac ccgccaccac aatagccata acagcagcgg   3960
taccaacagc ccaccgaaag tgttacgcaa gggtgatcgt ggcgatgaag tgtgccagct   4020
gcaaacgtta ctgaatctct gcggttatga cgttggcaaa cctgatggca ttttcggcaa   4080
taacaccttc aaccaggttg tgaaattcca gaaggacaac tgtttagaca gcgatggtat   4140
tgtgggtaaa aacacgtggg cagaactgtt cagcaaatac tcgccaccgt ccatggacaa   4200
agattgcgaa atgaaacgta ccaccctgga tagcccgctg gcaaactgg aactgagcgg    4260 ctgcgaacag ggcctgcatg aaattaaact gctgggtaaa ggcaccagcg cggccgatgc   4320
ggttgaagtt ccggccccgg ccgccgtgct gggtggtccg gaaccgctga tgcaggcgac   4380
cgcgtggctg aacgcgtatt ttcatcagcc ggaagcgatt gaagaatttc cggttccggc   4440
gctgcatcat ccggtgtttc agcaggagag ctttacccgt caggtgctgt ggaaactgct   4500
gaaagtggtt aaatttggcg aagtgattag ctatcagcag ctggcggccc tggcgggtaa   4560
tccggcggcc accgccgccg ttaaaaccgc gctgagcggt aacccggtgc cgattctgat   4620
tccgtgccat cgtgtggtta gctctagcgg tgcggttggc ggttatgaag tggtctggc    4680 ggtgaaagag tggctgctgg cccatgaagg tcatcgtctg ggtaaaccgg tctgggacc    4740 tgcagggaac tcaggtaaag cgcagtgaa cattaacgcc gcatcacagc aagaactgga    4800
ggcgttaccg ggtattggcc ctgcaaaggc caaagcgatc gctgaatatc gcgcacaaaa   4860
tggcgcattc aagagcgtcg acgatctgat caaagtcaag gcatcggtc ggcagtgct     4920 agccaagctg aaagaccagg catcagttgg tgcaccggct cctaaaggtc ggccaaacc    4980 ggtcctgccc gctgtaaaga aataaaagct tgaattc                            5017
```

<210> SEQ ID NO 16
<211> LENGTH: 90
<212> TYPE: PRT
<213> ORGANISM: Artificial Sequence
<220> FEATURE:
<223> OTHER INFORMATION: peptide spacer

<400> SEQUENCE: 16

Ser Leu Ile Glu Val Glu Lys Pro Leu Tyr Gly Val Glu Val Phe Val
1               5                   10                  15

Gly Glu Thr Ala His Phe Glu Ile Glu Leu Ser Glu Pro Asp Val His
                20                  25                  30

Gly Gln Trp Lys Leu Lys Gly Gln Pro Leu Thr Ala Ser Pro Asp Cys
            35                  40                  45

Glu Ile Ile Glu Asp Gly Lys Lys His Ile Leu Ile Leu His Asn Cys
        50                  55                  60

-continued

```
Gln Leu Gly Met Thr Gly Glu Val Ser Phe Gln Ala Ala Asn Ala Lys
 65                  70                  75                  80

Ser Ala Ala Asn Leu Lys Val Lys Glu Leu
             85                  90
```